(12) United States Patent
Inoue et al.

(10) Patent No.: US 8,785,003 B2
(45) Date of Patent: Jul. 22, 2014

(54) MATERIAL FOR ORGANIC ELECTROLUMINESCENCE DEVICE AND ORGANIC ELECTROLUMINESCENCE DEVICE USING THE SAME

(75) Inventors: Tetsuya Inoue, Sodegaura (JP); Kumiko Hibino, Sodegaura (JP); Kei Yoshida, Sodegaura (JP); Kazuki Nishimura, Sodegaura (JP); Toshihiro Iwakuma, Sodegaura (JP)

(73) Assignee: Idemtisu Kosan Co., Ltd., Tokyo (JP)

( * ) Notice: Subject to any disclaimer, the term of this patent is extended or adjusted under 35 U.S.C. 154(b) by 9 days.

(21) Appl. No.: 13/041,071

(22) Filed: Mar. 4, 2011

(65) Prior Publication Data

US 2011/0291081 A1 Dec. 1, 2011

Related U.S. Application Data

(60) Provisional application No. 61/319,367, filed on Mar. 31, 2010.

(30) Foreign Application Priority Data

Mar. 5, 2010 (JP) .................................. 2010-049839

(51) Int. Cl.

| | | |
|---|---|---|
| H01L 51/54 | (2006.01) | |
| H01L 51/00 | (2006.01) | |
| C09K 11/06 | (2006.01) | |
| C07D 401/14 | (2006.01) | |
| C07F 7/08 | (2006.01) | |
| C07D 403/14 | (2006.01) | |
| H05B 33/14 | (2006.01) | |
| H01L 51/50 | (2006.01) | |

(52) U.S. Cl.
CPC ........... *C07D 401/14* (2013.01); *H01L 51/5012* (2013.01); *H01L 51/0067* (2013.01); *H01L 51/0072* (2013.01); *C09K 11/06* (2013.01); *C07F 7/0812* (2013.01); *C09K 2211/1059* (2013.01); *C09K 2211/1029* (2013.01); *H01L 51/5048* (2013.01); *C07D 403/14* (2013.01); *C09K 2211/1044* (2013.01); *C07F 7/0814* (2013.01); *H05B 33/14* (2013.01); *Y10S 428/917* (2013.01)

USPC ........... 428/690; 428/917; 313/504; 313/505; 313/506; 257/40; 257/E51.05; 257/E51.026; 257/E51.032; 548/304.1; 548/418; 548/440; 548/444; 546/18; 546/79; 546/81; 546/101; 544/234

(58) Field of Classification Search
USPC .................. 428/690, 917; 313/504, 505, 506; 257/40, E51.05, E51.026, E51.032; 548/440, 418, 304.1, 444; 546/18, 79, 546/81, 101; 544/234
See application file for complete search history.

(56) References Cited

FOREIGN PATENT DOCUMENTS

| EP | 1202608 | * | 5/2002 | ............. H05B 33/14 |
| JP | 2000-169448 | | 6/2000 | |

(Continued)

OTHER PUBLICATIONS

International Search Report and Written Opinion issued May 10, 2011 in PCT /JP2011/055077 (with English translation of category of cited documents).

Primary Examiner — Gregory Clark
(74) Attorney, Agent, or Firm — Oblon, Spivak, McClelland, Maier & Neustadt, L.L.P.

(57) ABSTRACT

An organic EL device material includes at least a unit including 3,5-biscarbazolylphenyl group, a unit including 4-carbazolylphenyl group, and a compound including a unit including a nitrogen-containing aromatic heterocyclic ring bonding the unit including 3,5-biscarbazolylphenyl group and the unit including 4-carbazolylphenyl group.

11 Claims, 1 Drawing Sheet

(56) References Cited

FOREIGN PATENT DOCUMENTS

| | | |
|---|---|---|
| JP | 2004-178895 | 6/2004 |
| JP | 2006-188493 | 7/2006 |
| JP | 2006-199679 | 8/2006 |
| JP | 4316387 | 5/2009 |
| WO | WO 03/080760 A1 | 2/2003 |
| WO | WO 2008/127057 A1 | 10/2008 |
| WO | WO 2009/031855 * | 3/2009 ............ C09K 11/06 |
| WO | WO 2009/031855 A1 | 3/2009 |
| WO | WO 2009/057978 | 5/2009 |

* cited by examiner

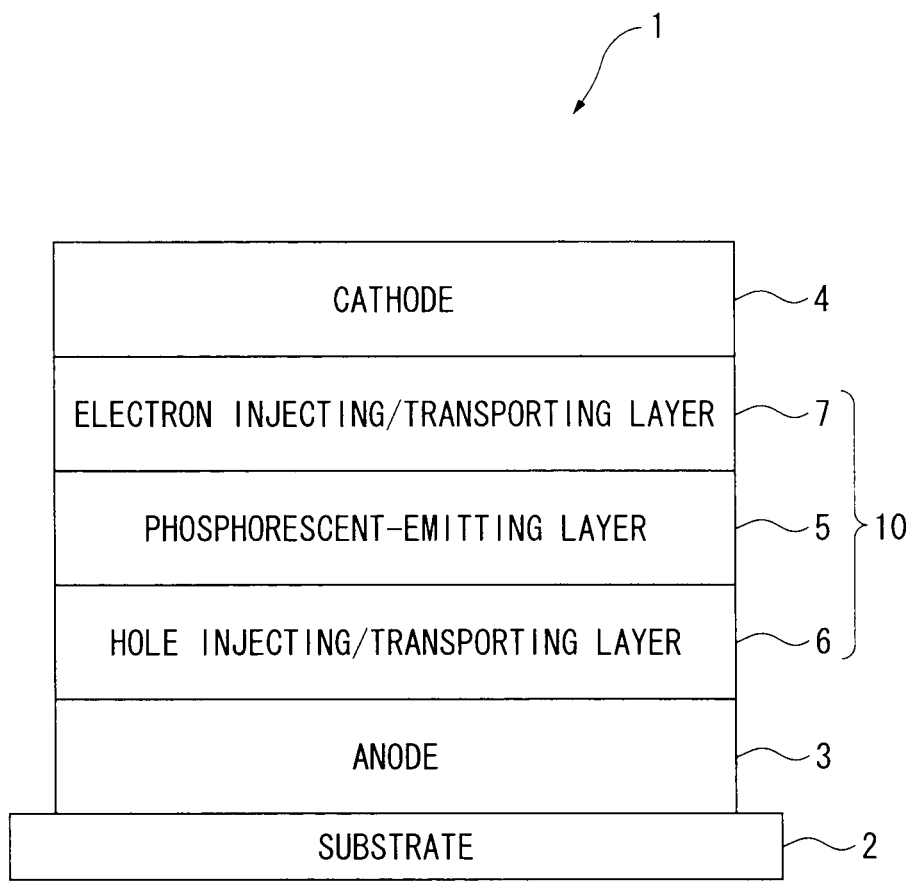

MATERIAL FOR ORGANIC ELECTROLUMINESCENCE DEVICE AND ORGANIC ELECTROLUMINESCENCE DEVICE USING THE SAME

The entire disclosure of Japanese Patent Application No. 2010-049839 filed Mar. 5, 2010, and U.S. Provisional Application 61/319367 filed Mar. 31, 2010 is expressly incorporated by reference herein.

BACKGROUND OF THE INVENTION

1. Field of the Invention

The present invention relates to an organic electroluminescence (EL) device material and an organic electroluminescence (EL) device using the same.

2. Description of Related Art

An organic EL device, which includes an organic thin-film layer (in which an emitting layer is included) between an anode and a cathode, has been known to emit light using exciton energy generated by recombination of holes and electrons that have been injected into the emitting layer (see e.g., Patent Literature 1: WO2003-080760, Patent Literature 2: JP-A-2006-188493, Patent Literature 3: JP-A-2006-199679, Patent Literature 4: JP-A-2004-178895, and Patent Literature 5: JP-A-2000-169448).

Such an organic EL device, which has the advantages as a self-emitting device, is expected to serve as an emitting device excellent in luminous efficiency, image quality, power consumption and thin design.

In forming the emitting layer, a doping method, according to which an emitting material (dopant) is doped to a host, has been known as a usable method.

The emitting layer formed by the doping method can efficiently generate excitons from electric charges injected into the host. With the exciton energy generated by the excitons being transferred to the dopant, the dopant can emit light with high efficiency.

Recently, in order to upgrade an organic EL device, a further study on a doping method has been made to seek favorable host materials.

For instance, Patent Literatures 1 to 5 disclose inventions related to such host materials. Patent Literatures 1 to 5 disclose compounds, such as below-listed Compounds I to VI, in which a carbazolyl group and a nitrogen-containing aromatic ring are contained in the same molecule.

Compound I disclosed in Patent Literature 1 has a structure in which two carbazole skeletons are bonded to a benzene ring in meta positions (3,5-positions) and an electron-deficient nitrogen-containing hetero aromatic ring structure. A carbazole skeleton (a representative example of which is polyvinylcarbazole) has been known through the ages as a main skeleton for a hole transporting material. In contrast, an electron-deficient nitrogen-containing hetero aromatic ring structure has been known as a structure with a high electron transporting capability. Compound I disclosed in Patent Literature 1, in which a hole transporting skeleton and an electron transporting skeleton are combined, is a material aimed at a balanced charge transport.

In Compound II disclosed in Patent Literature 1, two structures in each of which two carbazole skeletons are bonded to a benzene ring in meta positions (3,5-positions) are symmetrically disposed relative to a pyridine ring as an electron-deficient nitrogen-containing hetero aromatic ring.

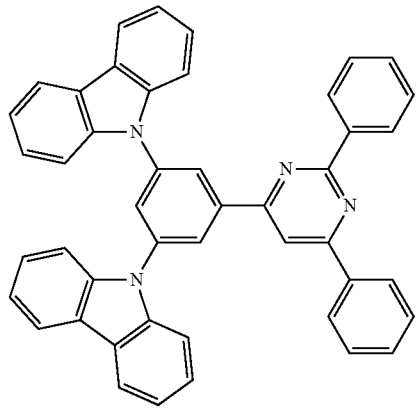

Compound I

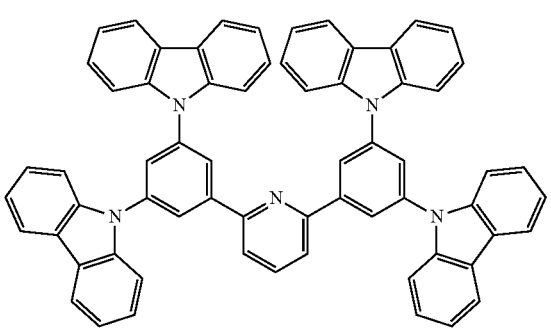

Compound II

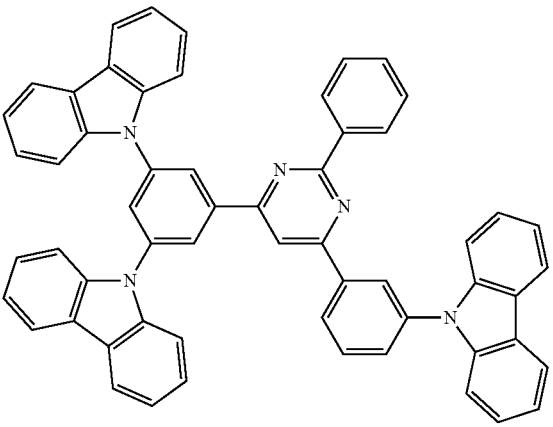

Compound III

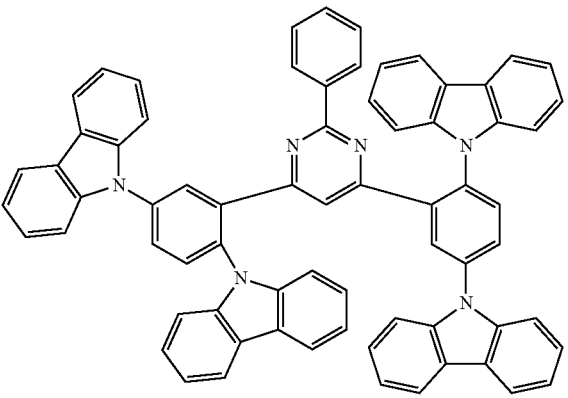

Compound IV

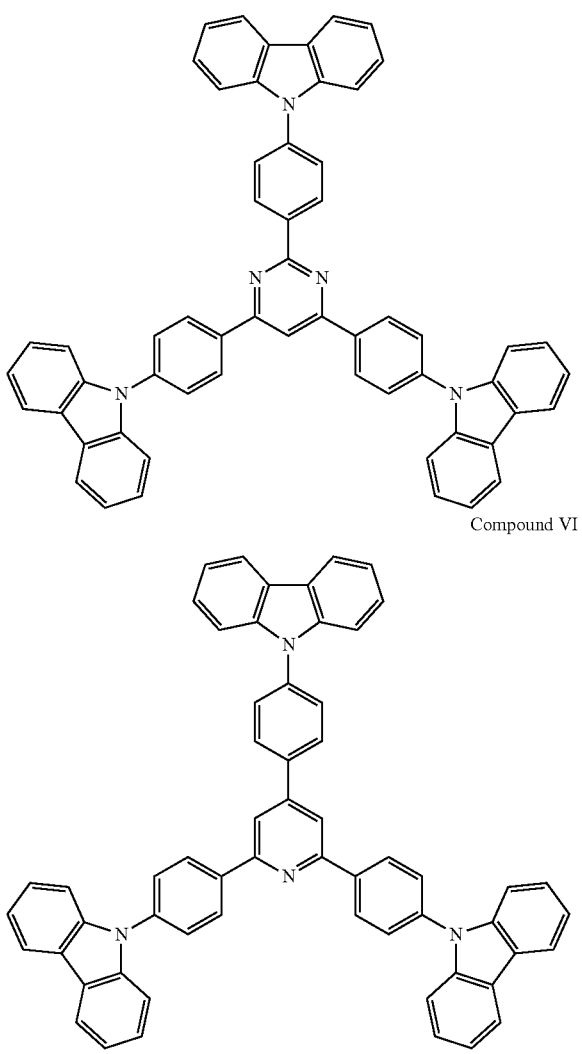

Compound V

Compound VI

However, Compound I is structured such that the carbazole skeletons are bonded to the benzene ring in meta positions and, thus, the carbazolyl groups are bent rightward and leftward relative to the bond axis between the pyrimidine ring and the benzene ring (two conjugated aromatic rings), hampering overlap of the carbazole skeletons between molecules. In view of this, since the hole transporting capability is insufficient and positions of electron recombination tend to be shifted toward the anode, it may not be possible to provide favorable luminescence property and life property.

Compound II is likewise structured such that carbazole skeletons are bonded to a benzene ring in meta positions and, thus, the carbazolyl groups are bent rightward and leftward relative to the bond axis between a pyridine ring and the benzene ring (two conjugated aromatic rings), so that the hole transporting capability is insufficient for the same reason.

This is also applicable to Compound III disclosed in Patent Literature 2. Specifically, since carbazolyl groups are bent relative to the bond axis between a pyrimidine ring and a benzene ring to which carbazole skeletons are bonded, the hole transporting capability is insufficient for the above reason.

In Compound IV disclosed in Patent Literature 3, carbazolyl groups are bonded to a benzene ring in 2,5 positions, which are sterically-congested bond positions relative to the bond axis between a pyrimidine ring and a benzene ring to which the carbazole skeletons are bonded (two conjugated aromatic rings). In view of this, it is predicted that overlap of the carbazole skeletons between the molecules is further hampered and, thus, it may not be possible to provide a sufficient hole transporting capability.

In contrast, Compound V disclosed in Patent Literature 4 is structured such that each of three carbazolyl groups is disposed on an extension (4-position, para position) of the bond axis between a benzene ring to which the carbazolyl group is bonded and a pyrimidine ring (two conjugated aromatic rings). Compound VI disclosed in Patent Literature 5 is structured such that each of three carbazolyl groups is disposed on an extension (4-position, para position) of the bond axis between a benzene ring to which the carbazolyl group is bonded and a pyridine ring (two conjugated aromatic rings). In such a structure, an increased overlap of the carbazolyl groups between the molecules is expected to improve the hole transporting capability. In fact, 4,4'-N,N'-dicarbazolyl-biphenyl (CBP) structured such that two carbazolylphenyl groups are bonded in para positions has been known to have a significantly high hole transporting capability. However, all the carbazolyl groups are disposed in 4-positions (para positions), which makes the hole transporting capability extremely high. In view of this, it may be difficult to provide an optimal carrier balance in an organic EL device.

SUMMARY OF THE INVENTION

Accordingly, an object of the invention is to provide a new organic EL device material that has both hole transporting capability and electron transporting capability and is excellent in carrier balance and a long-life phosphorescent organic EL device using such an organic EL device material.

Through a continuous devoted study for attaining the above object, the inventors have discovered that a compound including at least a unit including 3,5-biscarbazolylphenyl group, a unit including 4-carbazolylphenyl group, and a bond unit including an electron-deficient nitrogen-containing aromatic heterocyclic ring bonding the units effectively works to optimize carrier balance in an emitting layer of an organic EL element, and have completed the invention based on the above. Incidentally, a "hydrogen atom" includes a "deuterium atom" herein.

Specifically, an organic EL device material according to an aspect of the invention includes at least a unit including 3,5-biscarbazolylphenyl group, a unit including 4-carbazolylphenyl group, and a compound including a unit including a nitrogen-containing aromatic heterocyclic ring bonding the unit including 3,5-biscarbazolylphenyl group and the unit including 4-carbazolylphenyl group.

The unit including 3,5-biscarbazolylphenyl group is preferably represented by the following formula (U1).

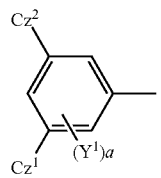

(U1)

In the formula:

a represents an integer of 0 to 3;

$Y^1$ represents a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 carbon atoms forming a ring (hereinafter referred to as "ring carbon atoms"), or a substituted or unsubstituted aromatic heterocyclic group having 2 to 10 ring carbon atoms; and when a is an integer of 2 or more, $Y^1$ may be the same or different.

The unit including 4-carbazolylphenyl group is preferably represented by the following formula (U2).

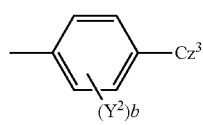

(U2)

In the formula:

b represents an integer of 0 to 4;

$Y^2$ represents a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms; and when b is an integer of 2 or more, $Y^2$ may be the same or different.

Preferably, $Cz^1$, $Cz^2$ and $Cz^3$ each independently represent a monovalent residue obtained by removing any one of $Rx_1$ to $Rx_8$ constituting $Z_1$ to $Z_8$ in the following formula (U3) or a monovalent residue obtained by removing $Z_9$. Particularly, a monovalent residue obtained by removing $Rx_3$, $Rx_7$ or $Z_9$ is preferable.

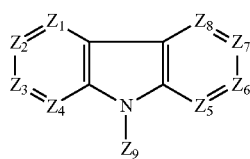

(U3)

In the formula:

$Z_1$ to $Z_8$ each represent $CRx_1$ to $CRx_8$ or N;

$Rx_1$ to $Rx_8$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms;

$Z_1$ and $Z_2$, $Z_2$ and $Z_3$, $Z_3$ and $Z_4$, $Z_5$ and $Z_6$, $Z_6$ and $Z_7$, and $Z_7$ and $Z_8$ may form rings, respectively; and $Z_9$ represents a hydrogen atom, a substituted or unsubstituted and linear, branched or cyclic alkyl group having 1 to 20 carbon atoms, a branched or cyclic haloalkyl group having 1 to 20 carbon atoms, a substituted or unsubstituted aromatic hydrocarbon group having 6 to 30 ring carbon atoms, or a substituted or unsubstituted aromatic heterocyclic group having 2 to 10 ring carbon atoms.

Further, the compound unit including the nitrogen-containing aromatic heterocyclic ring is preferably a divalent or more group of a monocyclic nitrogen-containing aromatic heterocyclic compound and a fused polycyclic nitrogen-containing aromatic heterocyclic compound.

Preferably, the organic EL device material is represented by, in particular, the following formula (1).

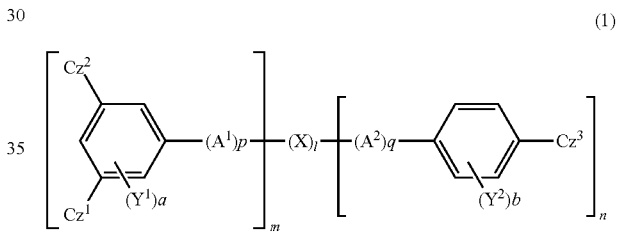

(1)

In the formula:

$A^1$ and $A^2$ each represent a substituted or unsubstituted aromatic hydrocarbon group having 6 to 60 ring carbon atoms;

$Cz^1$ to $Cz^3$ each independently represent a substituted or unsubstituted carbazolyl group and may be mutually the same or different;

X represents a substituted or unsubstituted nitrogen-containing aromatic heterocyclic ring;

$Y^1$ and $Y^2$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms;

a represents an integer of 0 to 3 and b represents an integer of 0 to 4;

l, m and n each independently represent an integer of 1 to 3;

when l is 2 or more, X may be the same or different;

m represents an integer of 1 or 2 as the number of substituent(s) being directly bonded to X and being represented by the following formula (2);
when m is 2, structures represented by the formula (2) may be the same or different;
n represents an integer of 1 or 2 as the number of substituent(s) being directly bonded to X and being represented by the following formula (3);
when n is 2, structures represented by the formula (3) may be the same or different;
p and q each independently represent an integer of 0 to 3; when p is 2 or more, $A^1$ may be the same or different; and when q is 2 or more, $A^2$ may be the same or different.

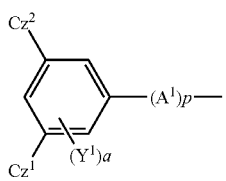

(2)

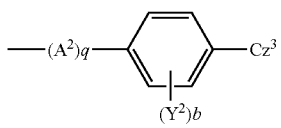

(3)

In the aspect of the invention, l=1 and m=1 are preferable in the formula (1).

In the organic EL device material, the nitrogen-containing aromatic heterocyclic ring is preferably a nitrogen-containing hetero aromatic ring selected from a substituted or unsubstituted pyridine ring, pyrimidine ring, triazine ring and indole ring.

In the organic EL device material, n=1 is preferable in the formula (1).

In the organic EL device material, X in the formula (1) is more preferably a substituted or unsubstituted pyrimidine ring.

The organic EL device material is preferably represented by the following formula (4).

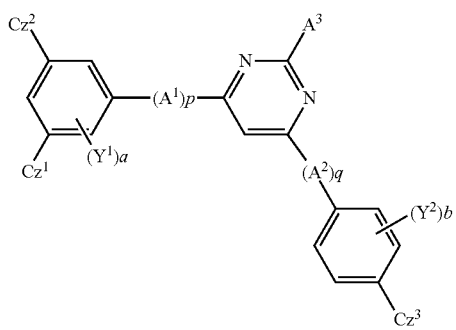

(4)

In the formula, $A^3$ represents a substituted or unsubstituted aromatic hydrocarbon group having 6 to 30 ring carbon atoms.

In the organic EL device material, preferably, each of $Cz^1$ to $Cz^3$ in the formula (1) or (4) is independently represented by the following formula (5) or formula (6).

In the following formulae, "*" represents a bond position to the benzene ring.

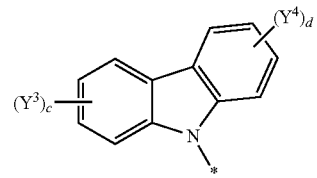

(5)

In the formula (5):
$Y^3$ and $Y^4$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms; and
c and d each independently represent an integer of 1 to 4.

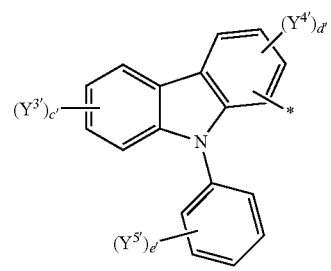

(6)

In the formula (6):
$Y^{3'}$, $Y^{4'}$ and $Y^{5'}$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms; and
c' represents an integer of 1 to 4, d' represents an integer of 1 to 3, and e' represents an integer of 1 to 5.

In the organic EL device material, q=0 is preferable in the formula (1) or (4).

The organic EL device according to another aspect of the invention includes: a cathode; an anode; and an organic thin-film layer provided between the cathode and the anode, the organic thin-film layer formed out of one or more layers including an emitting layer, in which at least one layer of the organic thin-film layer contains the above organic EL device material.

In the organic EL device, the emitting layer preferably contains the above organic EL device material as a host material.

In the organic EL device, the emitting layer preferably further contains a phosphorescent material.

In the organic EL device, preferably, the emitting layer includes a host material and a phosphorescent material, in which the phosphorescent material is an ortho metalation of a complex of a metal atom selected from iridium (Ir), osmium (Os) and platinum (Pt).

Preferably, the organic thin-film layer in the organic EL device includes an electron injecting layer provided between the cathode and the emitting layer, the electron injecting layer containing a nitrogen-containing cyclic derivative.

Preferably, the organic thin-film layer in the organic EL device includes an electron transporting layer provided between the cathode and the emitting layer, the electron transporting layer containing the organic EL device material.

In the organic EL device, a reduction-causing dopant is preferably present at an interfacial region between the cathode and the organic thin-film layer.

According to the aspect(s) of the invention, a compound represented by the formula (1) is used as an organic EL device material to provide a long-life organic EL device. Further, such an organic EL device material is usable as a material for an organic electronic device for an organic solar battery, an organic semiconductor laser, a sensor using an organic substance and an organic TFT.

BRIEF DESCRIPTION OF THE DRAWING

FIG. 1 schematically shows an exemplary arrangement of an organic EL device according to an exemplary embodiment of the invention.

DETAILED DESCRIPTION OF PREFERRED EMBODIMENT(S)

Description will be made below on an exemplary embodiment(s) of the invention.
Arrangement of Organic EL Device
First of all, arrangement(s) of an organic EL device will be described below.
Representative arrangement examples of an organic EL device are as follows:
(1) anode/emitting layer/cathode;
(2) anode/hole injecting layer/emitting layer/cathode;
(3) anode/emitting layer/electron injecting•transporting layer/cathode;
(4) anode/hole injecting layer/emitting layer/electron injecting•transporting layer/cathode;
(5) anode/organic semiconductor layer/emitting layer/cathode;
(6) anode/organic semiconductor layer/electron blocking layer/emitting layer/cathode;
(7) anode/organic semiconductor layer/emitting layer/adhesion improving layer/cathode;
(8) anode/hole injecting•transporting layer/emitting layer/electron injecting•transporting layer/cathode;
(9) anode/insulating layer/emitting layer/insulating layer/cathode;
(10) anode/inorganic semiconductor layer/insulating layer/emitting layer/insulating layer/cathode;
(11) anode/organic semiconductor layer/insulating layer/emitting layer/insulating layer/cathode;
(12) anode/insulating layer/hole injecting•transporting layer/emitting layer/insulating layer/cathode; and
(13) anode/insulating layer/hole injecting•transporting layer/emitting layer/electron injecting•transporting layer/cathode.

While the arrangement (8) is preferably used among the above, the arrangement of the invention is not limited to the above arrangements.

FIG. 1 schematically shows an exemplary arrangement of an organic EL device according to an exemplary embodiment of the invention.

An organic EL device 1 includes a transparent substrate 2, an anode 3, a cathode 4 and an organic thin-film layer 10 disposed between the anode 3 and the cathode 4.

The organic thin-film layer 10 includes a phosphorescent-emitting layer 5 containing a phosphorescent host as a host material and a phosphorescent dopant as a phosphorescent material. A layer such as a hole injecting/transporting layer 6 may be provided between the phosphorescent-emitting layer 5 and the anode 3 while a layer such as an electron injecting/transporting layer 7 may be provided between the phosphorescent-emitting layer 5 and the cathode 4.

In addition, an electron blocking layer may be provided to the phosphorescent-emitting layer 5 adjacently to the anode 3 while a hole blocking layer may be provided to the phosphorescent-emitting layer 5 adjacently to the cathode 4.

With this arrangement, electrons and holes can be trapped in the phosphorescent-emitting layer 5, thereby enhancing probability of exciton generation in the phosphorescent-emitting layer 5.

It should be noted that a "fluorescent host" and a "phosphorescent host" herein respectively mean a host combined with a fluorescent dopant and a host combined with a phosphorescent dopant, and that a distinction between the fluorescent host and phosphorescent host is not unambiguously derived only from a molecular structure of the host in a limited manner.

In other words, the fluorescent host herein means a material for forming a fluorescent-emitting layer containing a fluorescent dopant, and does not mean a host that is only usable as a host of a fluorescent-emitting material.

Likewise, the phosphorescent host herein means a material for forming a phosphorescent-emitting layer containing a phosphorescent dopant, and does not mean a host that is only usable as a host of a phosphorescent material.

It should also be noted that the "hole injecting/transporting layer (or hole injecting-transporting layer)" herein means "at least one of hole injecting layer and hole transporting layer" while the "electron injecting/transporting layer (or electron injecting transporting layer)" herein means "at least one of electron injecting layer and electron transporting layer".
Transparent Substrate The organic EL device 1 according to the exemplary embodiment is formed on a light-transmissive substrate. The light-transmissive substrate, which supports the organic EL device, is preferably a smooth and flat substrate that transmits 50% or more of light in a visible region of 400 nm to 700 nm.

The light-transmissive substrate is exemplarily a glass plate, a polymer plate or the like.

For the glass plate, materials such as soda-lime glass, barium/strontium-containing glass, lead glass, aluminosilicate glass, borosilicate glass, barium borosilicate glass and quartz can be used.

For the polymer plate, materials such as polycarbonate, acryl, polyethylene terephthalate, polyether sulfide and polysulfone can be used.

Anode and Cathode

The anode of the organic EL device 1 is used for injecting holes into the hole injecting layer, the hole transporting layer or the emitting layer. It is effective that the anode has a work function of 4.5 eV or more.

Exemplary materials for the anode are alloys of indium-tin oxide (ITO), tin oxide (NESA), indium zinc oxide, gold, silver, platinum and copper.

The anode may be made by forming a thin film from these electrode materials through a method such as vapor deposition or sputtering.

When light from the emitting layer is to be emitted through the anode as in this exemplary embodiment, the anode preferably transmits more than 10% of the light in the visible region. Sheet resistance of the anode is preferably several hundreds Ω/square or lower. Although depending on the material of the anode, the thickness of the anode is typically in a range of 10 nm to 1 μm, and preferably in a range of 10 nm to 200 nm.

The cathode is preferably formed of a material with smaller work function in order to inject electrons into the electron injecting layer, the electron transporting layer or the emitting layer.

Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, and alloy of magnesium and silver.

Like the anode, the cathode may be made by forming a thin film from the above materials through a method such as vapor deposition or sputtering. In addition, the light may be emitted through the cathode.

Emitting Layer

The emitting layer of the organic EL device 1 has functions as follows, namely:

(1) an injecting function: a function for accepting, when an electrical field is applied, the holes injected by the anode or the hole injecting layer, or the electrons injected by the cathode or the electron injecting layer;

(2) a transporting function: a function for transporting injected electric charges (the electrons and the holes) by the force of the electrical field; and (3) an emitting function: a function for providing a condition for recombination of the electrons and the holes to emit light.

Injectability of the holes may differ from that of the electrons and transporting capabilities of the hole and the electrons (represented by mobilities of the holes and the electrons) may differ from each other.

As a method of forming the emitting layer, known methods such as vapor deposition, spin coating and an LB method may be employed.

The emitting layer is preferably a molecular deposit film.

The molecular deposit film means a thin film formed by depositing a material compound in gas phase or a film formed by solidifying a material compound in a solution state or in liquid phase. The molecular deposit film is typically distinguished from a thin film formed by the LB method (molecular accumulation film) by differences in aggregation structures, higher order structures and functional differences arising therefrom.

The emitting layer can be formed from a thin film formed by spin coating or the like, the thin film being formed from a solution prepared by dissolving a binder (e.g. a resin) and a material compound in a solvent.

According to the exemplary embodiment, an organic EL device includes: a cathode; an anode; and a single-layered or multilayered organic thin-film layer provided between the cathode and the anode and including at least one emitting layer, in which at least one layer of the organic thin-film layer contains at least one phosphorescent material and at least one organic EL device material of the exemplary embodiment (described later). In addition, at least one of the emitting layer(s) preferably contains the organic EL device material of the exemplary embodiment and at least one phosphorescent material.

Organic EL Device Material

Specifically, an organic EL device material according to the exemplary embodiment includes at least a unit including 3,5-biscarbazolylphenyl group, a unit including 4-carbazolylphenyl group, and a compound including a unit including a nitrogen-containing aromatic heterocyclic ring bonding the unit including 3,5-biscarbazolylphenyl group and the unit including 4-carbazolylphenyl group.

The unit including 3,5-biscarbazolylphenyl group is represented by the following formula (U1).

In the formula:
a represents an integer of 0 to 3;
$Y^1$ represents a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms; and
when a is an integer of 2 or more, $Y^1$ may be the same or different.

The unit including 4-carbazolylphenyl group is represented by the following formula (U2).

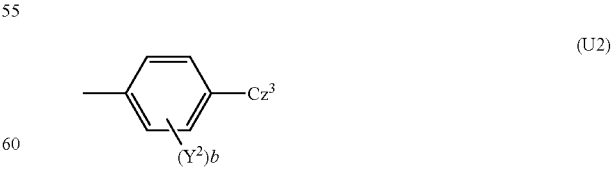

In the formula:
b represents an integer of 0 to 4;
$Y^2$ represents a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms; and when b is an integer of 2 or more, $Y^2$ may be the same or different.

Preferably, $Cz^1$, $Cz^2$ and $Cz^3$ each independently represent a monovalent residue obtained by removing any one of $Rx_1$ to $Rx_8$ constituting $Z_1$ to $Z_8$ in the following formula (U3) or a monovalent residue obtained by removing $Z_9$. Particularly, a monovalent residue obtained by removing $Rx_3$, $Rx_7$ or $Z_9$ is preferable.

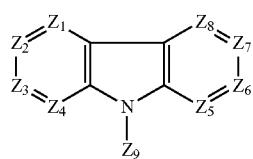

(U3)

In the formula:

$Z_1$ to $Z_8$ each represent $CRx_1$ to $CRx_8$ or N;

$Rx_1$ to $Rx_8$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms;

$Z_1$ and $Z_2$, $Z_2$ and $Z_3$, $Z_3$ and $Z_4$, $Z_5$ and $Z_6$, $Z_6$ and $Z_7$, and $Z_7$ and $Z_8$ may form rings, respectively; and $Z_9$ represents a hydrogen atom, a substituted or unsubstituted and linear, branched or cyclic alkyl group having 1to 20carbon atoms, branched or cyclic haloalkyl group having 1to 20carbon atoms, a substituted or unsubstituted aromatic hydrocarbon group having 6 to 30 ring carbon atoms, or a substituted or unsubstituted aromatic heterocyclic group having 2 to 10 ring carbon atoms.

In the exemplary embodiment, the compound unit including the nitrogen-containing aromatic heterocyclic ring is a divalent or more group of a monocyclic nitrogen-containing aromatic heterocyclic compound and a fused polycyclic nitrogen-containing aromatic heterocyclic compound.

Preferably, the organic EL device material of the exemplary embodiment is represented by, in particular, the following formula (7).

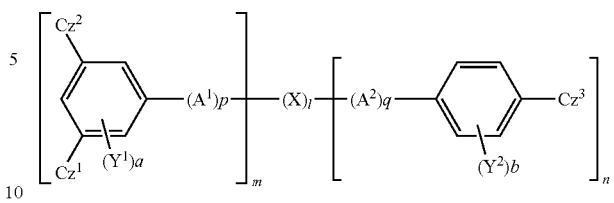

(7)

In the formula:

$A^1$ and $A^2$ each represent a substituted or unsubstituted aromatic hydrocarbon group having 6 to 60 ring carbon atoms;

$Cz^1$ to $Cz^3$ each independently represent a substituted or unsubstituted carbazolyl group and may be mutually the same or different;

X represents a substituted or unsubstituted nitrogen-containing aromatic heterocyclic ring;

$Y^1$ and $Y^2$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms;

a represents an integer of 0 to 3 and b represents an integer of 0 to 4;

l, m and n each independently represent an integer of 1 to 3;

when l is 2 or more, X may be the same or different;

m represents an integer of 1 or 2 as the number of substituent(s) being directly bonded to X and being represented by the following formula (8);

when m is 2, structures represented by the formula (8) may be the same or different;

n represents an integer of 1 or 2 as the number of substituent(s) being directly bonded to X and being represented by the following formula (9);

when n is 2, structures represented by the formula (9) may be the same or different;

p and q each independently represent an integer of 0 to 3;

when p is 2 or more, $A^1$ may be the same or different; and when q is 2 or more, $A^2$ may be the same or different.

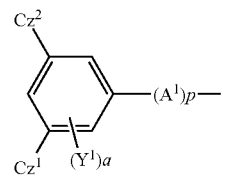

(8)

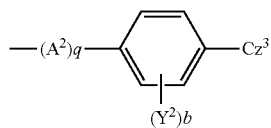
(9)

In the formula (7), examples of the nitrogen-containing aromatic ring are a pyrrole ring, pyrazole ring, imidazole ring, triazole ring, pyridine ring, pyrimidine ring, pyridazine ring, pyrazine ring, triazine ring, indole ring, indazole ring, benzimidazole ring, quinoline ring, isoquinoline ring, cinnoline ring, quinoxaline ring and imidazopyridine ring. Among the above, preferable are a pyrazole ring, imidazole ring, pyridine ring, pyrimidine ring, pyridazine ring, pyrazine ring, triazine ring, indole ring and imidazopyridine ring, and more preferable are a pyridine ring, pyrimidine ring, triazine ring and indole ring.

Additionally, the formula (7) is preferably shown as one of the following formulae (7-A) to (7-C).

(7-A)

(7-B)

(7-C)

More preferably, l=1, m=1 and n=1, so that the formula (7) is shown as the following formula (7-D).

(7-D)

More preferably, X in the formula (7-D) is a substituted or unsubstituted pyrimidine ring.

More preferably, the formula (7) is shown as the following formula (10).

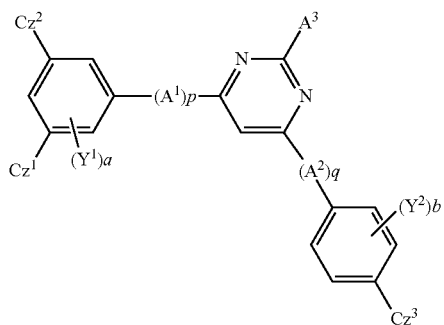
(10)

In the formula, $A^3$ represents a substituted or unsubstituted aromatic hydrocarbon group having 6 to 30 ring carbon atoms.

In the formula (7), (7-A), (7-B), (7-C), (7-D) or (10), $A^1$ or $A^2$ is preferably a benzene ring.

In the formula (7), (7-A), (7-B), (7-C), (7-D) or (10), the benzene ring may include substituents $Y^1$ and $Y^2$ or may be unsubstituted (i.e., a=0 and b=0).

In the formula (7), (7-A), (7-B), (7-C), (7-D) or (10), when $A^2$ is a substituted or unsubstituted benzene ring, the benzene ring and X bonded to $A^2$ are preferably in ortho positions or para positions. In particular, when q is equal to 1 or more and $A^2$ is a benzene ring, $A^2$ is preferably a substituted or unsubstituted para-phenylene represented by the following formula.

In the formula (7), (7-A), (7-B), (7-C), (7-D) or (10), q=0 is preferable.

In addition, preferably, each of $Cz^1$ to $Cz^3$ is independently represented by the following formula (11) or (12). Incidentally, in the following formulae, "*" represents a bond position to the benzene ring.

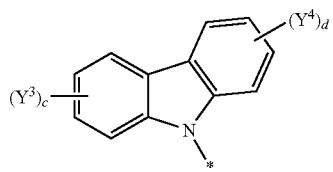
(11)

In the formula (11), $Y^3$ and $Y^4$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon

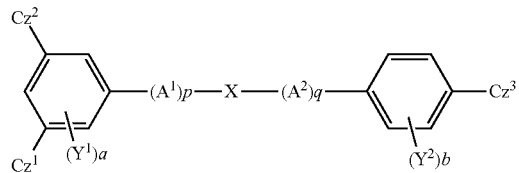

group having 6 to 30 ring carbon atoms, or a substituted or unsubstituted aromatic heterocyclic group having 2 to 10 ring carbon atoms. c and d each independently represent an integer of 1 to 4.

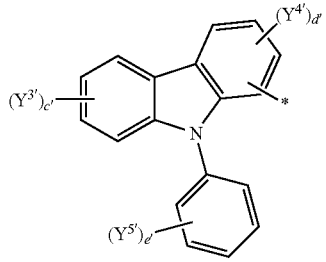

(12)

In the formula (12), $Y^{3\prime}$, $Y^{4\prime}$ and $Y^{5\prime}$ each independently represent a hydrogen atom, a halogen atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms. c' represents an integer of 1 to 4. d' represents an integer of 1 to 3. e' represents an integer of 1 to 5.

In addition, preferably, each of $Cz^1$ to $Cz^3$ is independently represented by the following formula (11a) or (12a).

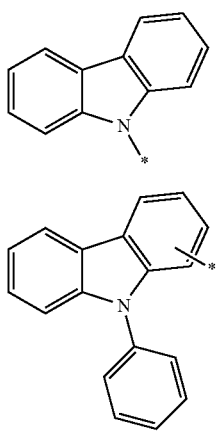

(11a)

(12a)

For $A^1$, $A^2$, $A^3$, $Y^1$ to $Y^4$ and $Y^{3\prime}$ to $Y^{5\prime}$ in the formulae (7) to (12), examples of the linear, branched or cyclic alkyl group having 1 to 20 carbon atoms are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, cyclopentyl group, cyclohexyl group, cyclooctyl group, 3,5-dimethylcyclohexyl group, and 3,3,5,5-tetramethylcyclohexyl group.

The linear, branched or cyclic alkoxy group having 1 to 20 carbon atoms is preferably an alkoxy group having 1 to 6 carbon atoms, examples of which are a methoxy group, ethoxy group, propoxy group, butoxy group, pentyloxy group and hexyloxy group.

An example of the linear, branched or cyclic haloalkyl group having 1 to 20 carbon atoms is a haloalkyl group in which the alkyl group having 1 to 20 carbon atoms is substituted by one or more halogen group(s).

An example of the linear, branched or cyclic haloalkoxy group having 1 to 20 carbon atoms is a haloalkoxy group in which the alkoxy group having 1 to 20 carbon atoms is substituted by one or more halogen group(s).

Examples of the linear, branched or cyclic alkylsilyl group having 1 to 10 carbon atoms are a trimethylsilyl group, triethylsilyl group, tributylsilyl group, dimethylethylsilyl group, dimethylisopropylsilyl group, dimethylpropylsilyl group, dimethylbutylsilyl group, dimethyl-tertiary-butylsilyl group and diethylisopropylsilyl group.

Examples of the arylsilyl group having 6 to 30 carbon atoms are a phenyldimethylsilyl group, diphenylmethylsilyl group, diphenyl-tertiary-butylsilyl group and triphenylsilyl group.

Examples of the aromatic heterocyclic group having 2 to 10 ring carbon atoms are a pyroryl group, pyrazinyl group, pyridinyl group, indolyl group, isoindolyl group, furyl group, benzofuranyl group, isobenzofuranyl group, dibenzofuranyl group, dibenzothiophenyl group, quinolyl group, isoquinolyl group, quinoxalinyl group, carbazolyl group, phenanthrydinyl group, acridinyl group, phenanthrolinyl group, thienyl group, and group formed based on a pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, imidazole ring, benzimidazole ring, pyrane ring and dibenzofuran ring.

Examples of the aromatic hydrocarbon group having 6 to 60 ring carbon atoms are a phenyl group, naphthyl group, phenanthryl group, biphenyl group, terphenyl group, quaterphenyl group, fluoranthenyl group, benzo[b]fluoranthenyl group, triphenylenyl group, phenanthrenyl group, chrysenyl group, benzochrysenyl group, picenyl group, fluorenyl group and binaphthyl group.

Examples of the halogen atom are a fluorine atom, a chlorine atom, a bromine atom and an iodo atom, among which a fluorine atom is preferable.

When X, $A^1$, $A^2$, a benzene ring, $Cz^1$ to $Cz^3$, $Y^1$ to $Y^4$ and $Y^{3\prime}$ to $Y^{5\prime}$ in the formulae (7) to (12) each have one substituent or a plurality of substituents, the substituent(s) is preferably a linear, branched or cyclic alkyl group having 1 to 20 carbon atoms, a haloalkyl group having 1 to 20 carbon atoms, a linear, branched or cyclic alkylsilyl group having 1 to 10 carbon atoms, a cyano group, a halogen atom, an aromatic hydrocarbon group having 6 to 30 ring carbon atoms, or an aromatic heterocyclic group having 2 to 30 ring carbon atoms. Examples of the above groups are the same as those listed in relation to $A^1$, $A^2$, $A^3$, $Y^1$ to $Y^4$ and $Y^{3\prime}$ to $Y^{5\prime}$.

Preferably, the compounds represented by the formulae (7) to (12) are further represented by the following formulae.
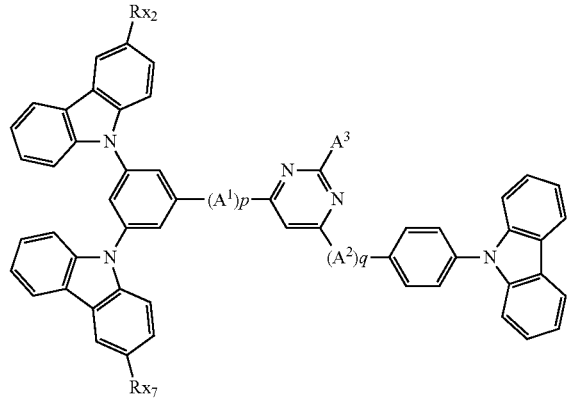
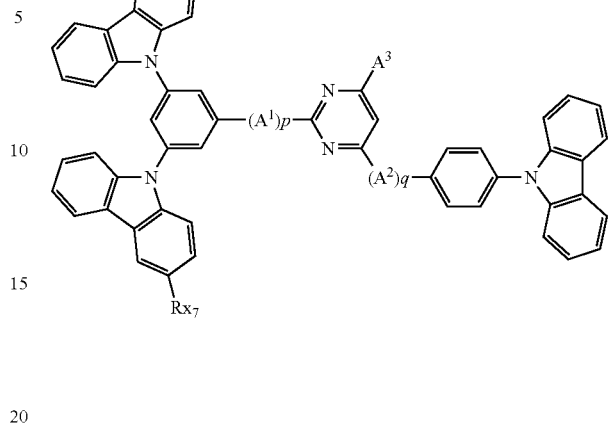
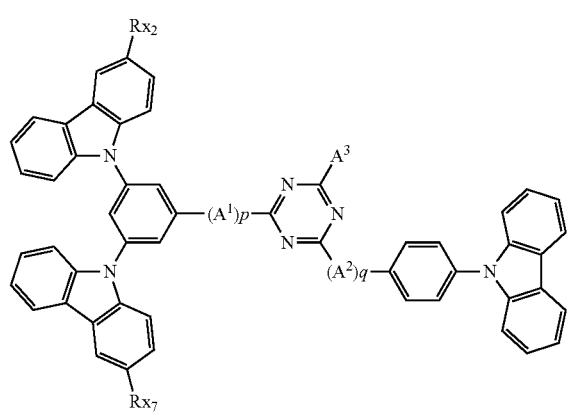
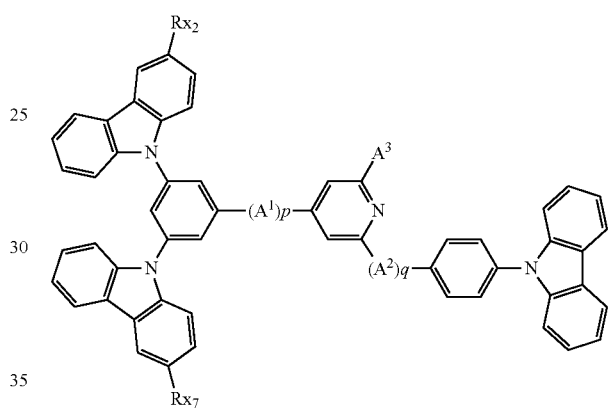
The following are exemplary compounds of the organic EL device material according to the exemplary embodiment of the invention represented by the formulae (7) and (12).
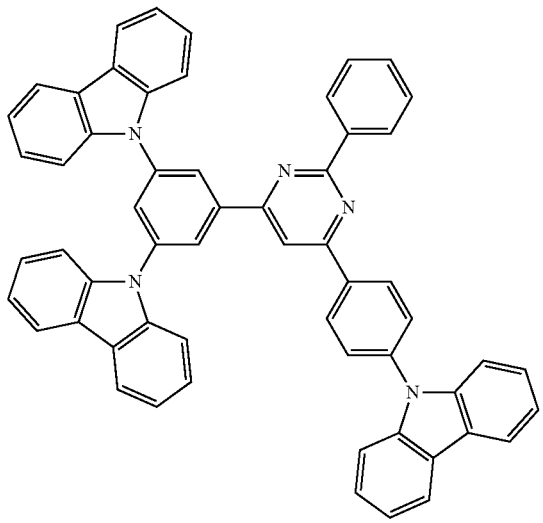
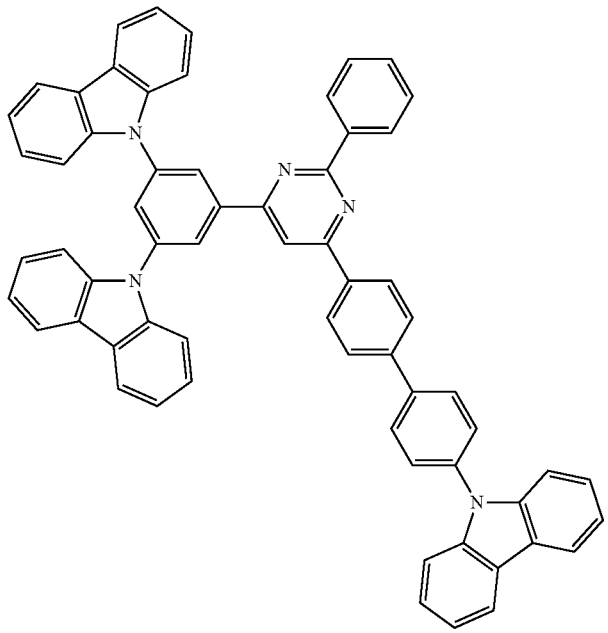

-continued
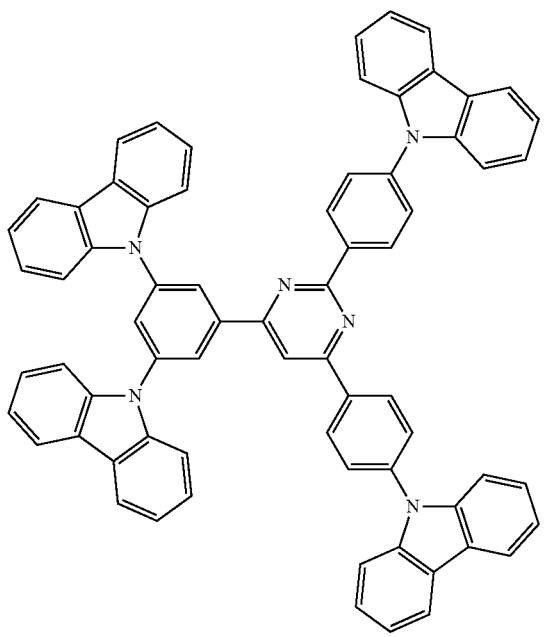
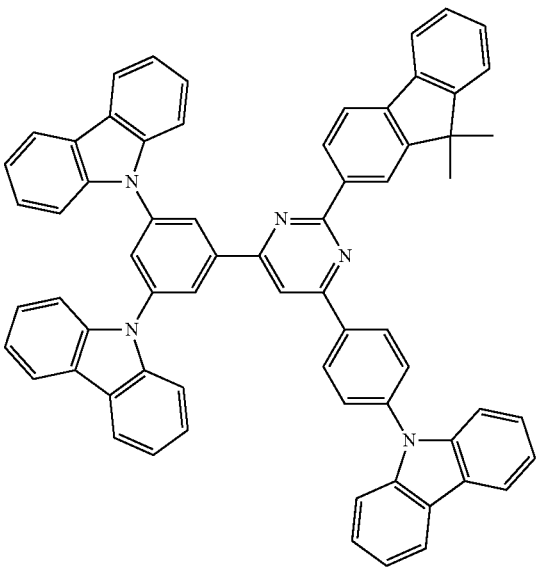
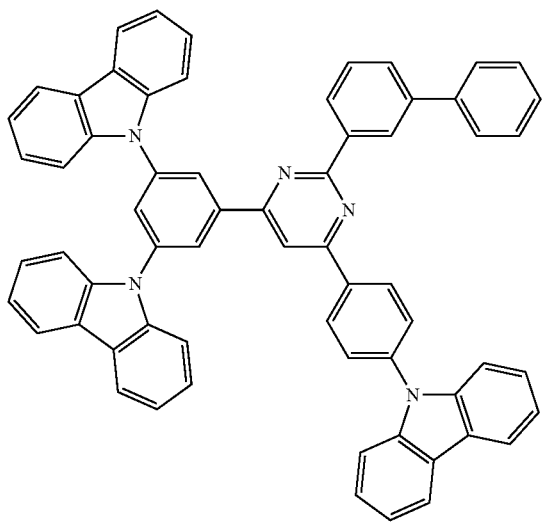
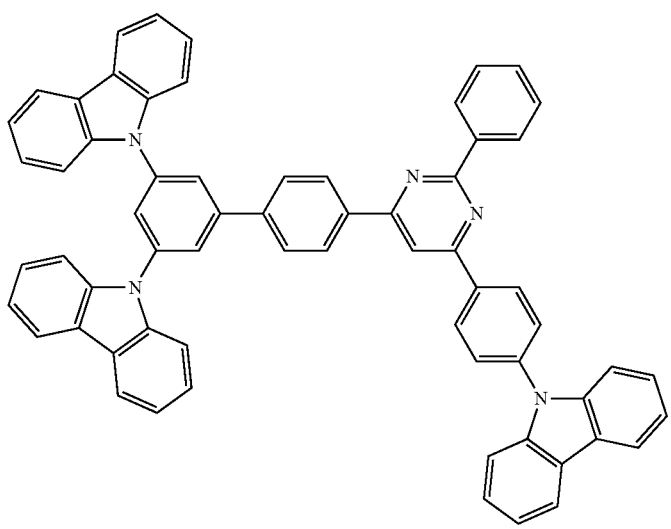

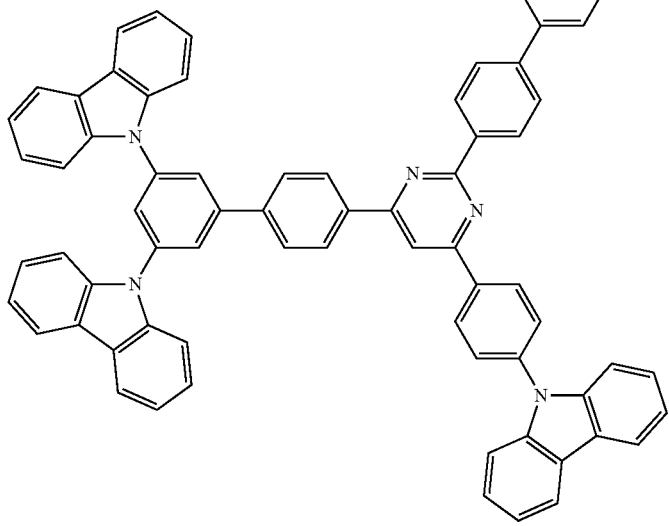
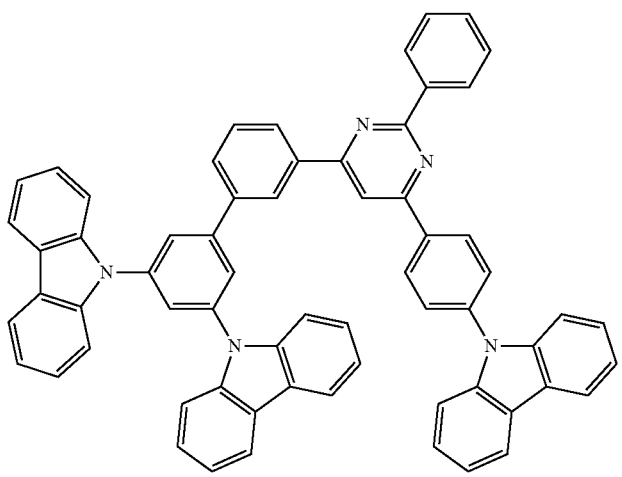
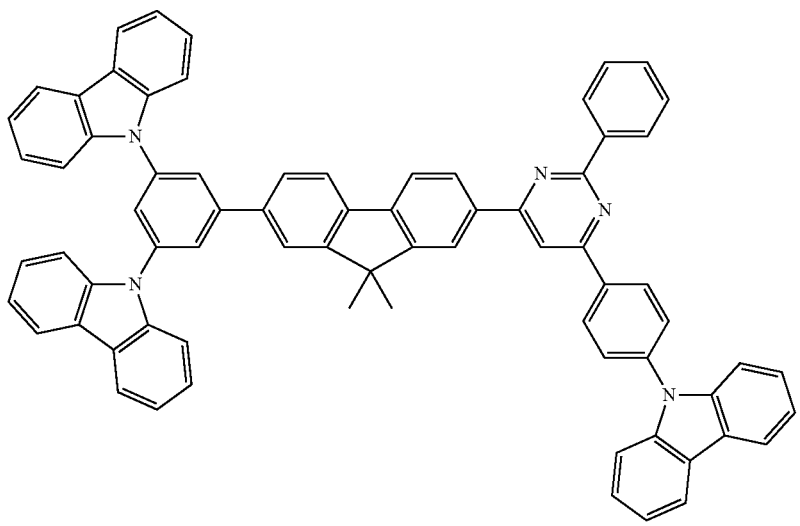

-continued
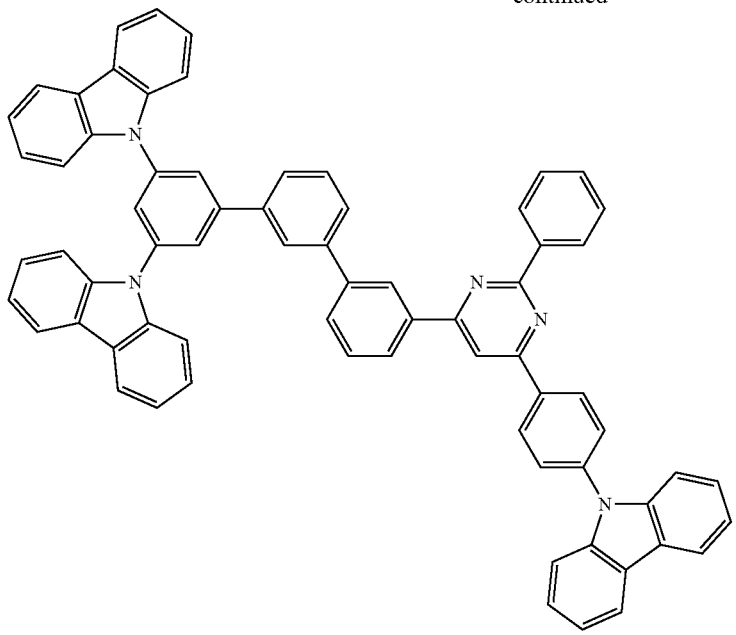
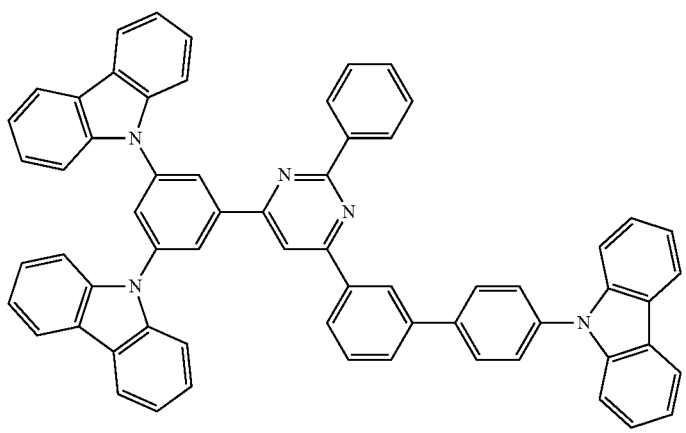
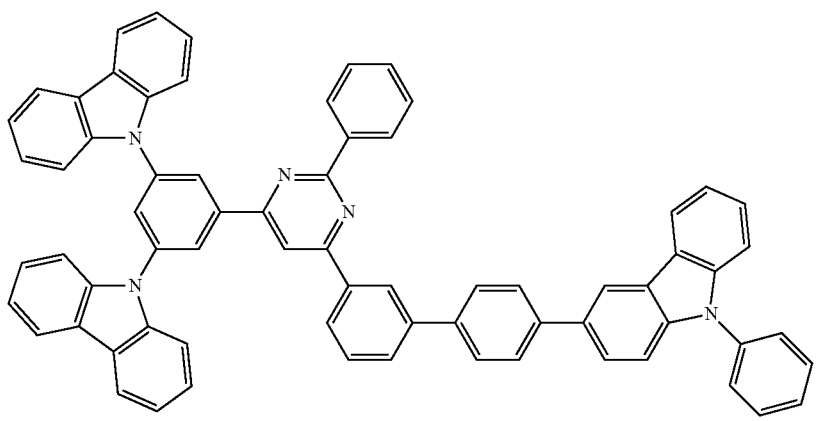

-continued
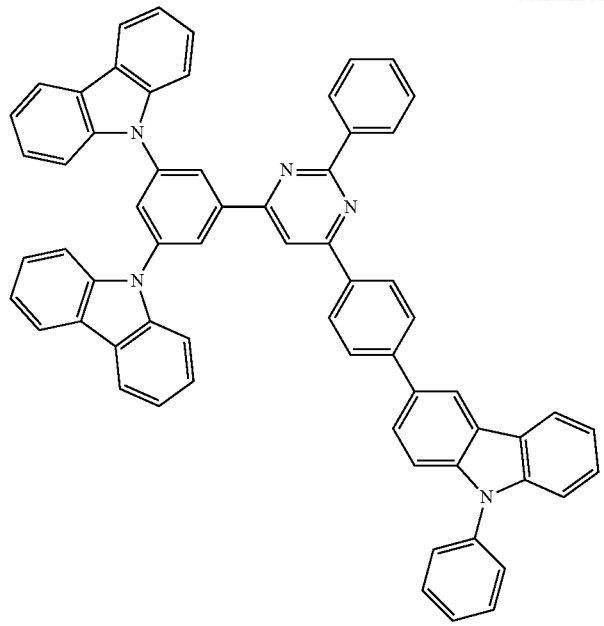
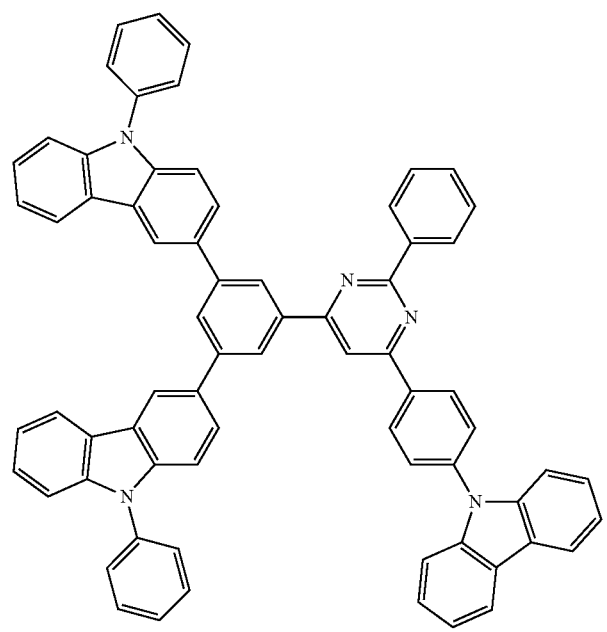

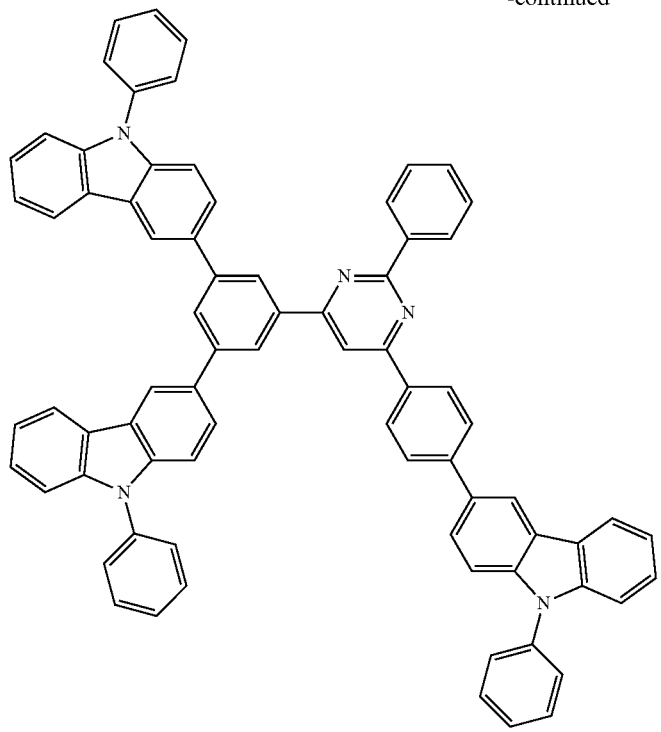
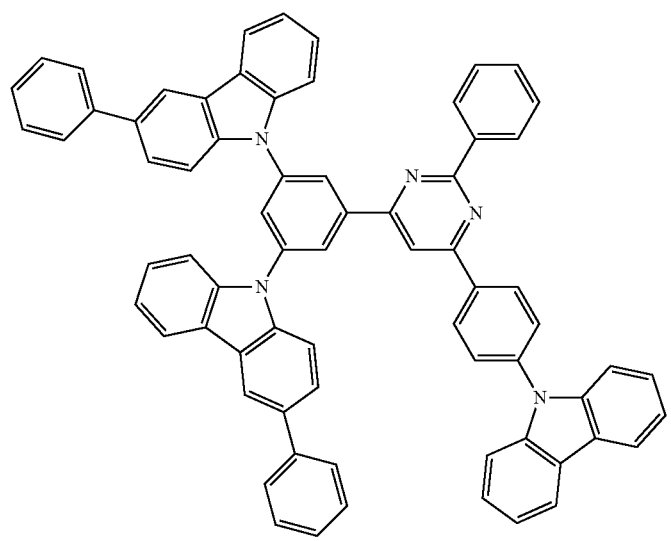

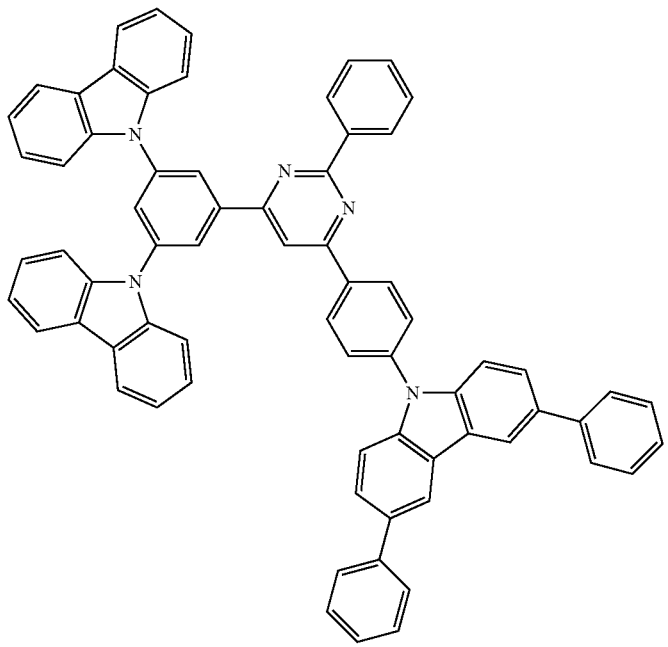
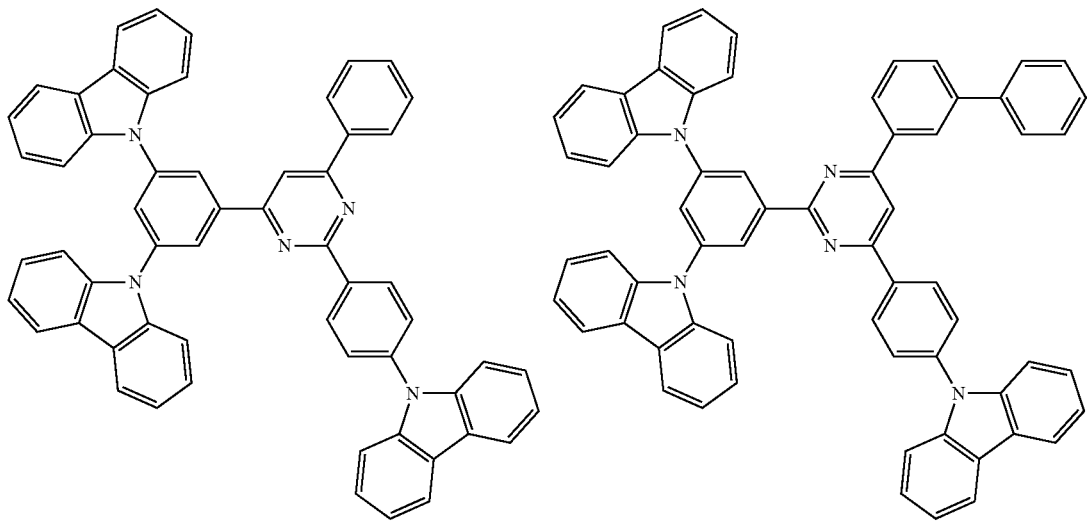
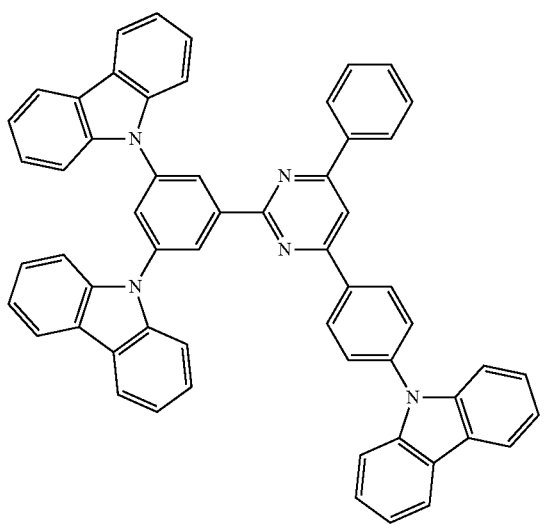

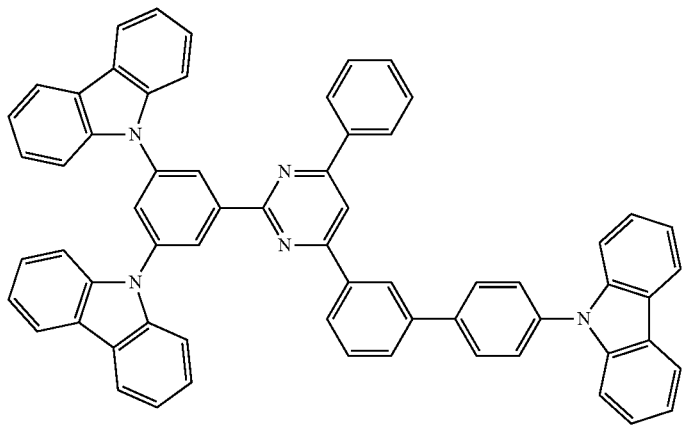
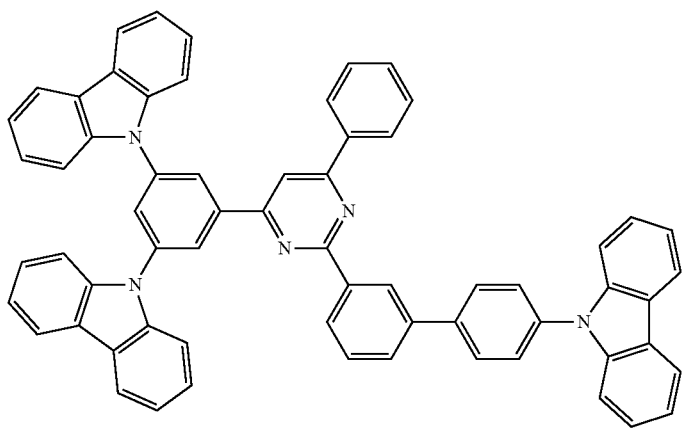
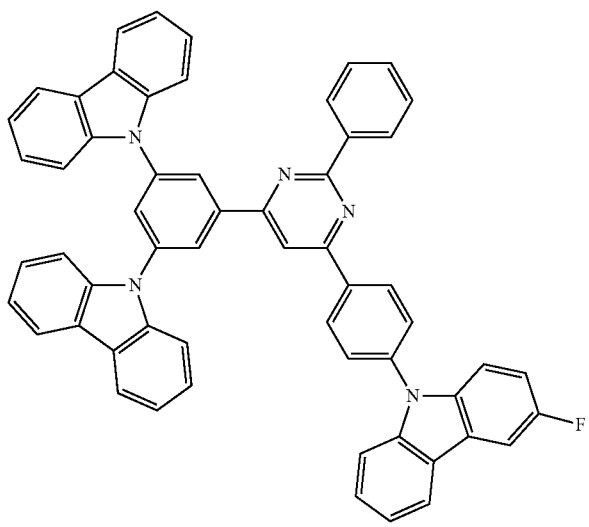

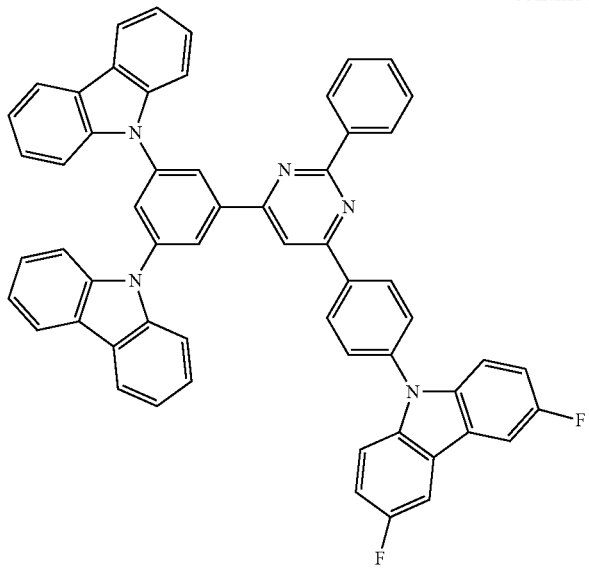
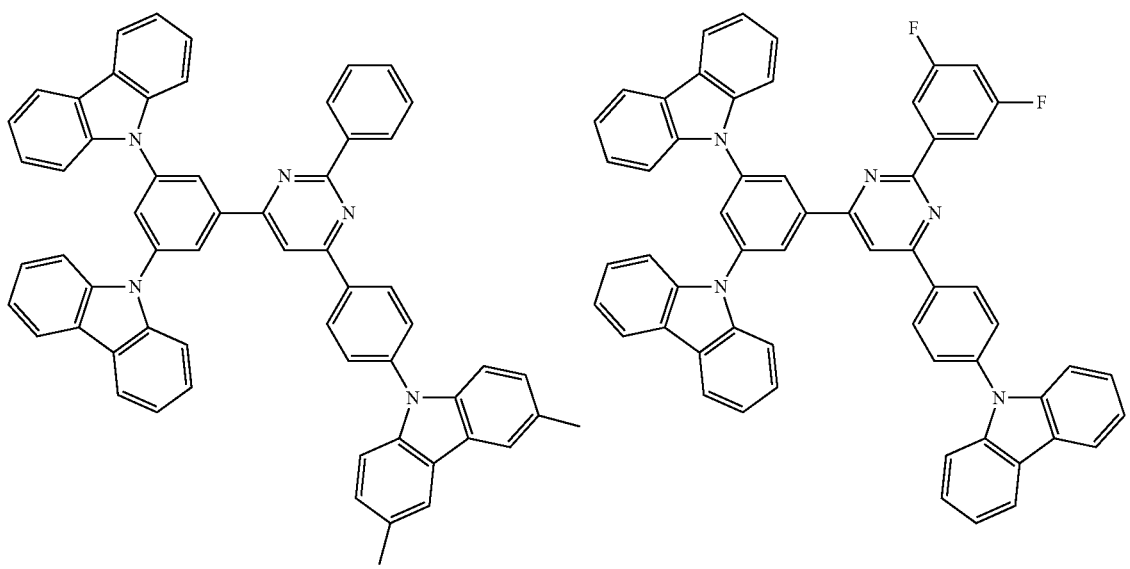
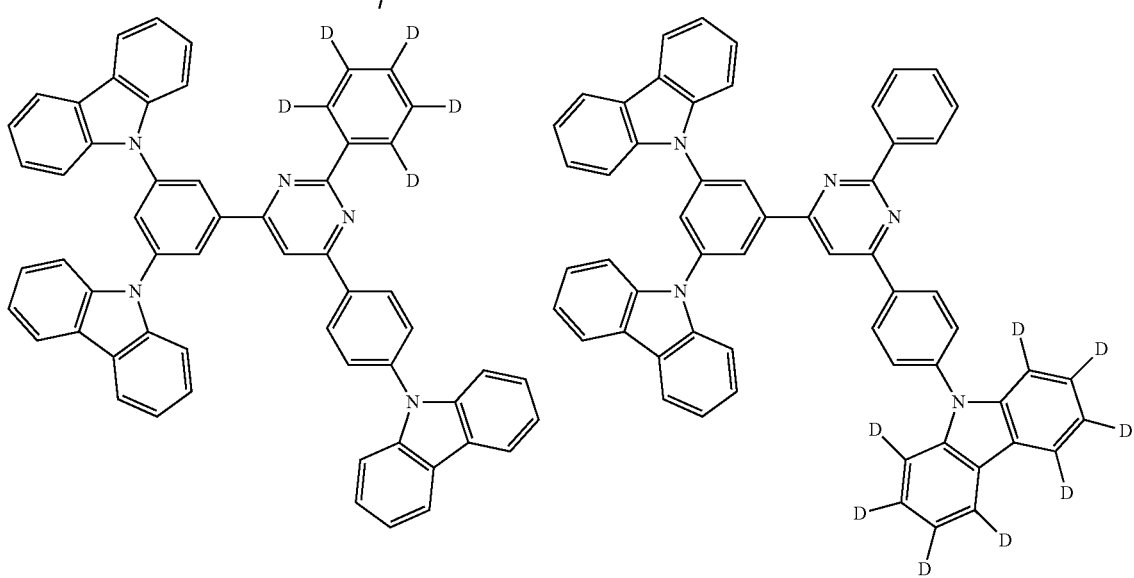

-continued
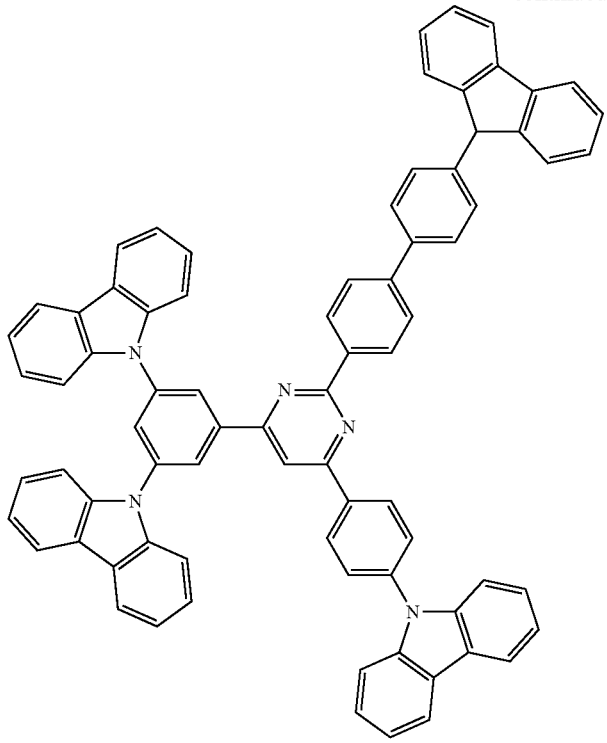
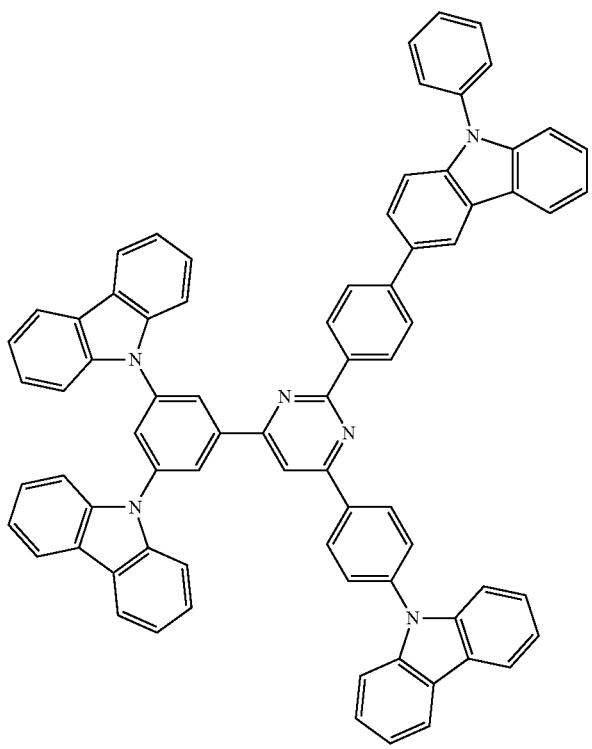

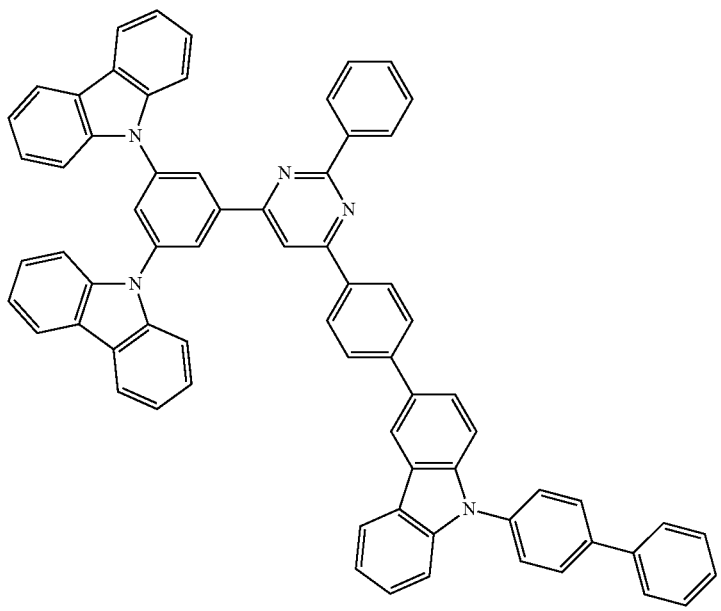 [SMILES: c1ccc(-c2ccc(-n3c4ccccc4c4cc(-c5ccc(-c6cc(-c7cc(-n8c9ccccc9c9ccccc98)cc(-n8c9ccccc9c9ccccc98)c7)nc(-c7ccccc7)n6)cc5)ccc43)cc2)cc1]
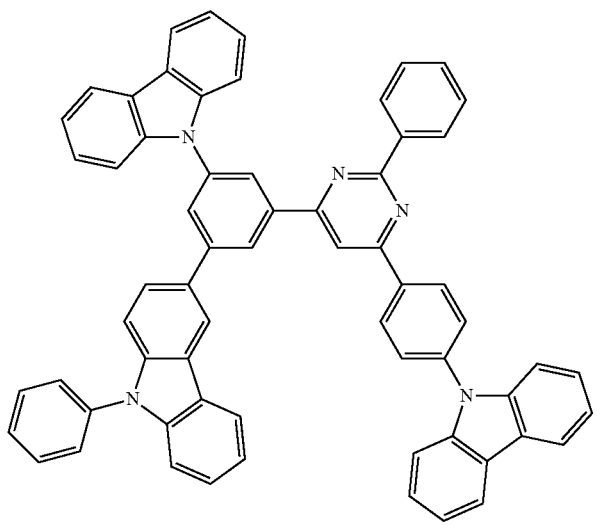
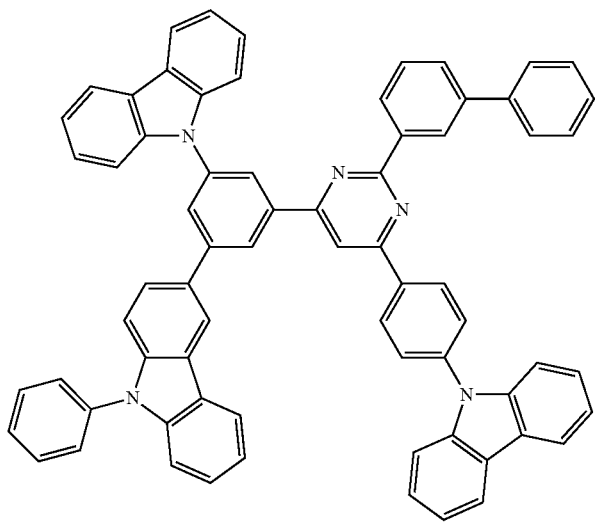

-continued
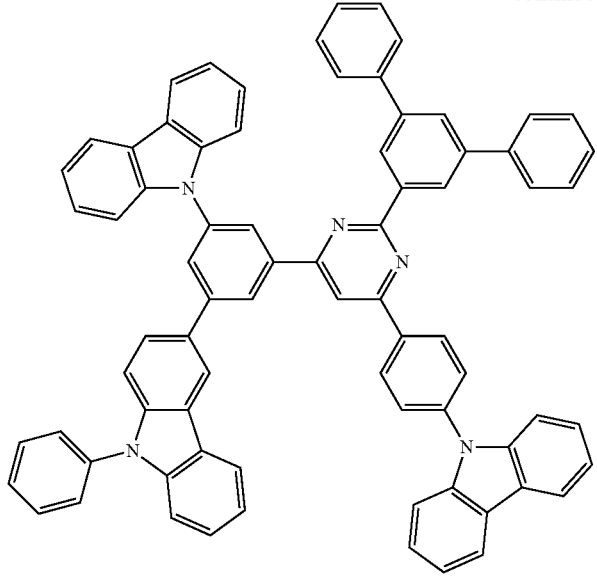
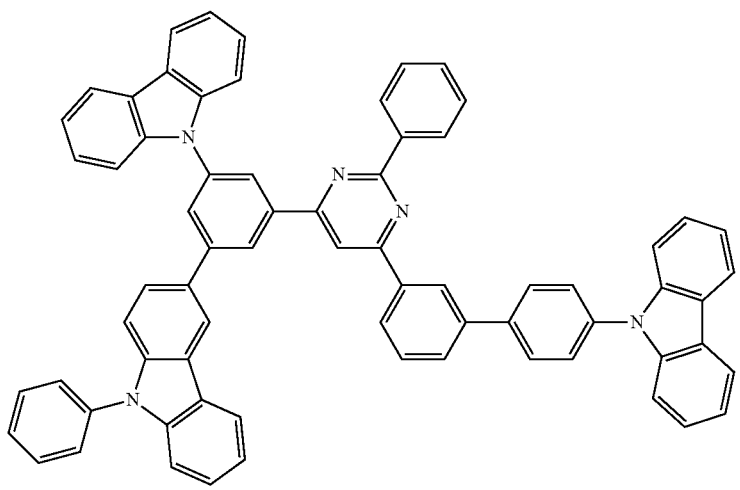
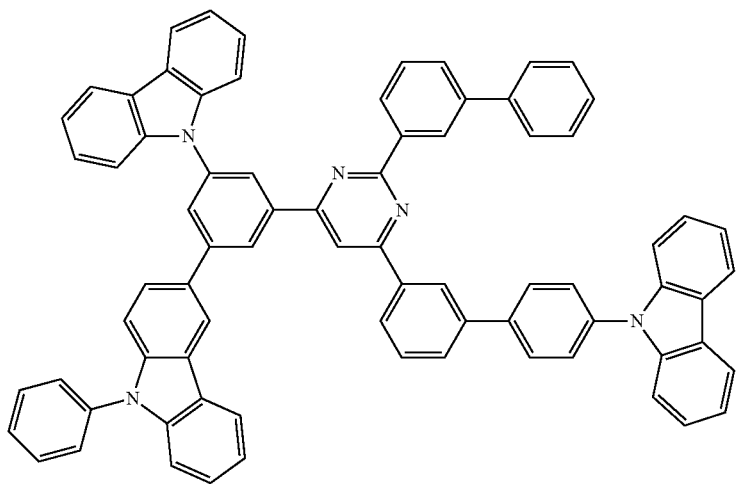

-continued
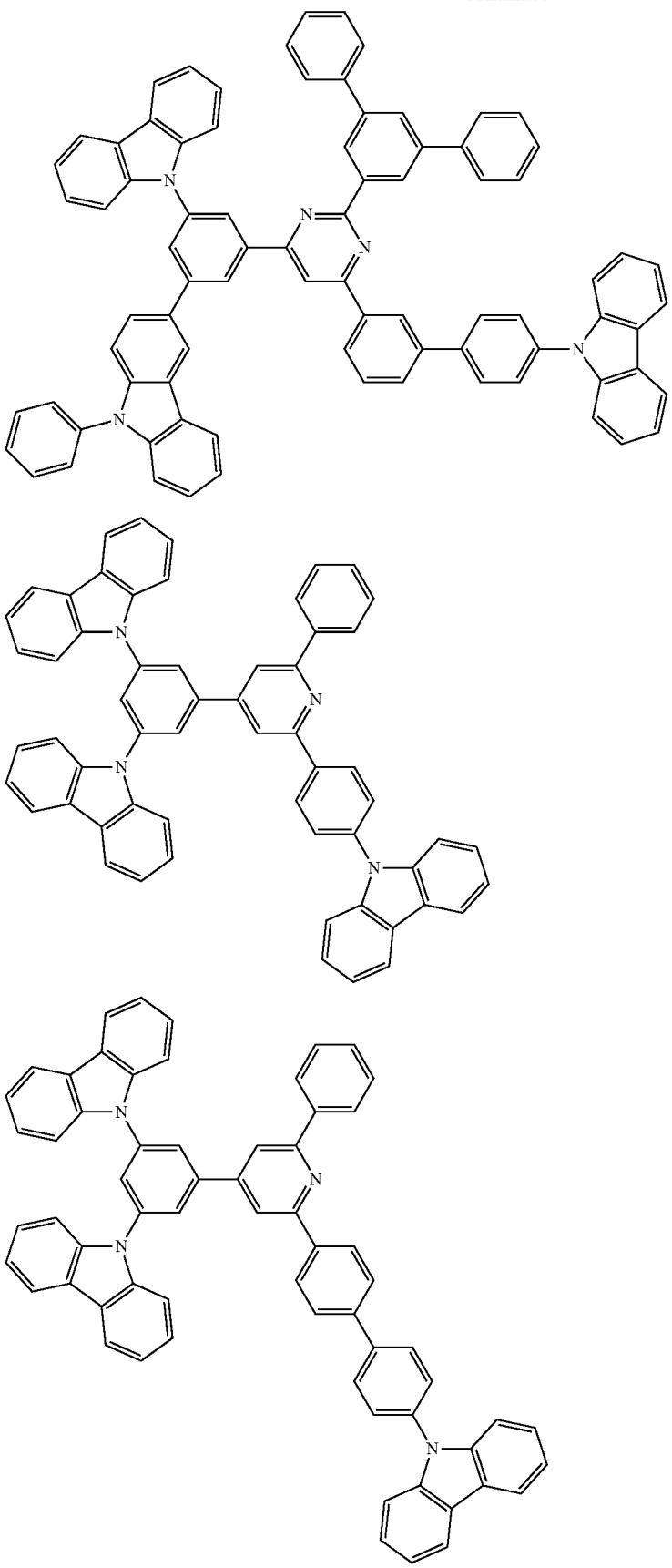

-continued
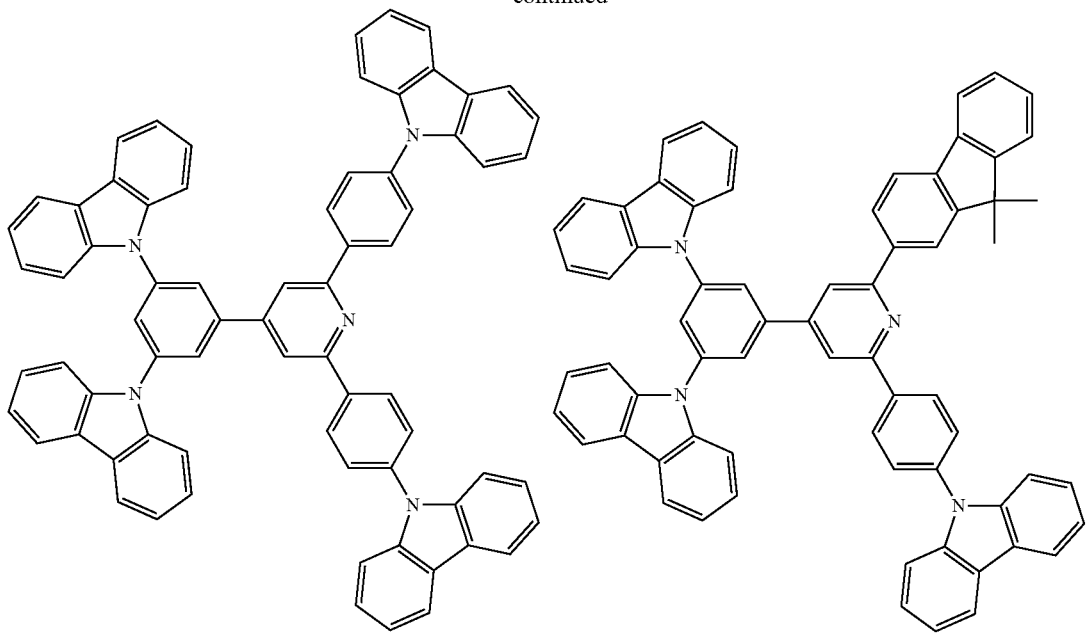
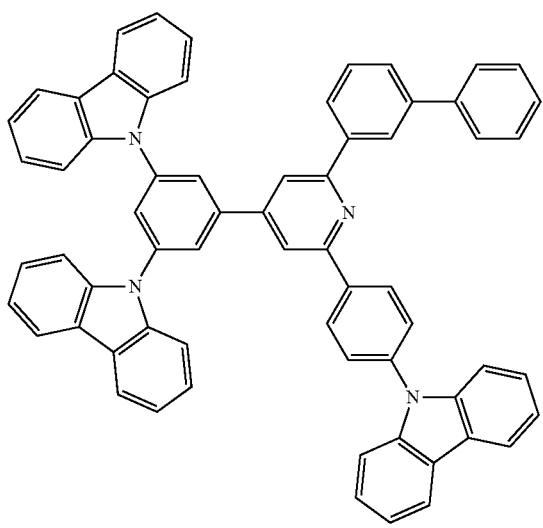
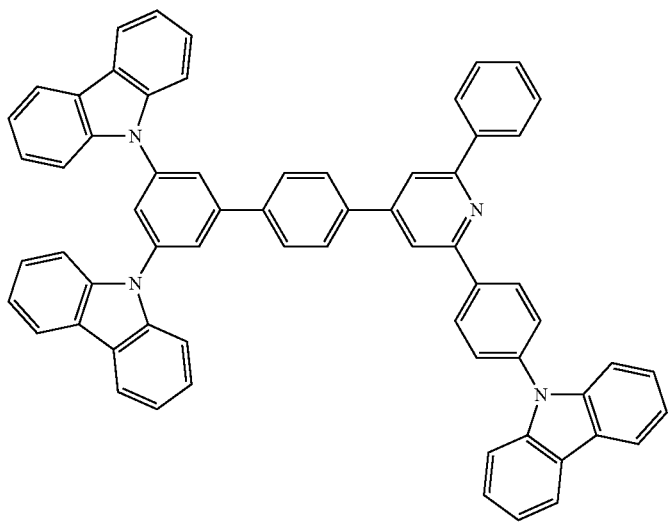

-continued
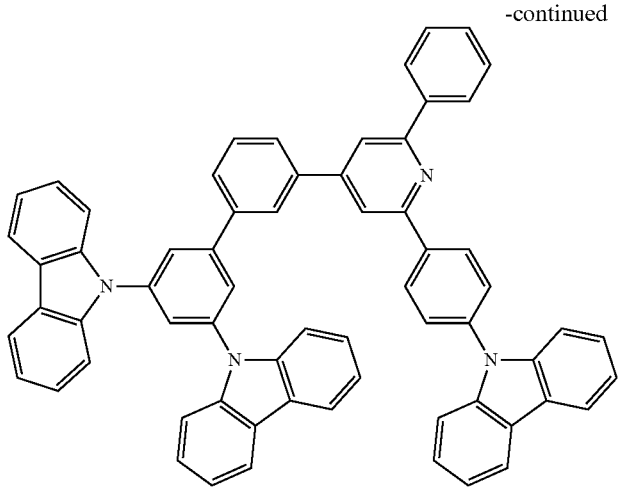
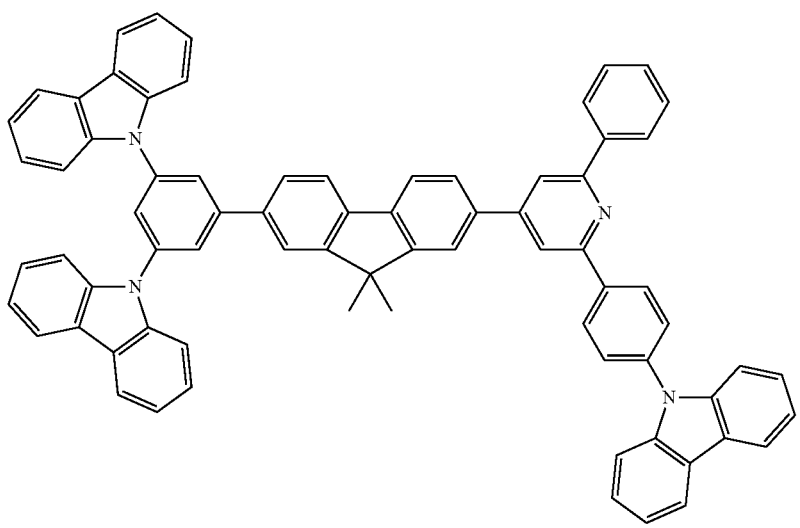
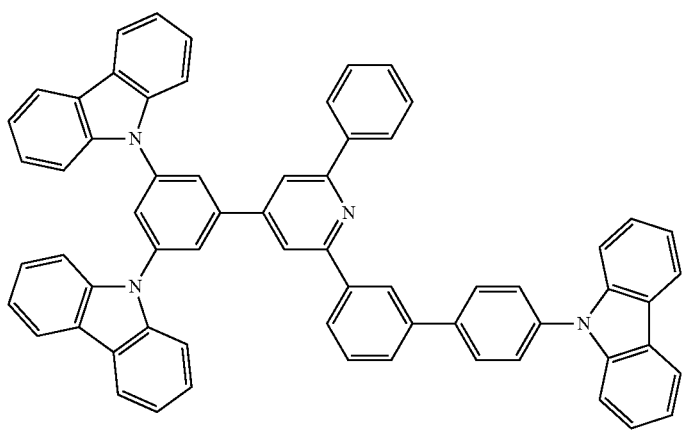

-continued
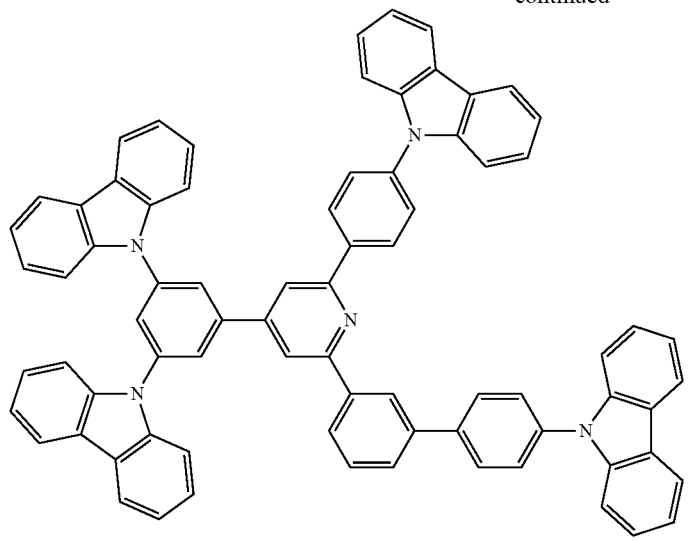
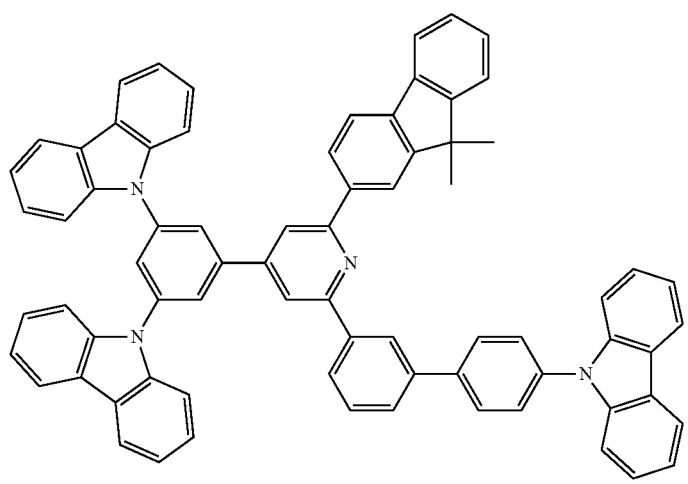
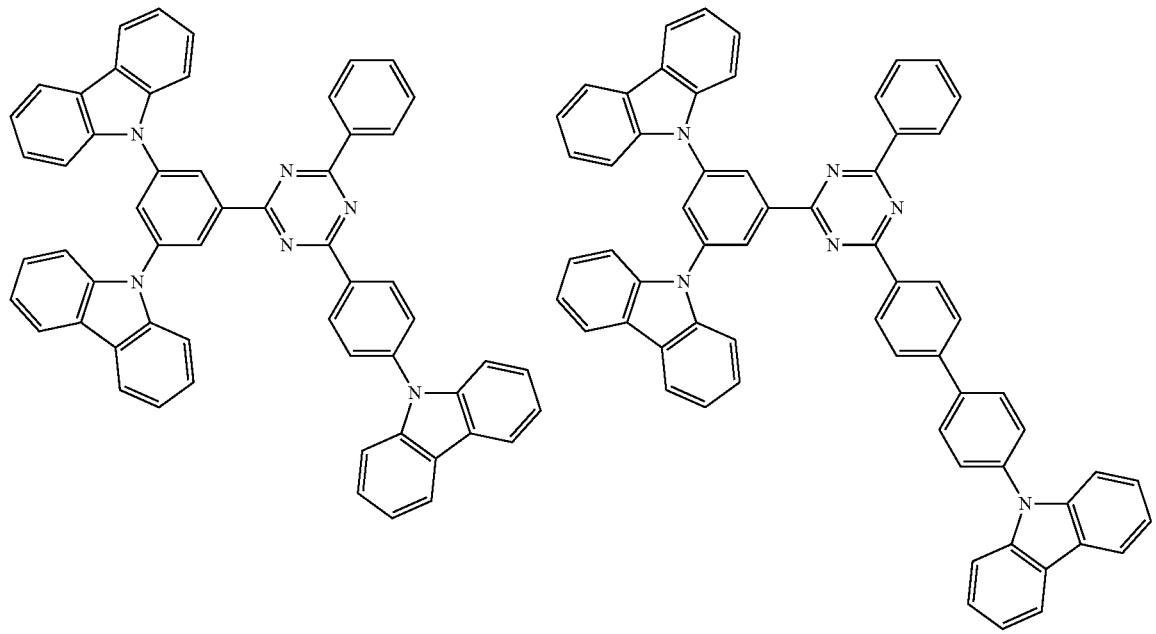

-continued
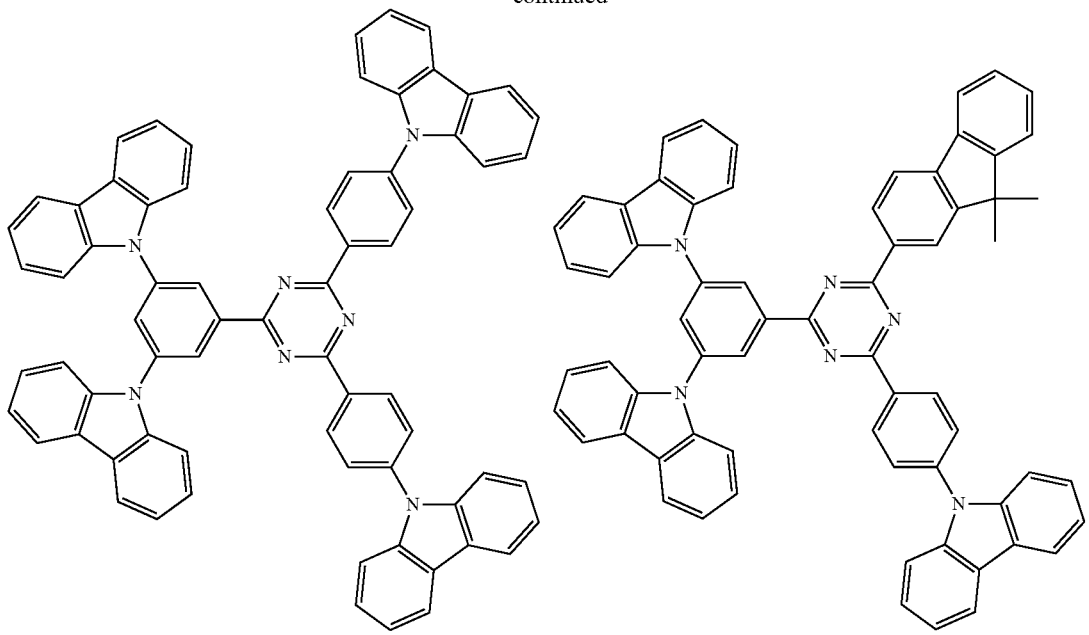
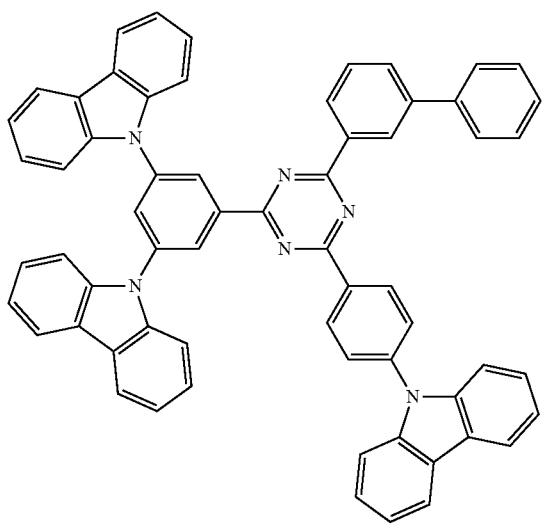
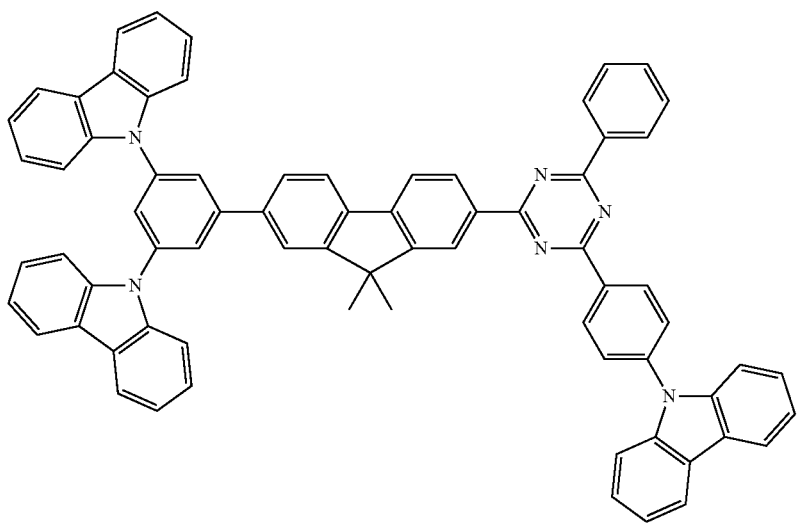

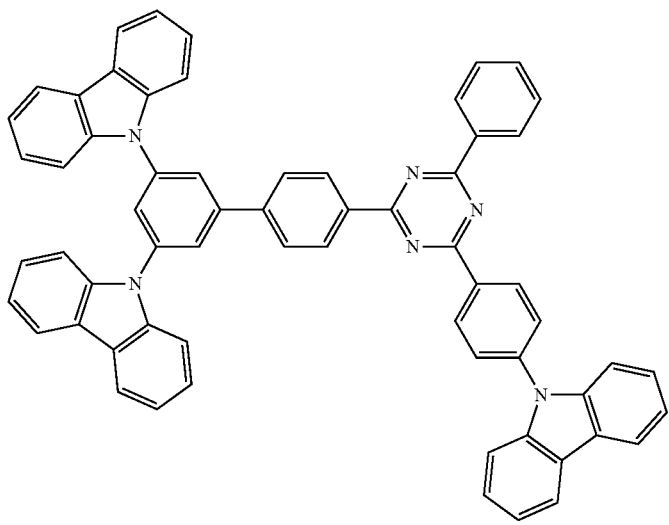
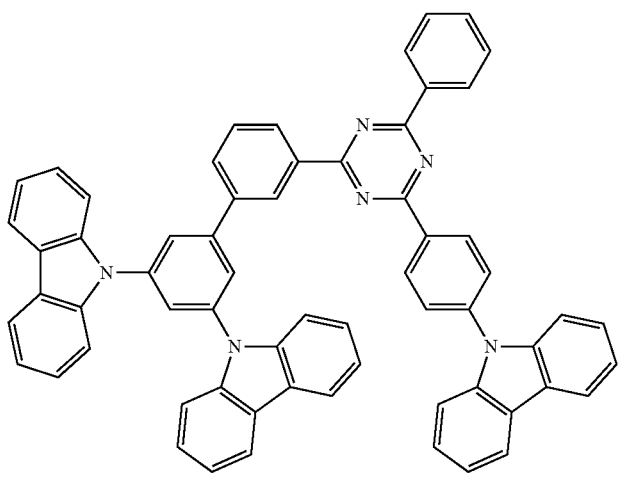
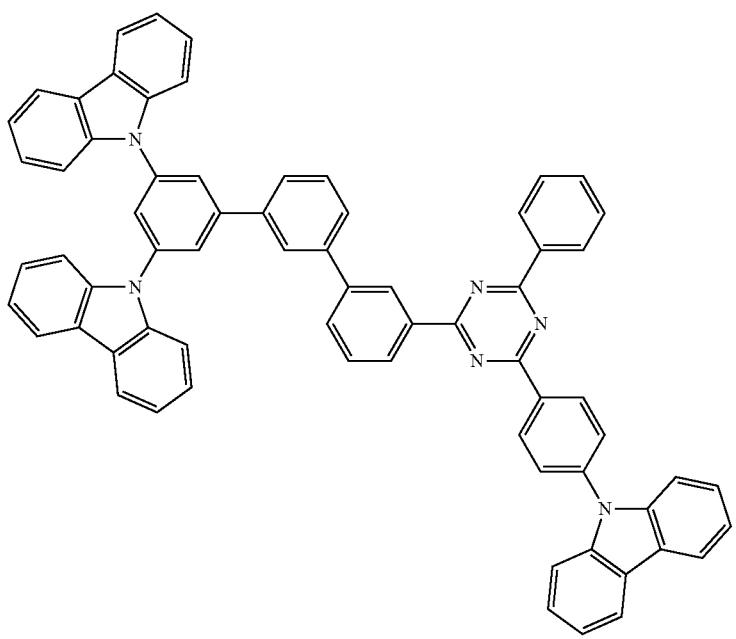

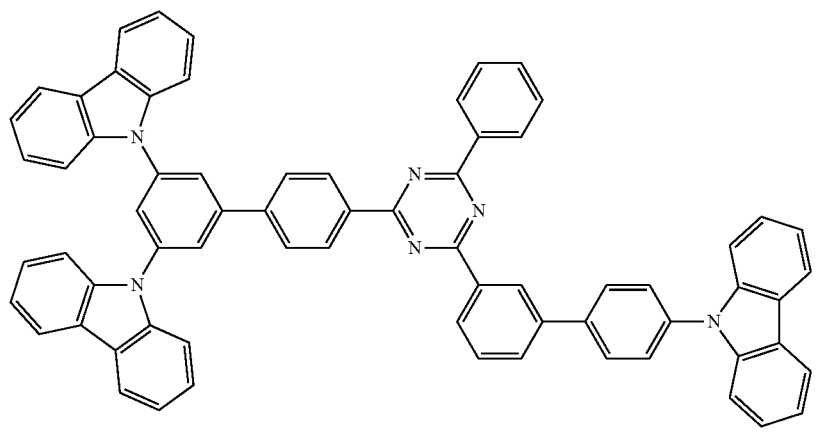
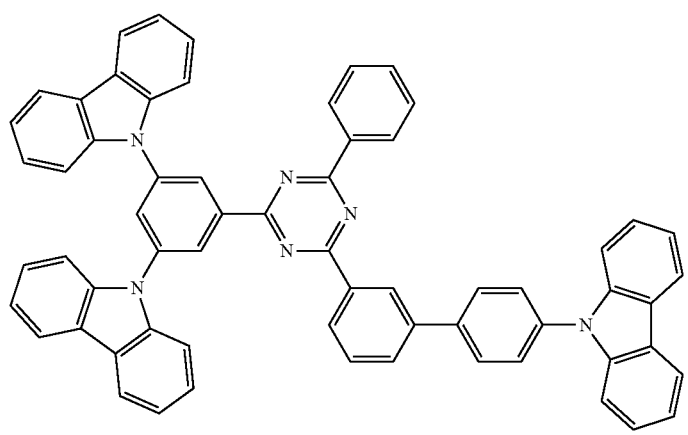
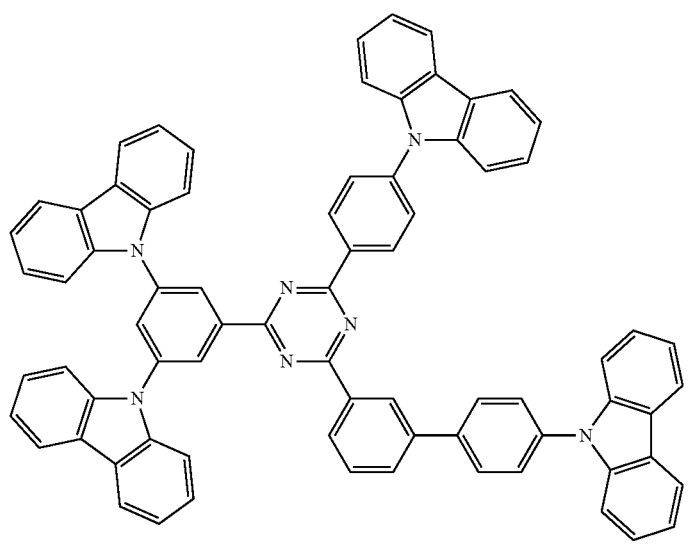

-continued
57
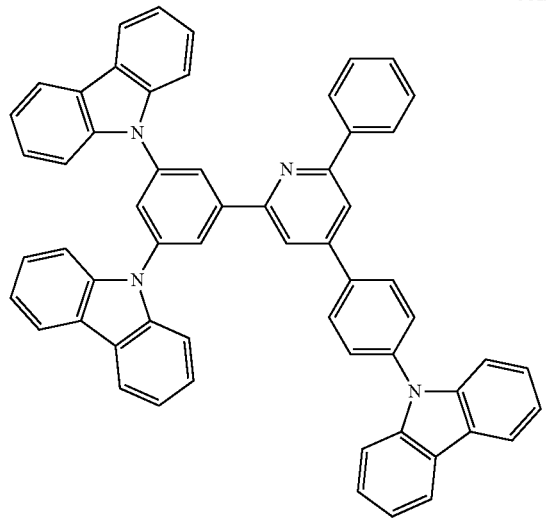
58
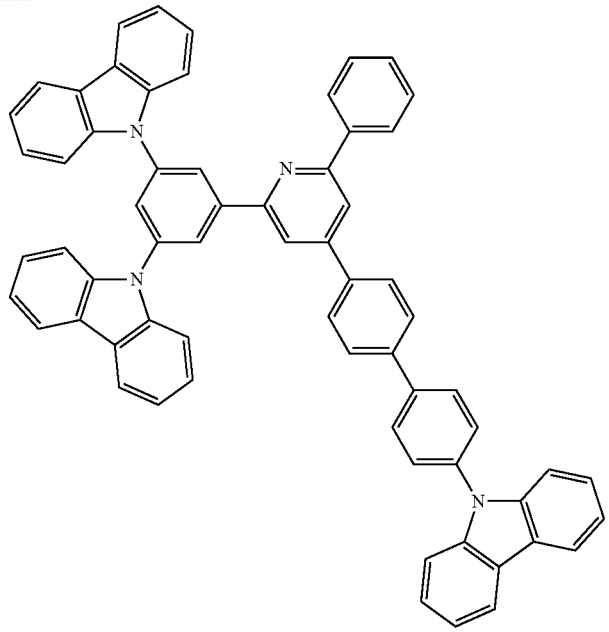
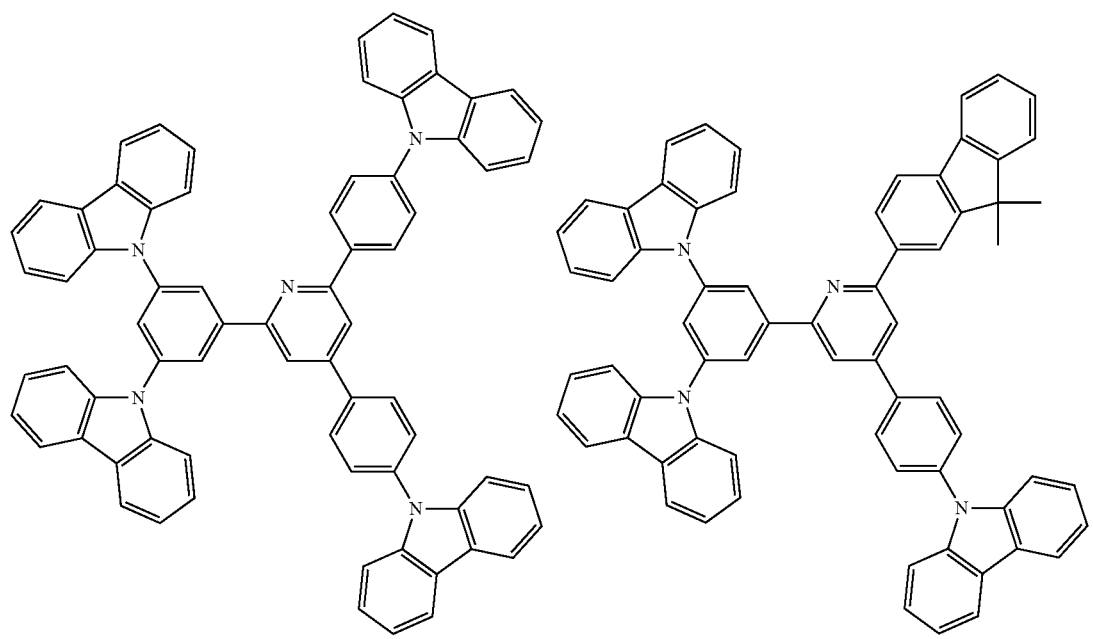

-continued
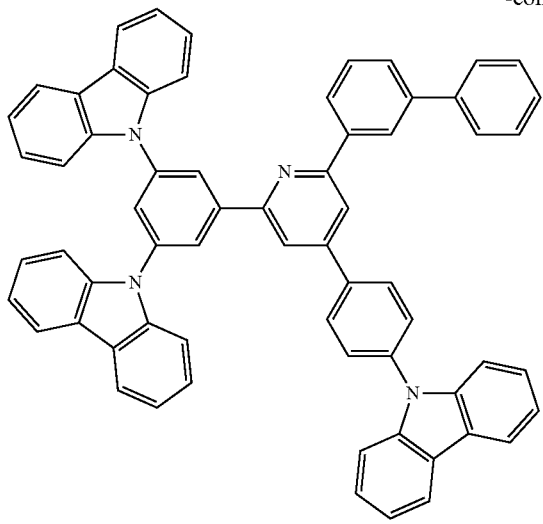
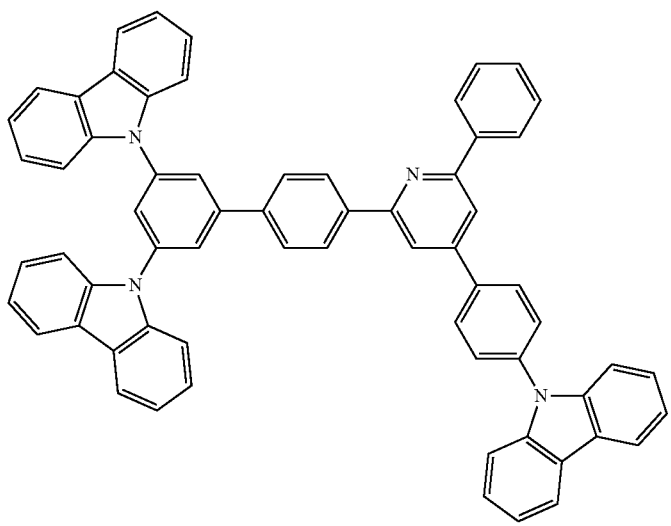
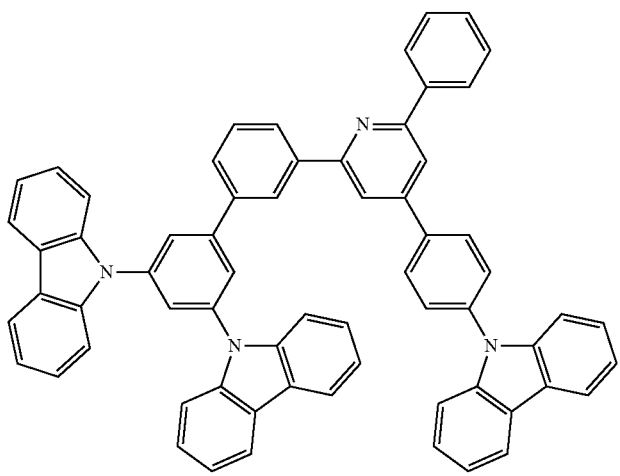

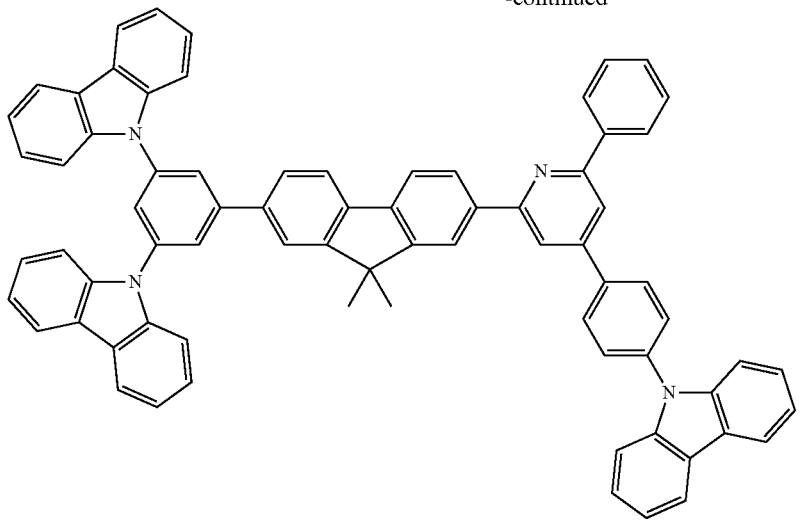

-continued
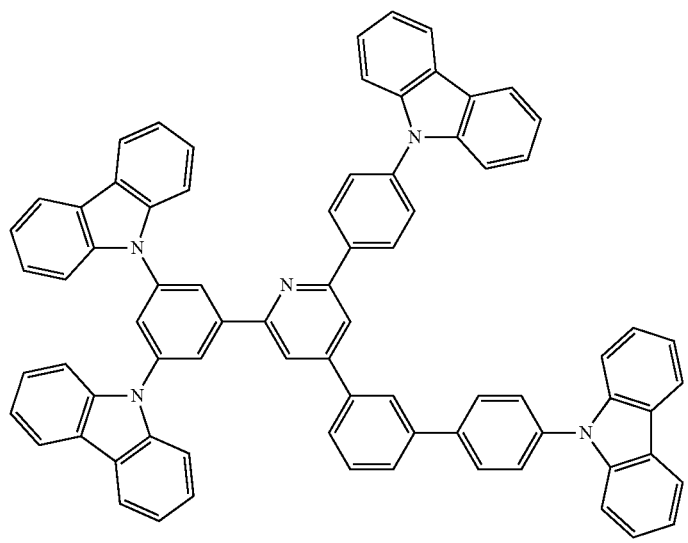
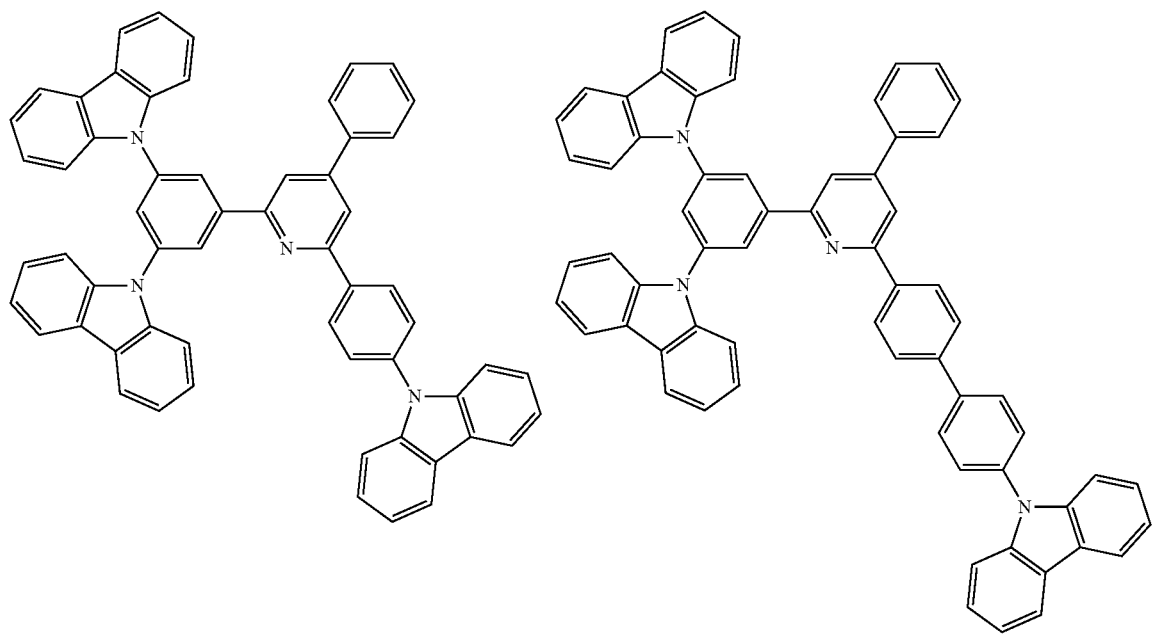

-continued
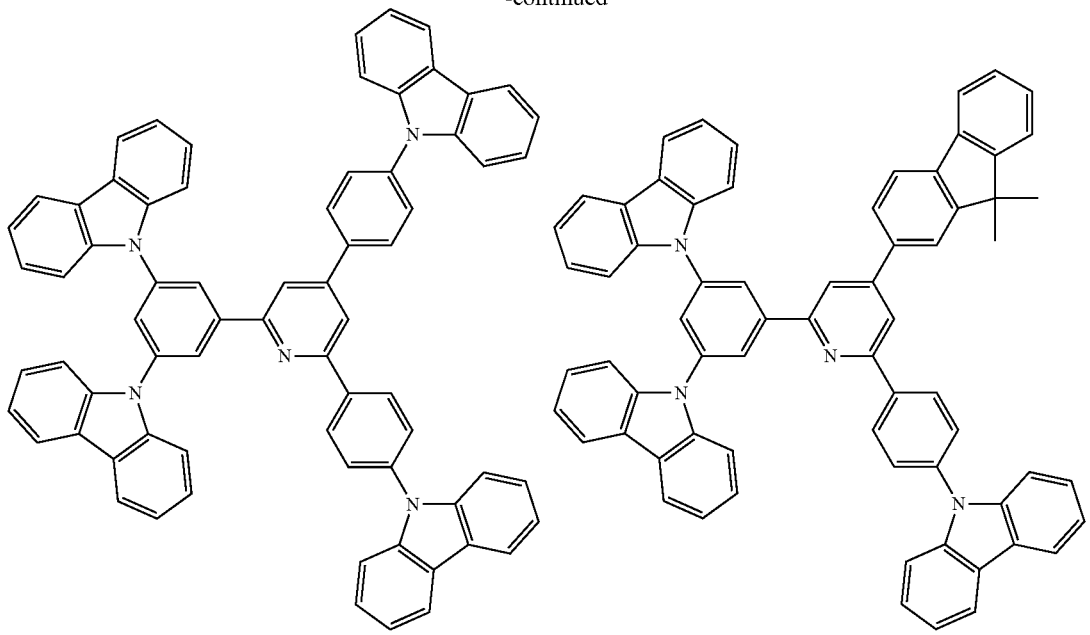
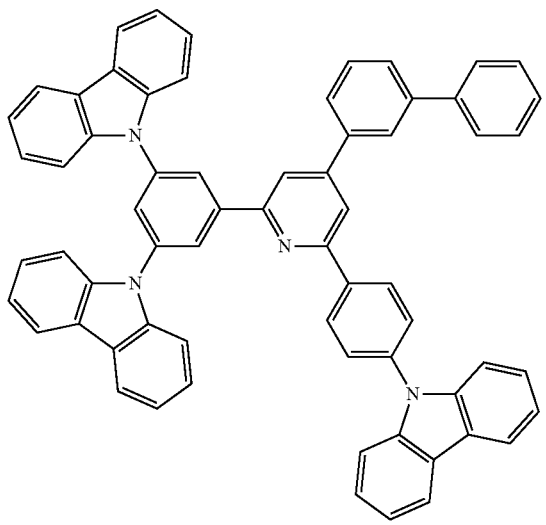
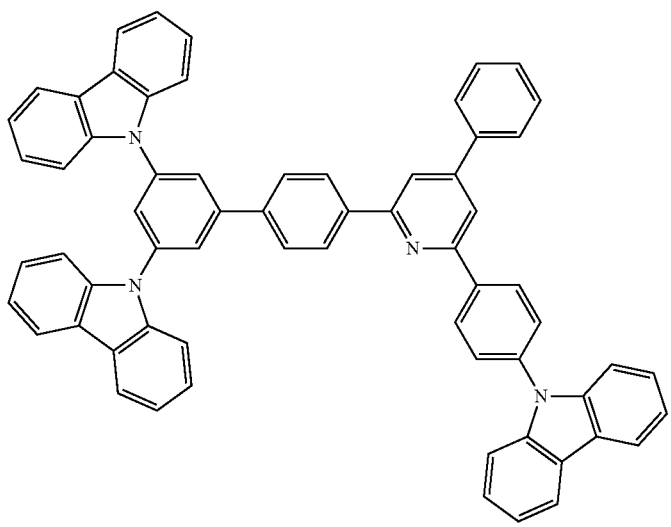

-continued
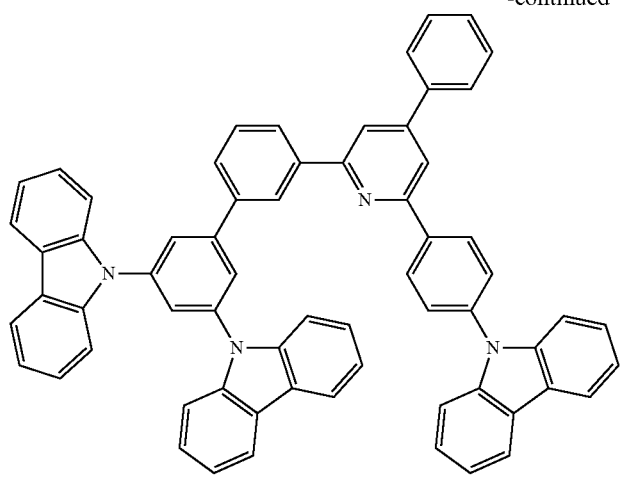
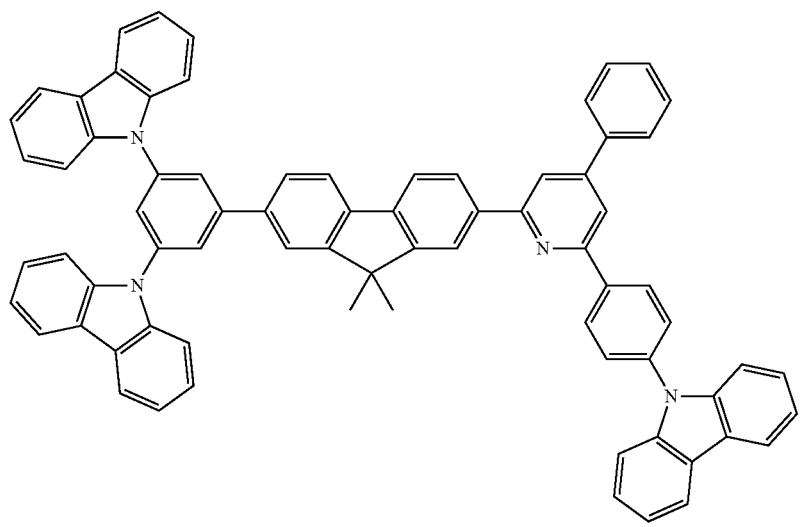
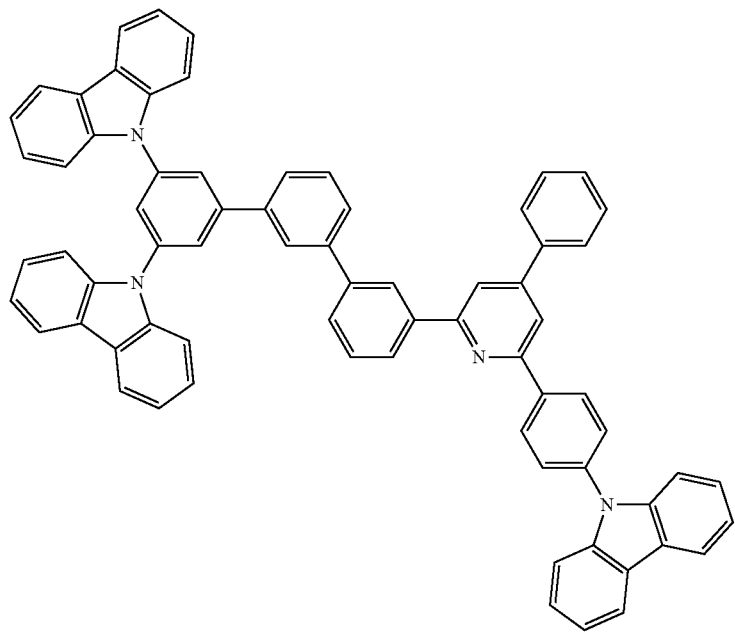

-continued
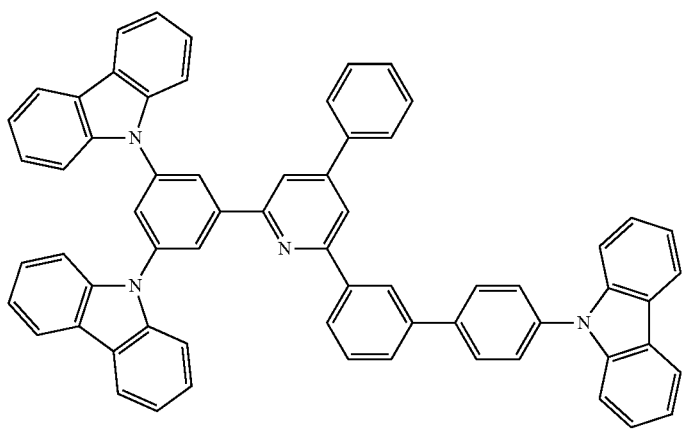
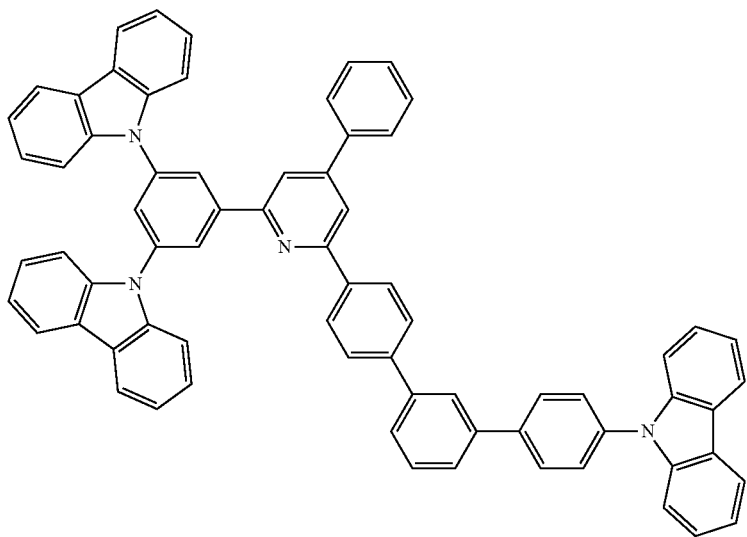
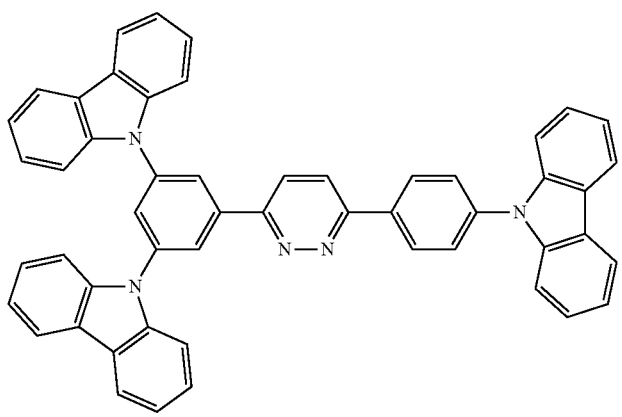

-continued
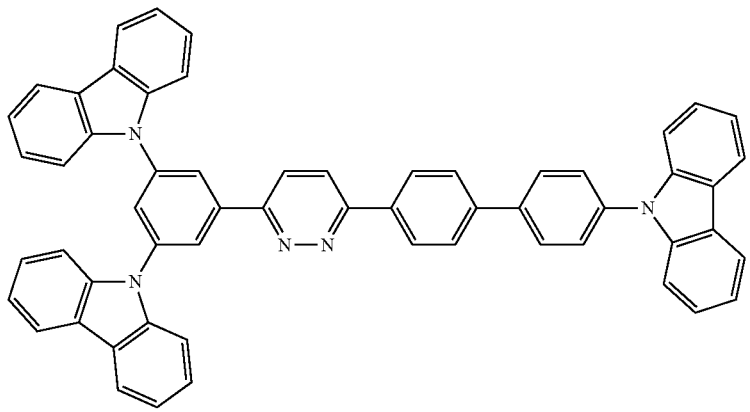
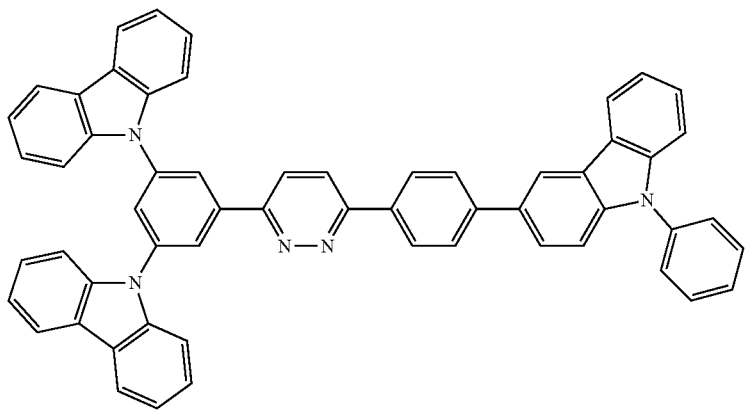
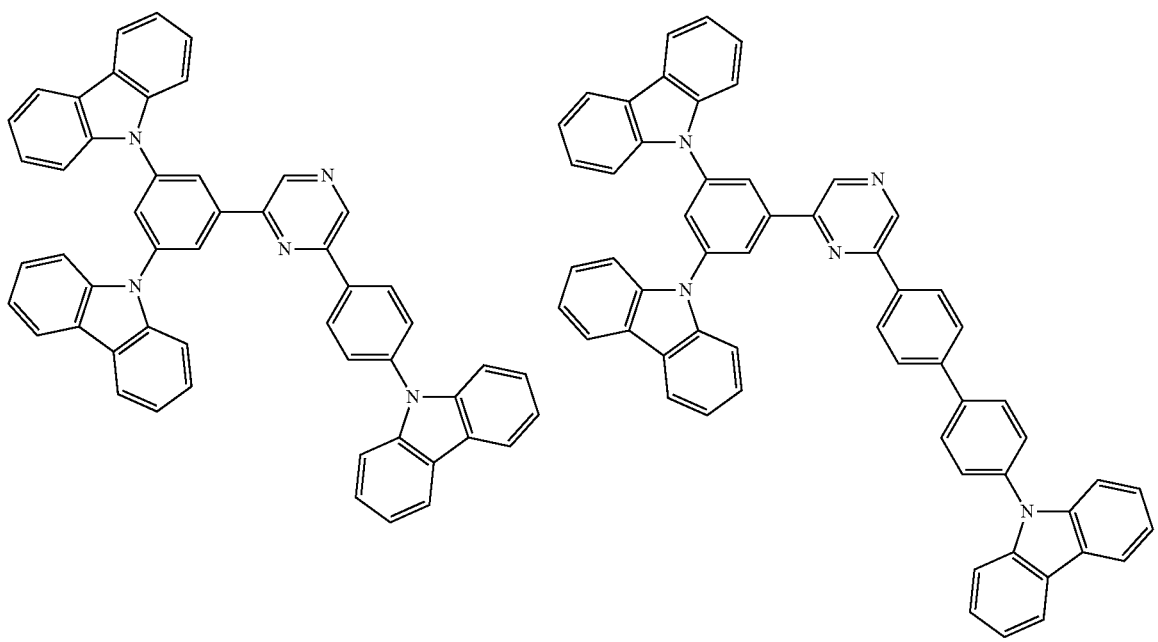

-continued
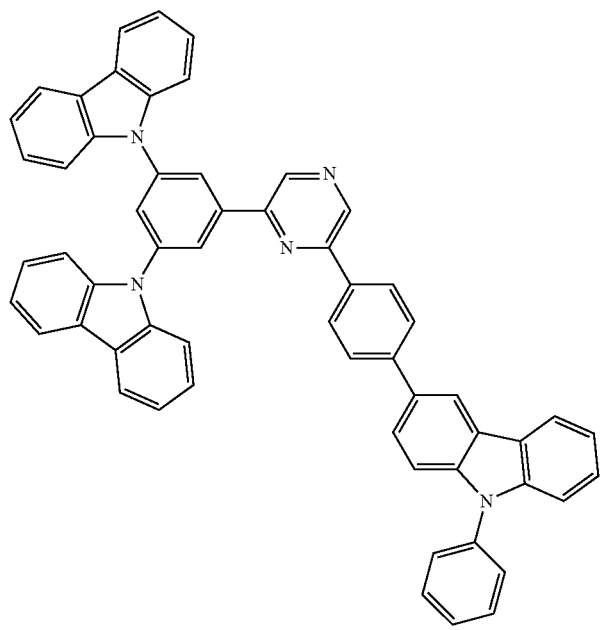
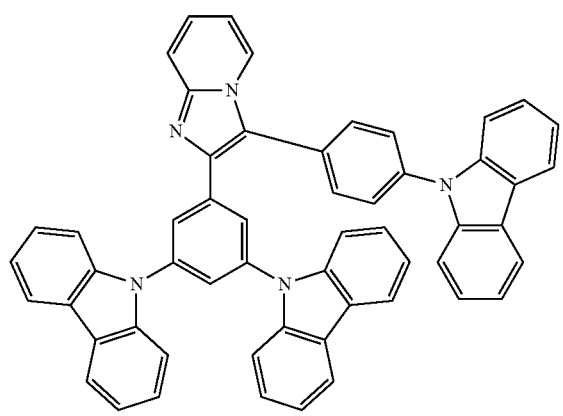
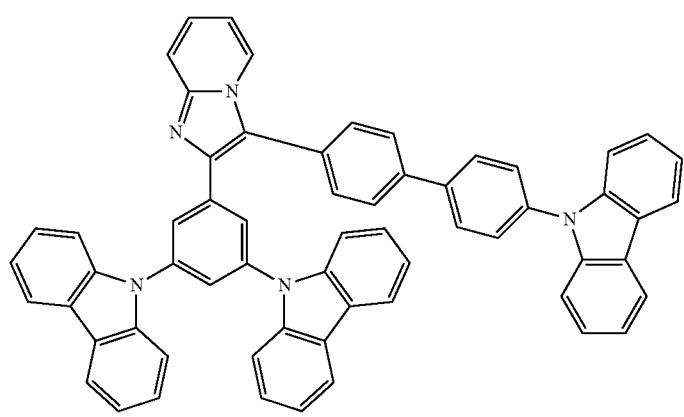

-continued
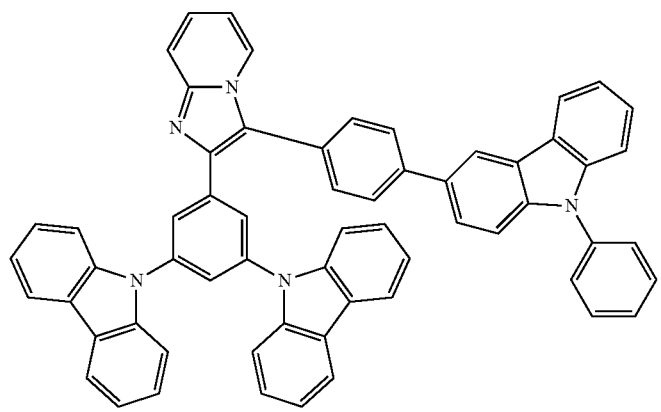
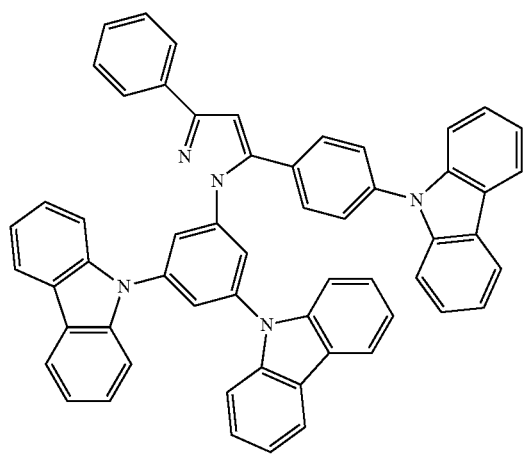
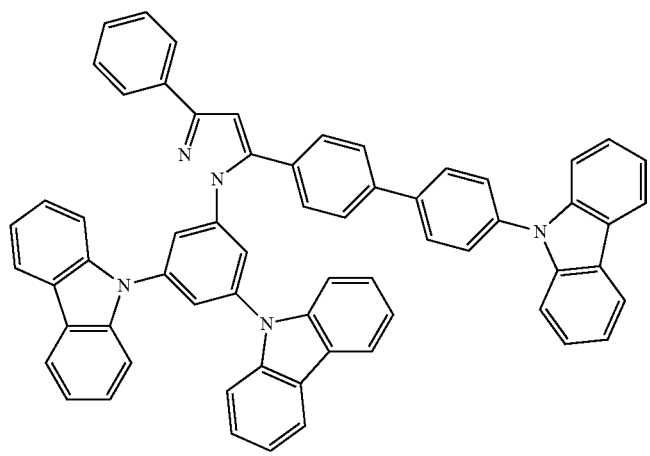

-continued
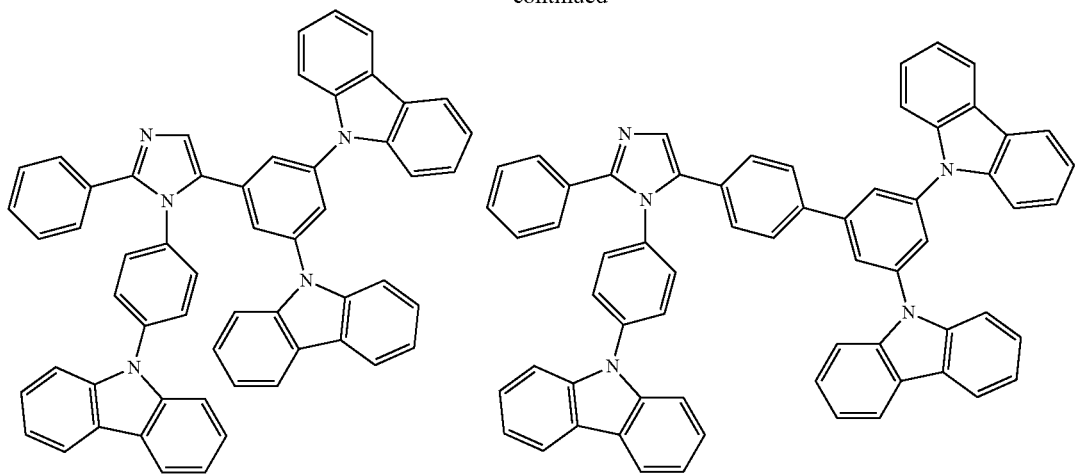
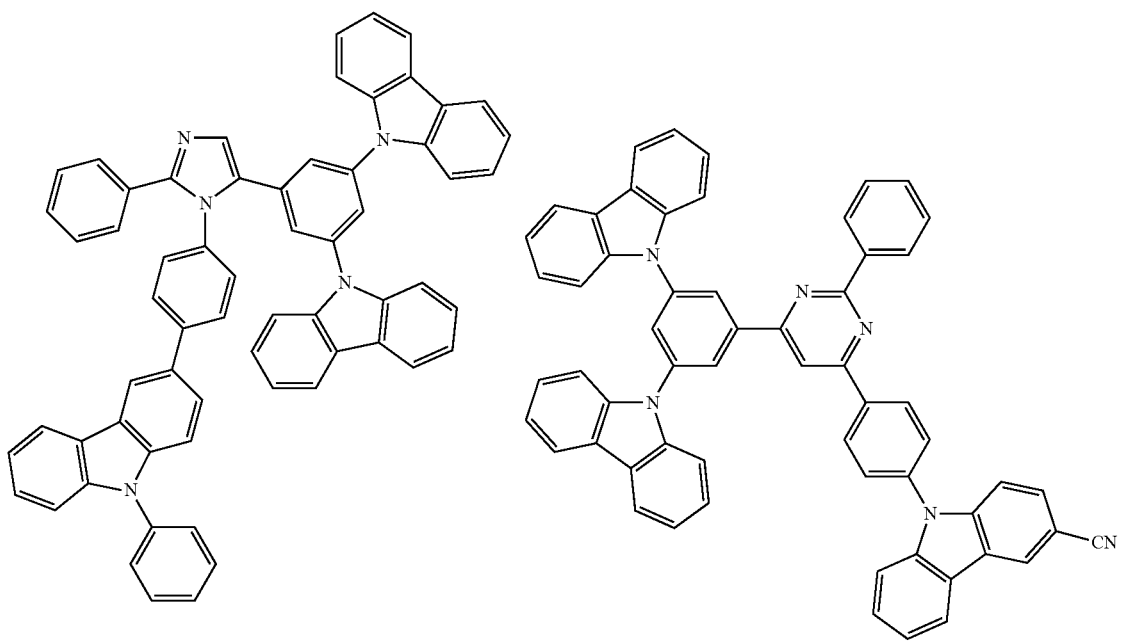
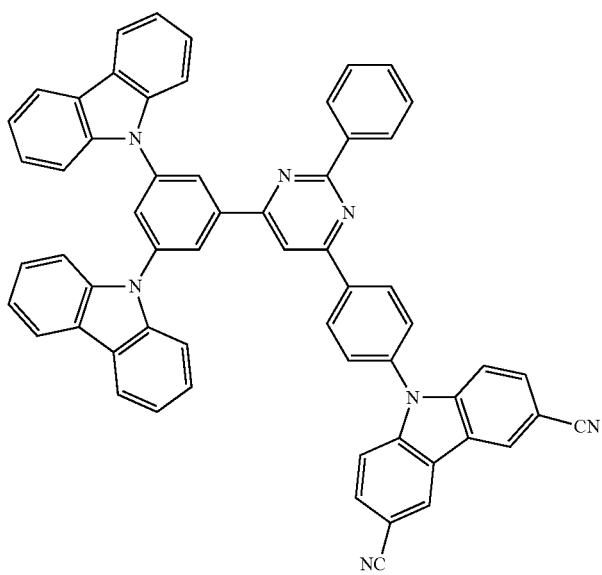

-continued
79
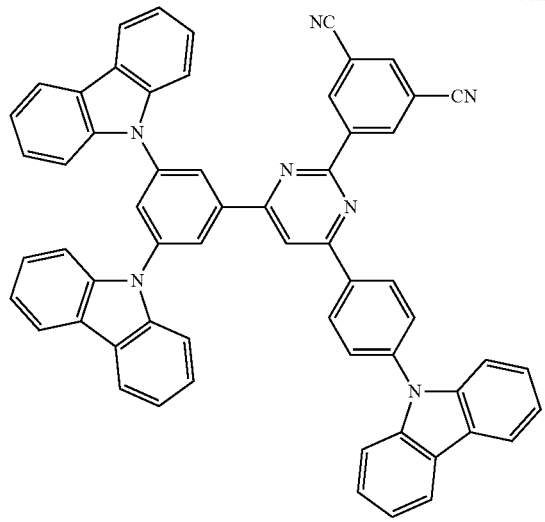
80
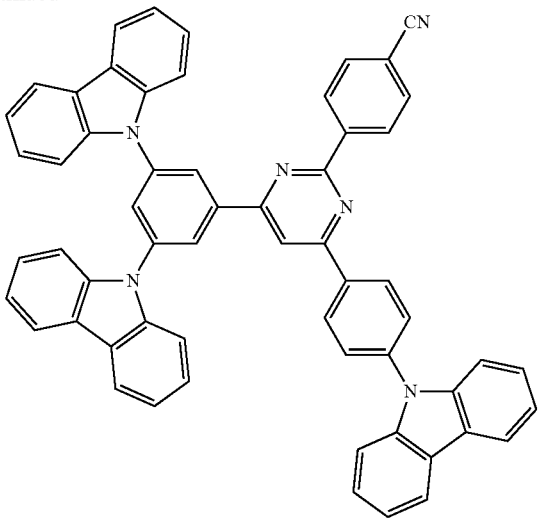
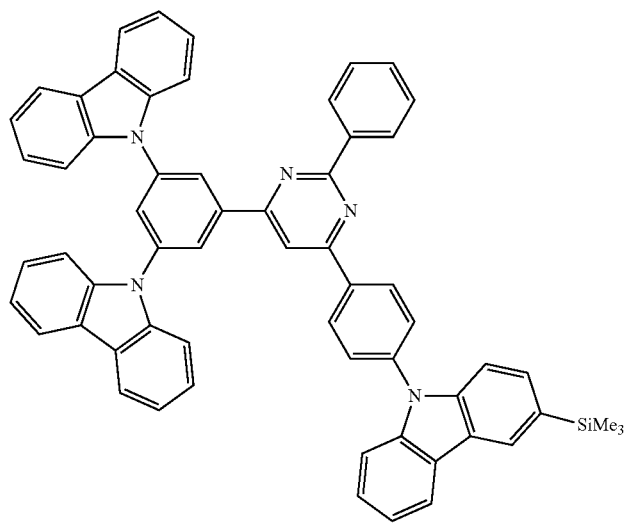
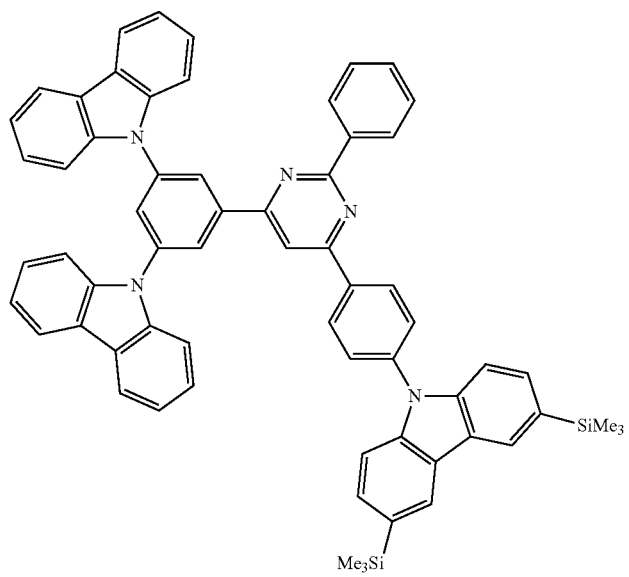

-continued
81
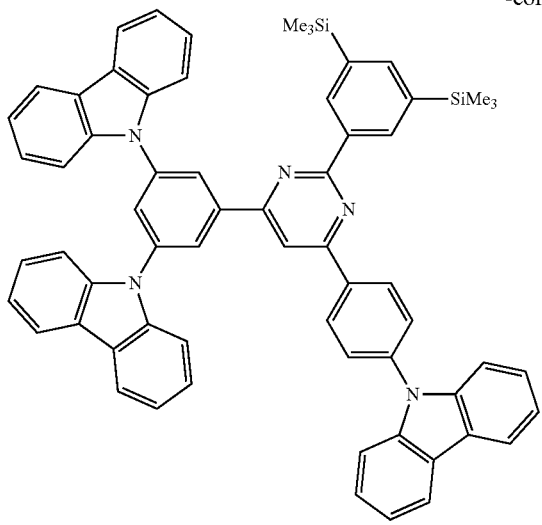
82
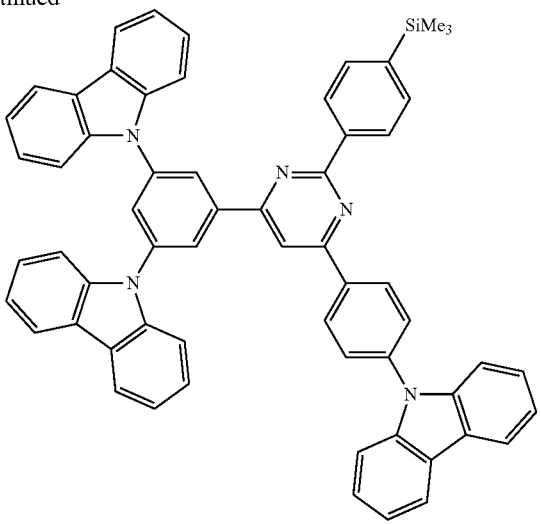
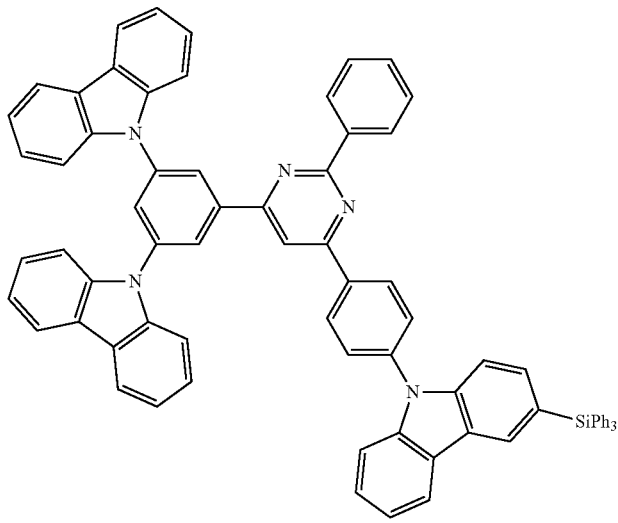
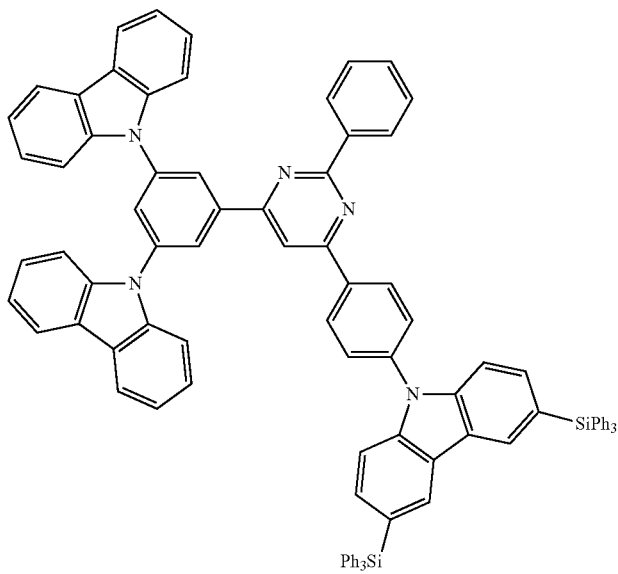

83
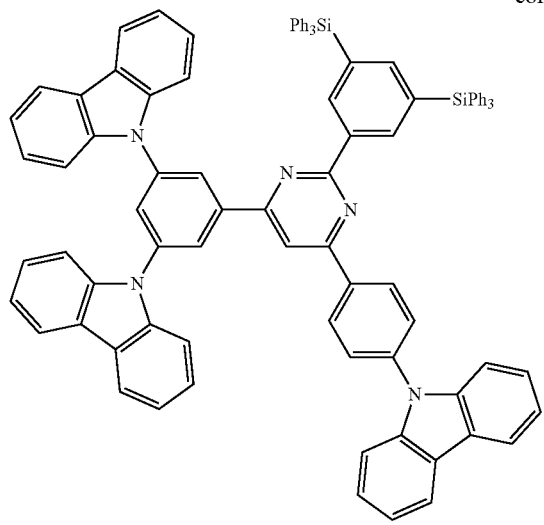
84
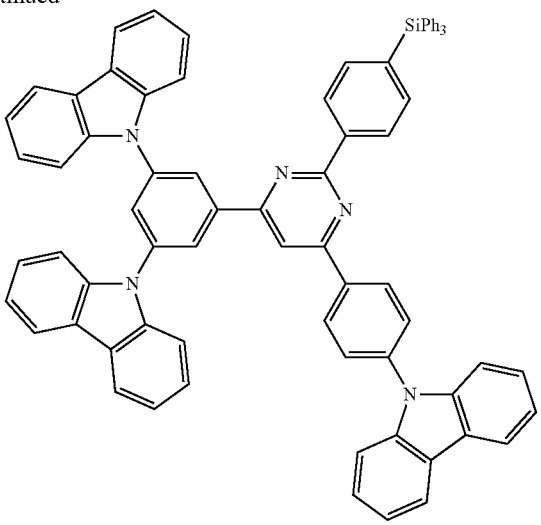
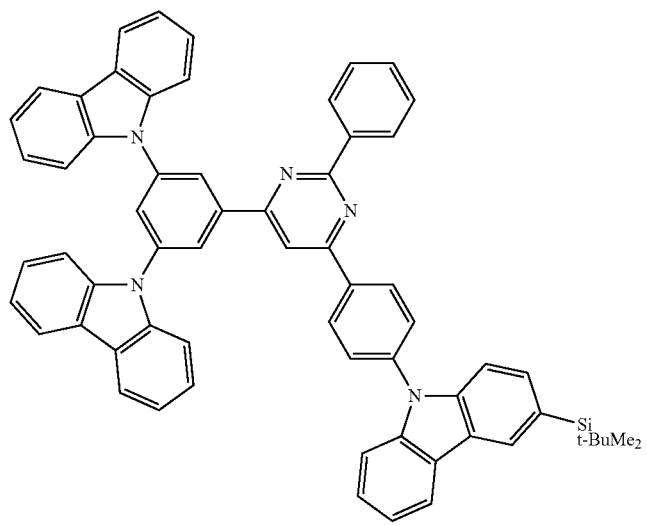
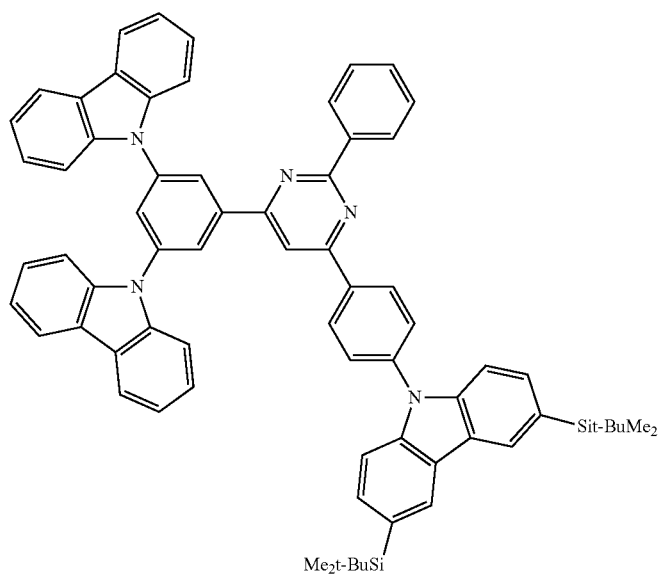

-continued
85
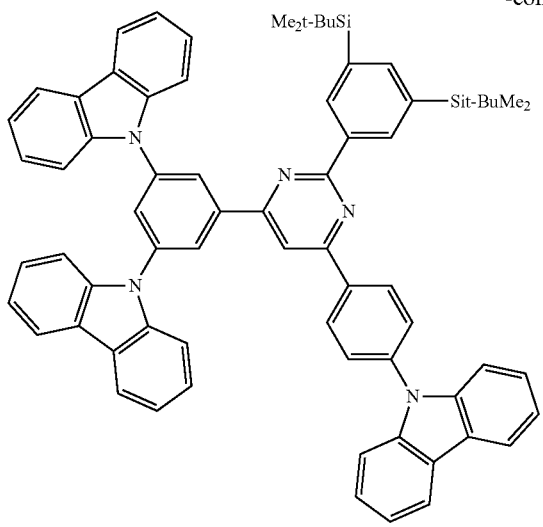
86
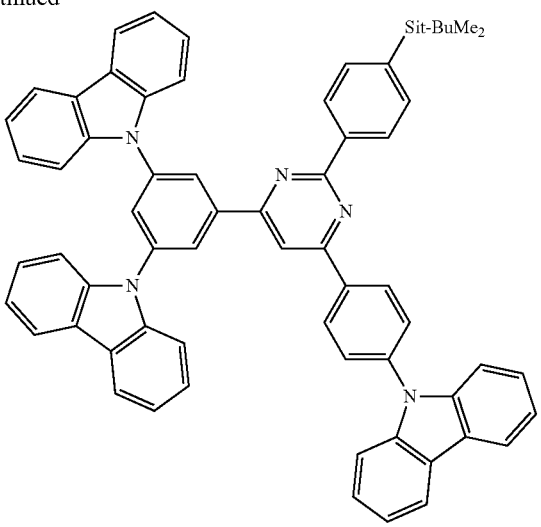
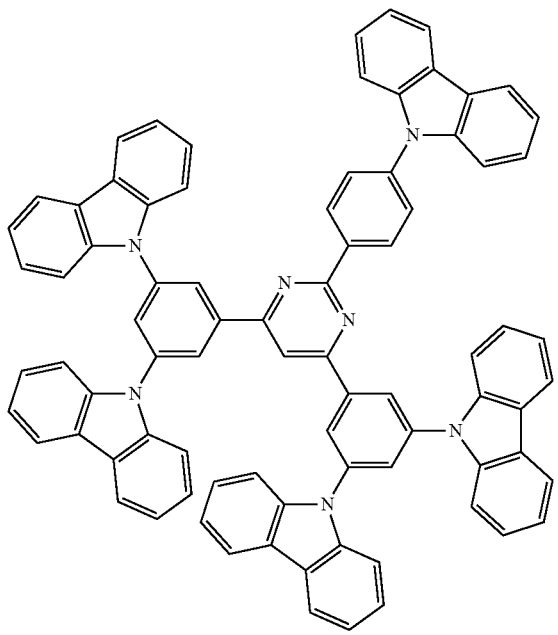
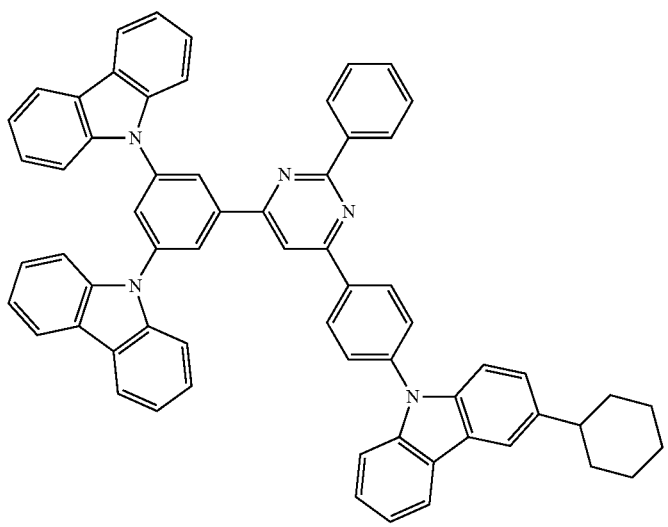

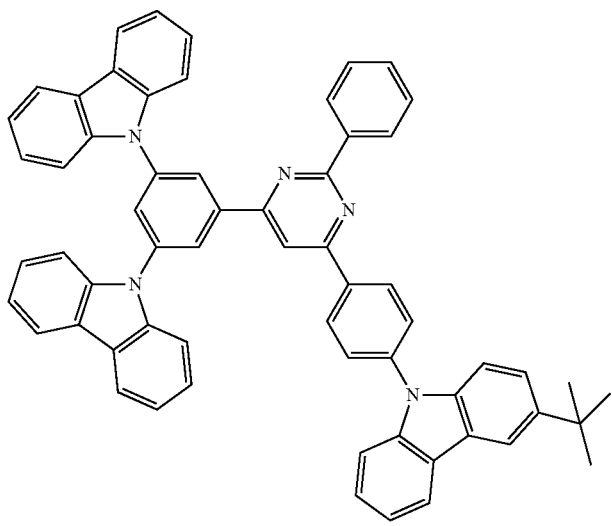
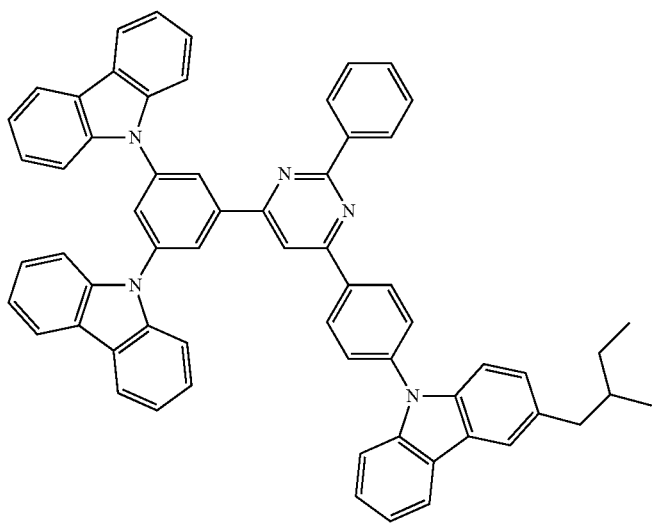
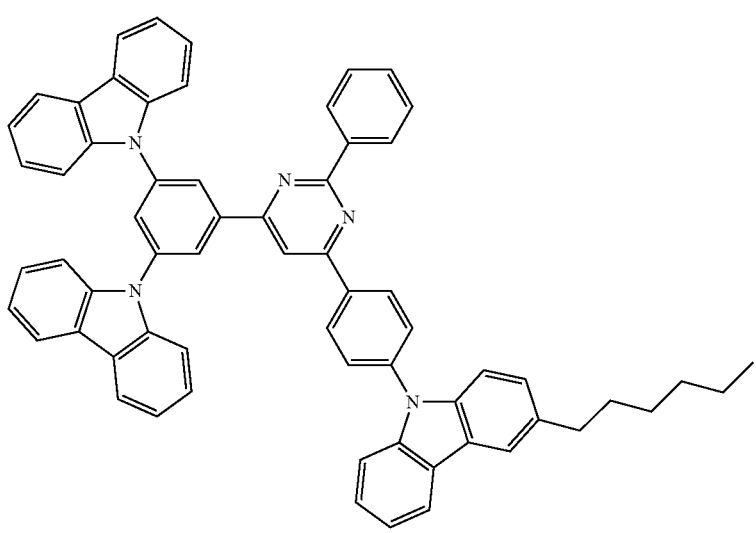

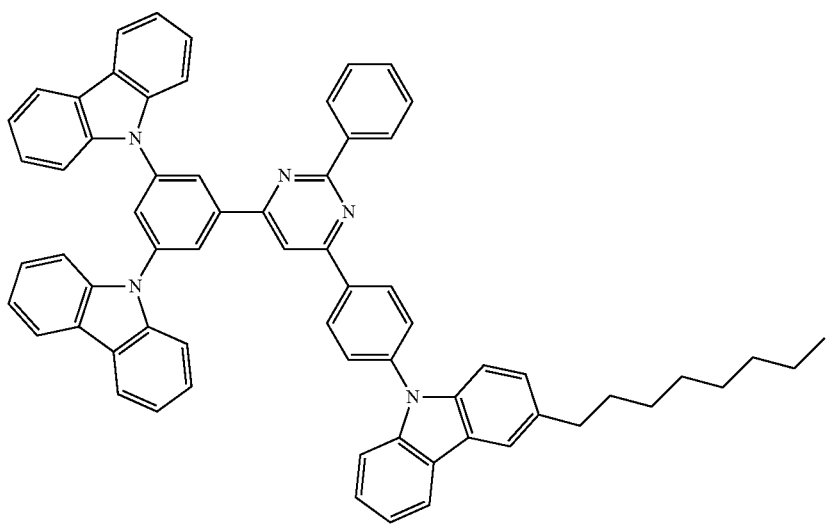
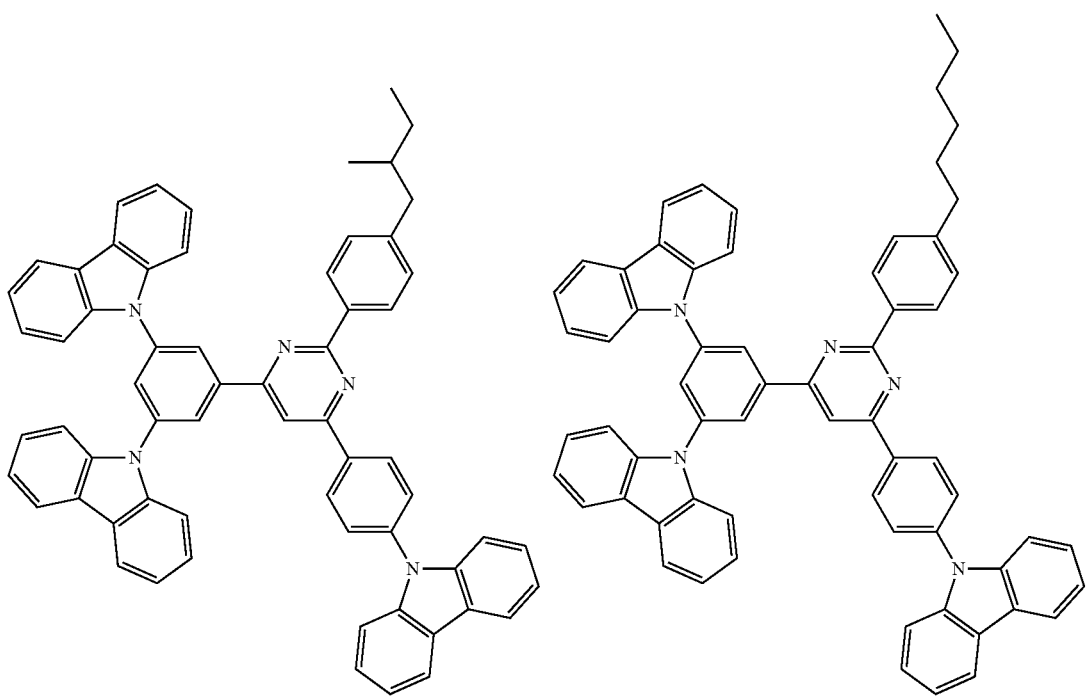

91
-continued
92
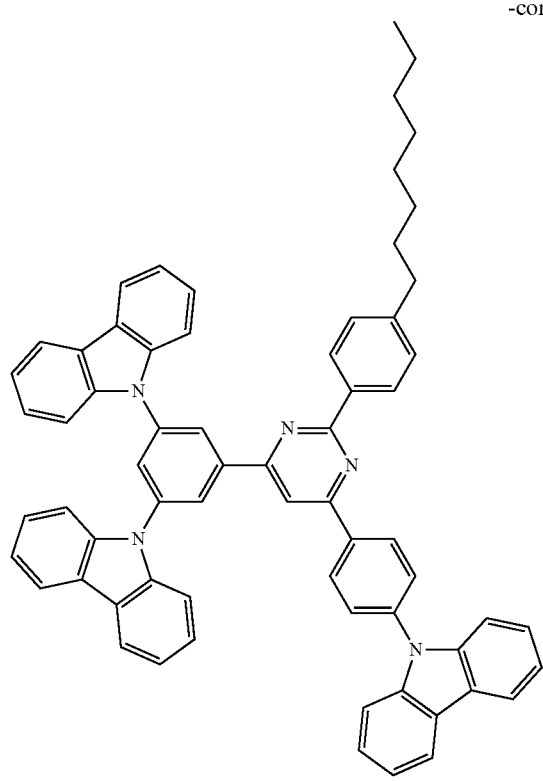
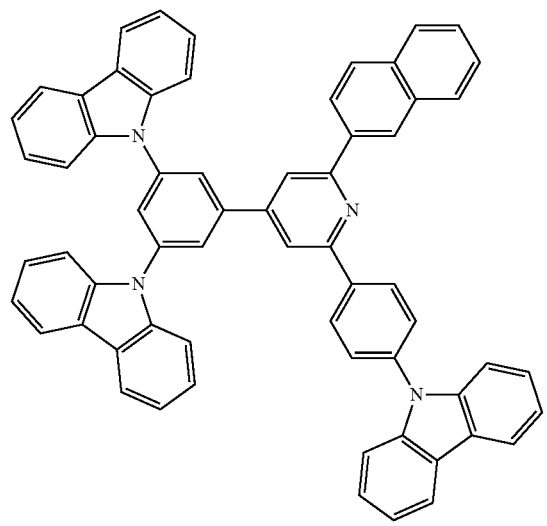
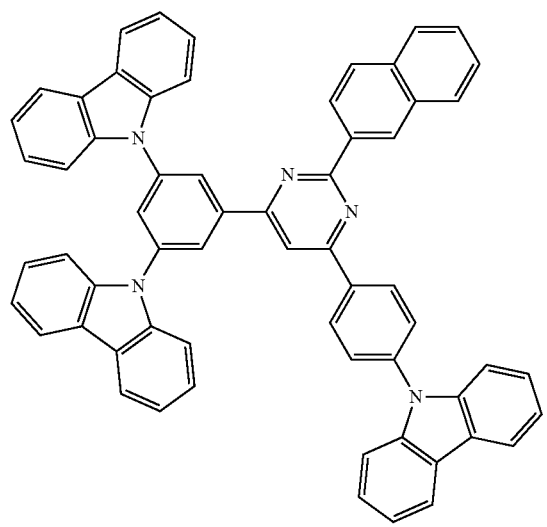
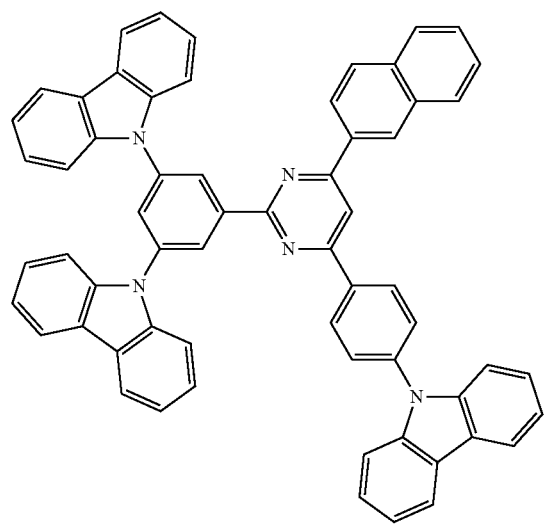

-continued
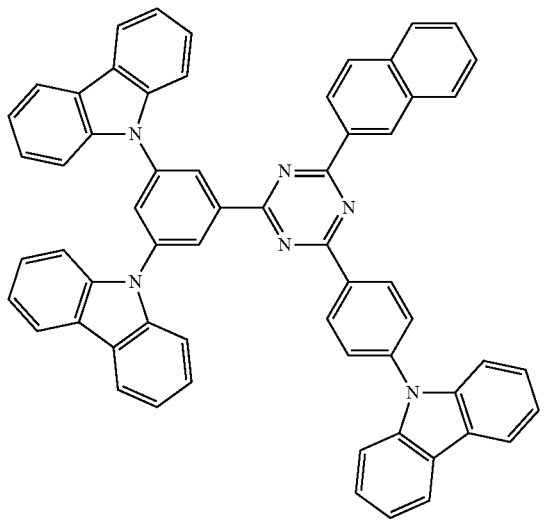
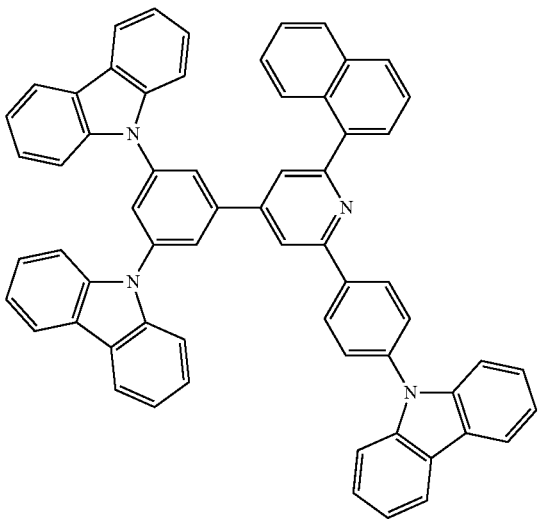
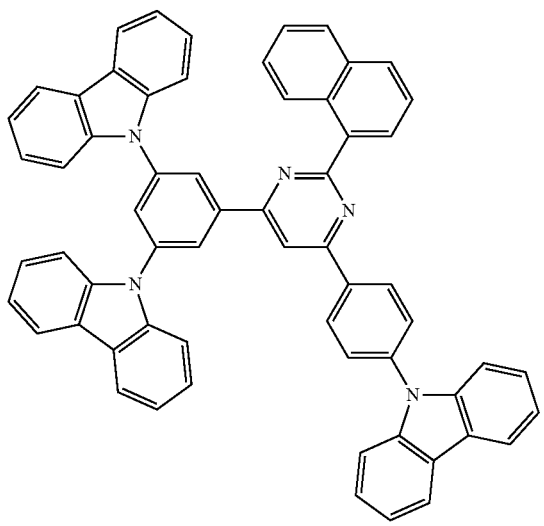
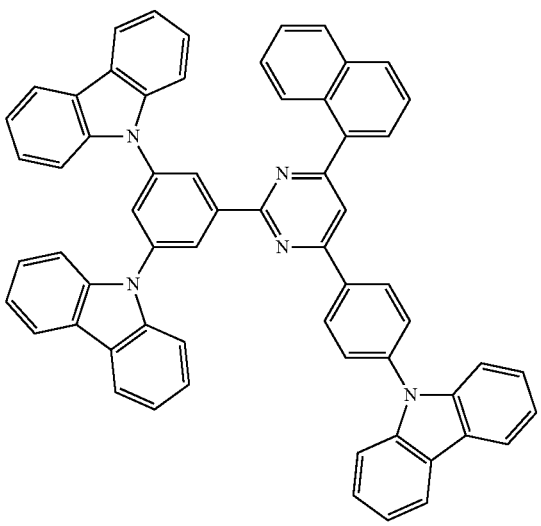
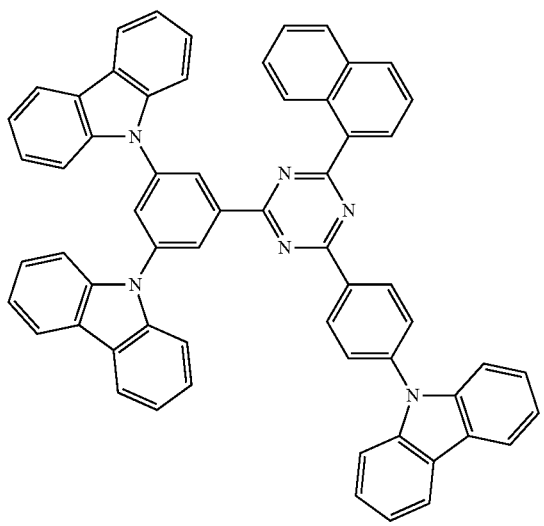
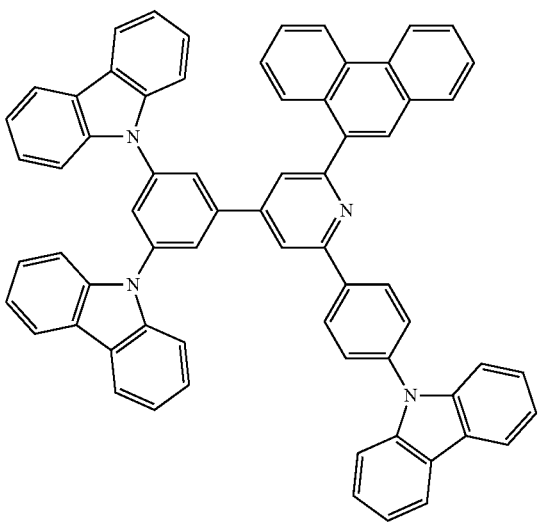

95
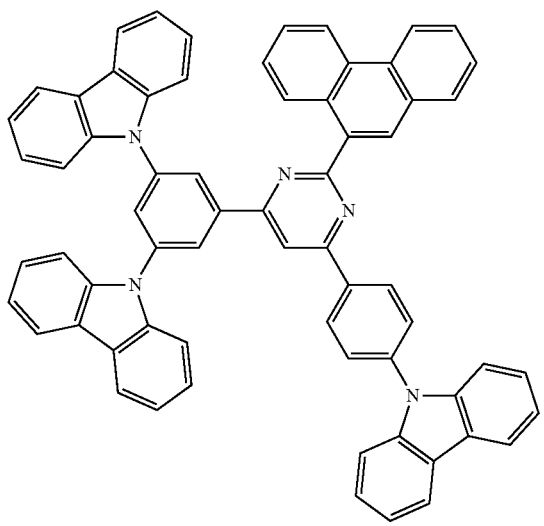
96
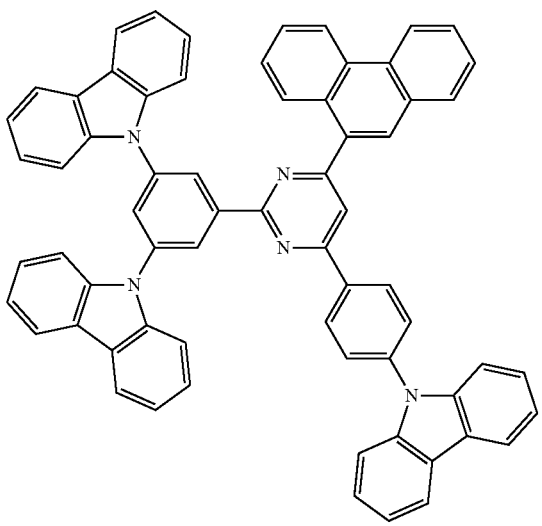
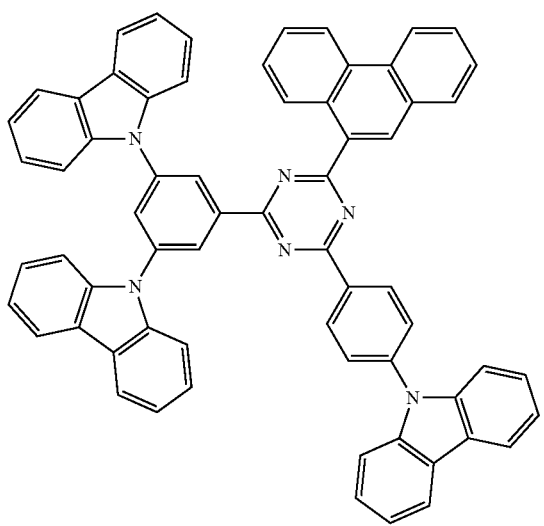
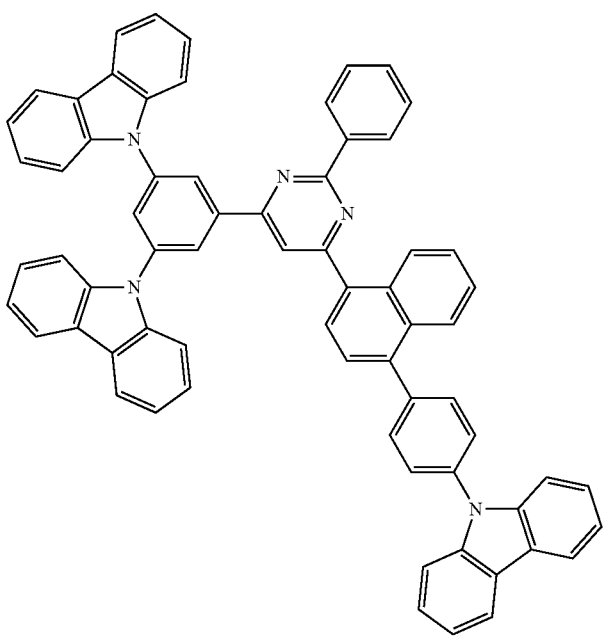

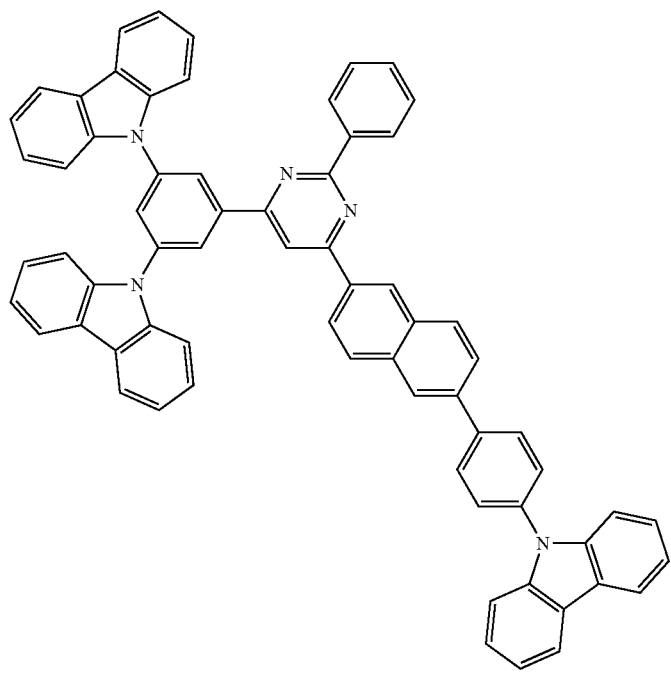
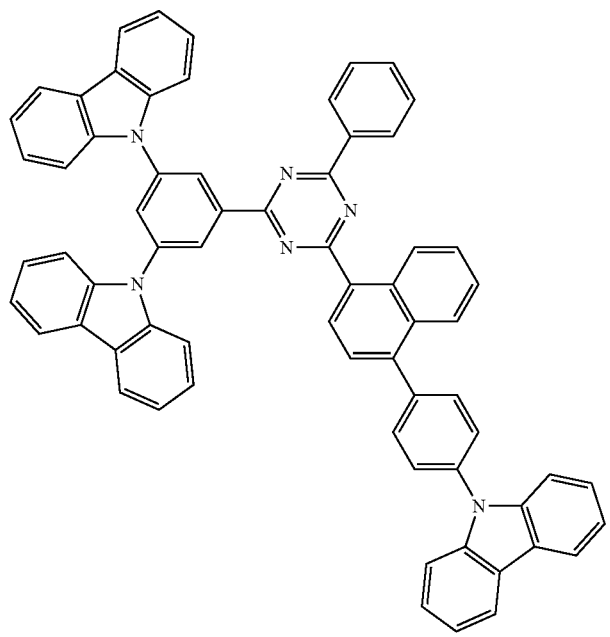

-continued
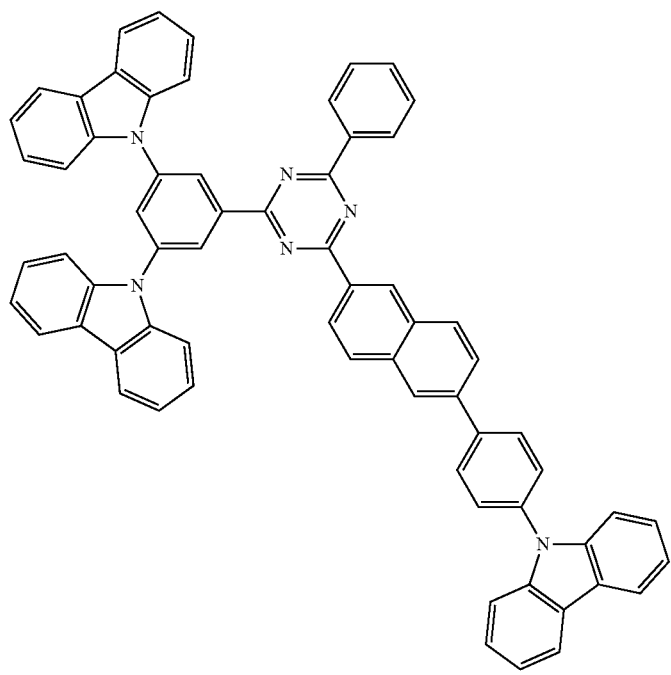
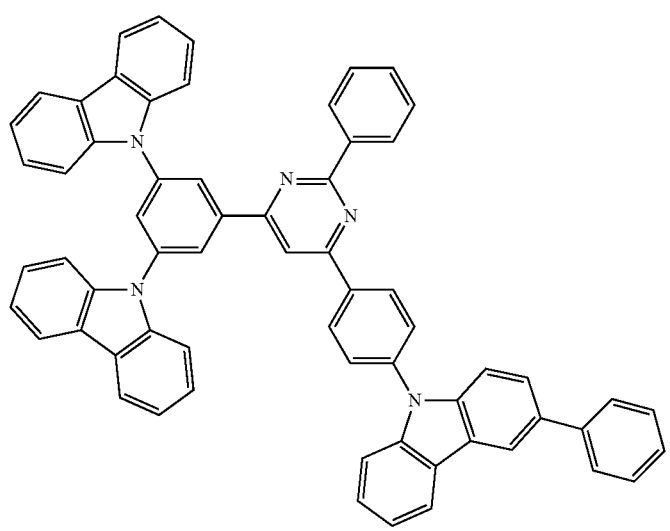

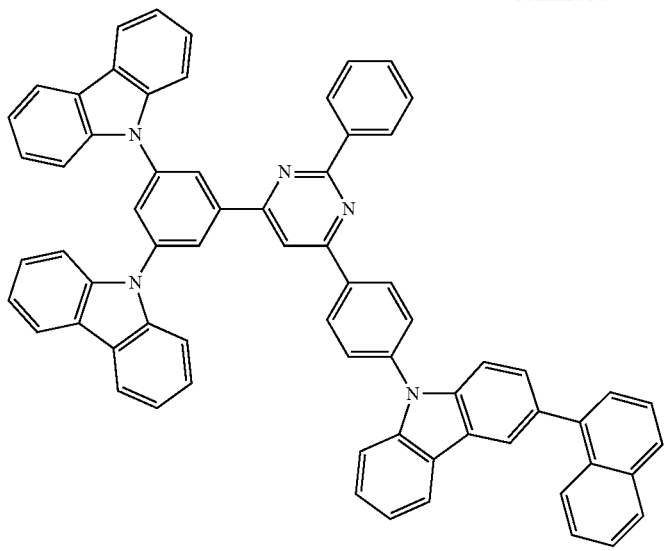
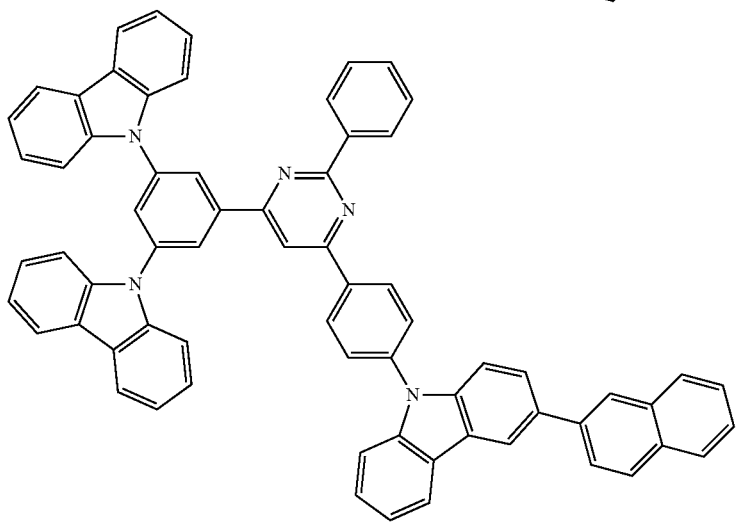
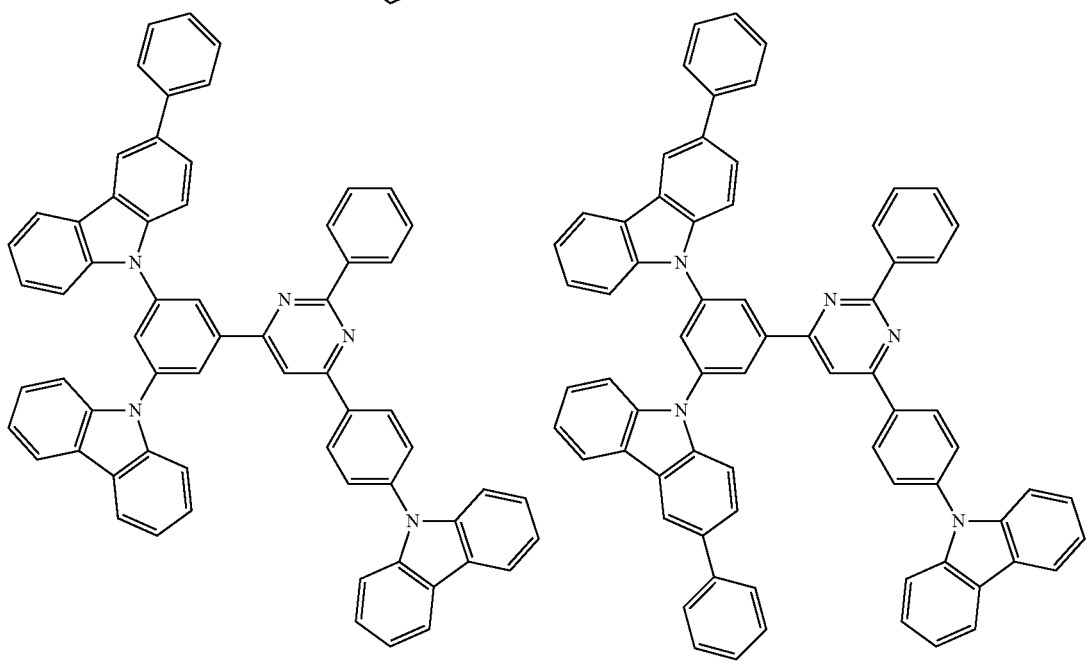

103
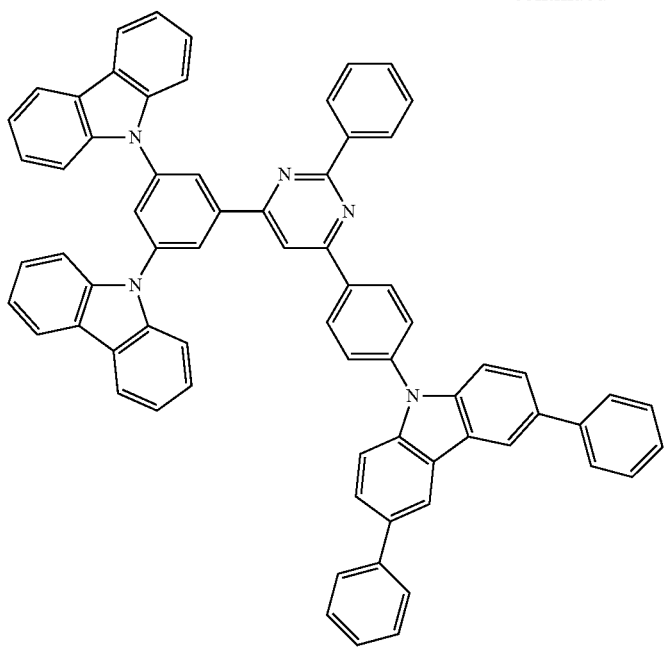
104
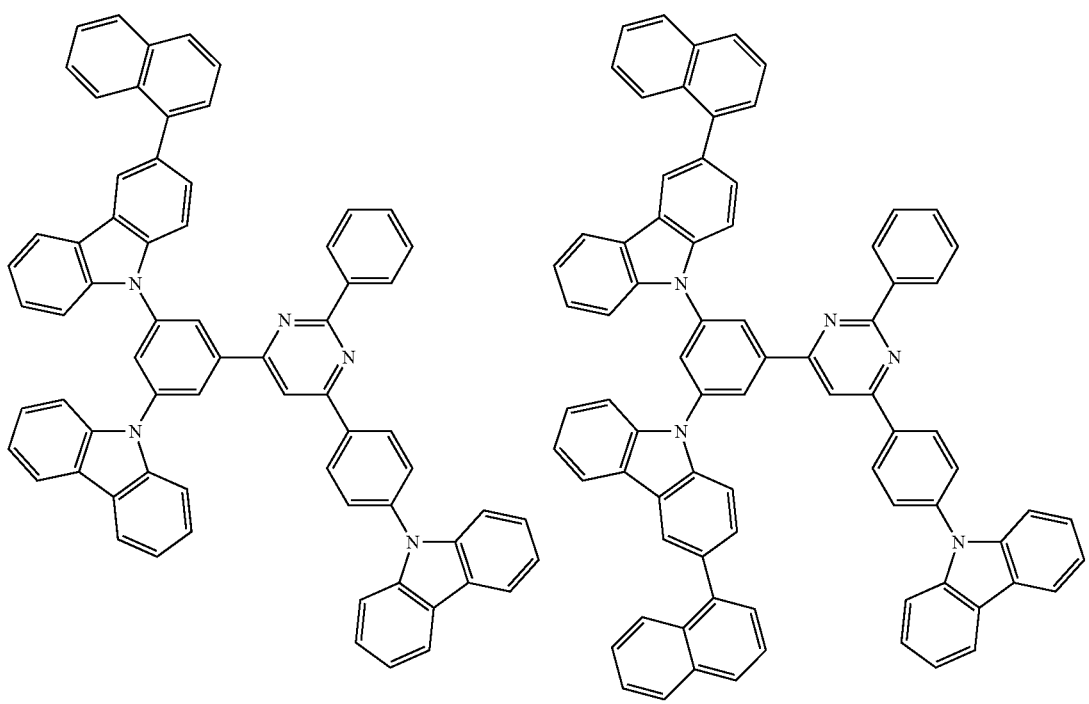

105
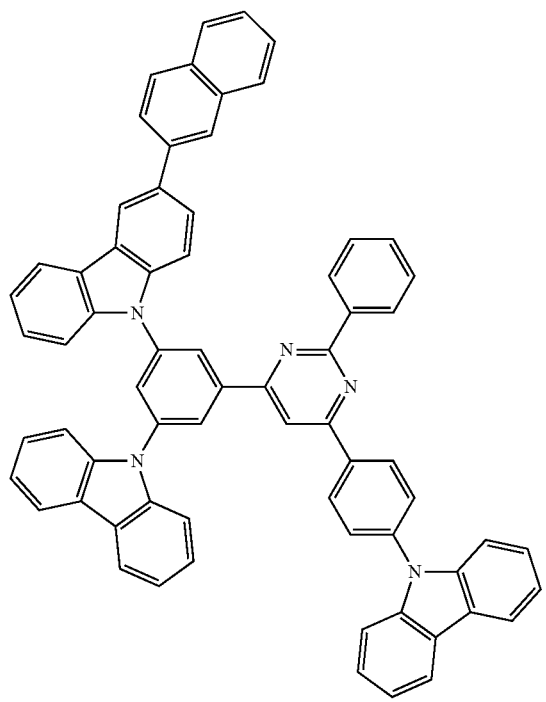
106
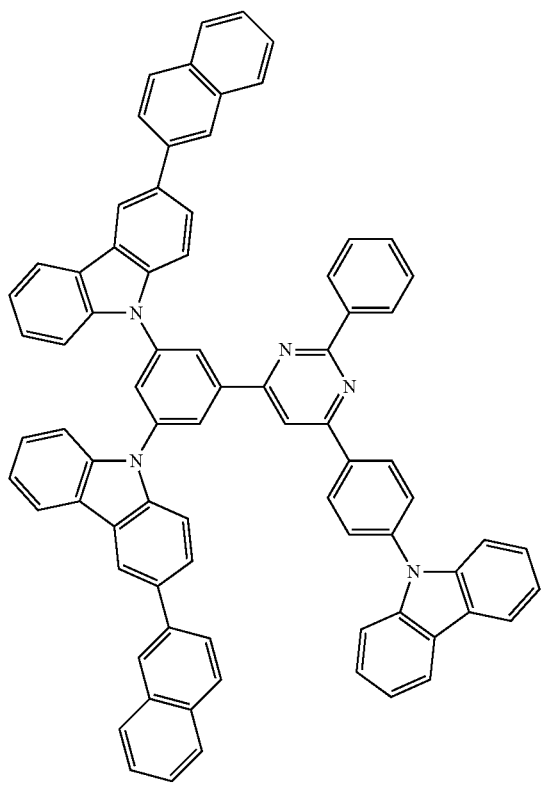
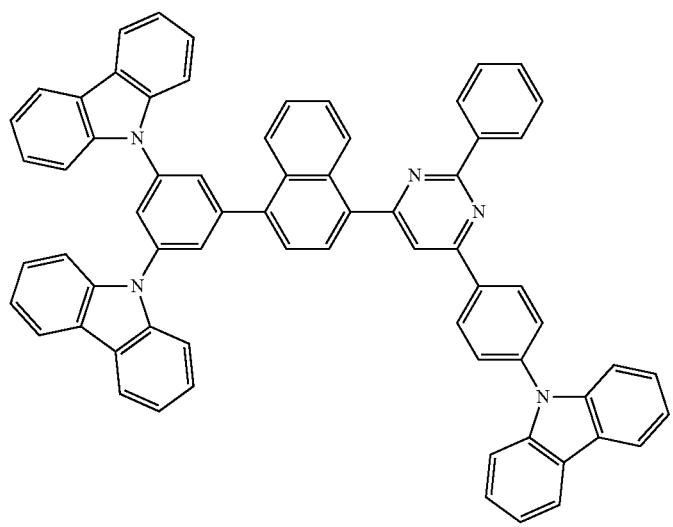

-continued
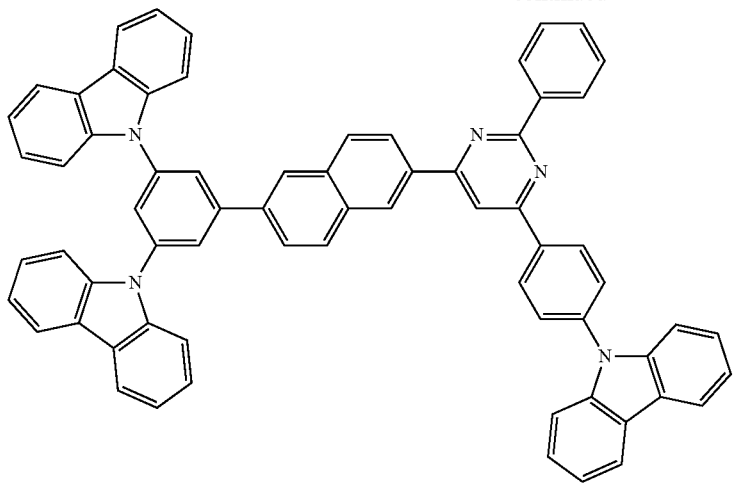
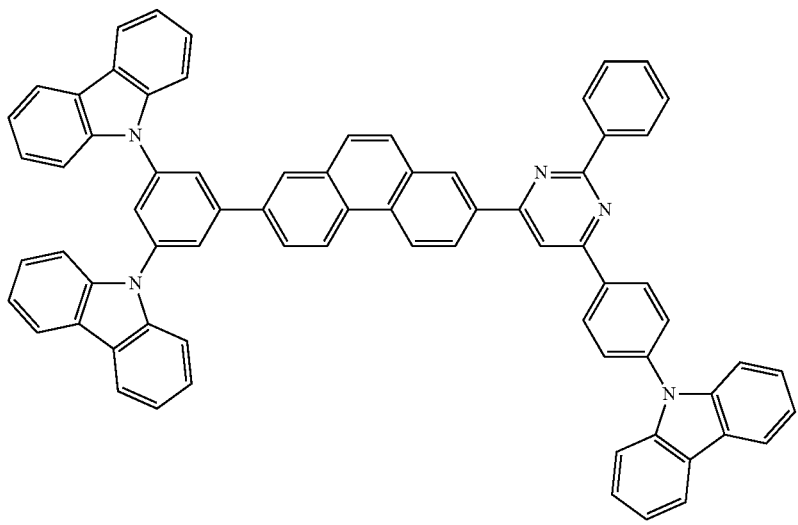
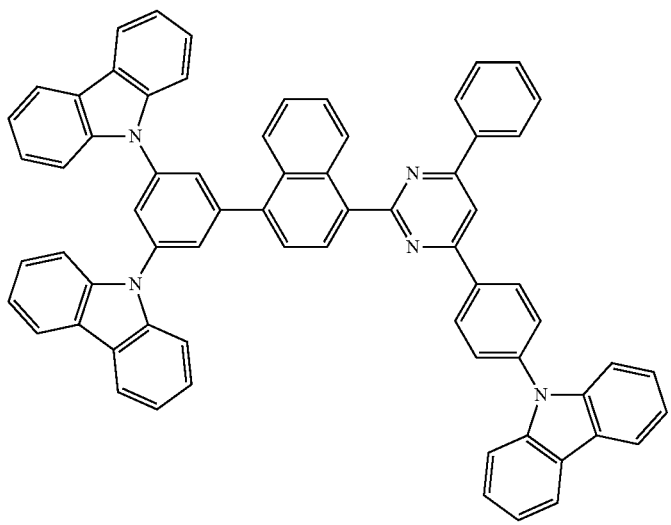

-continued
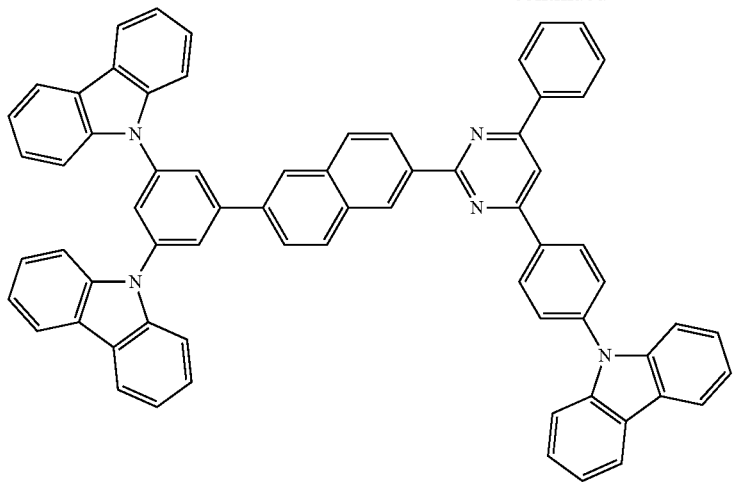
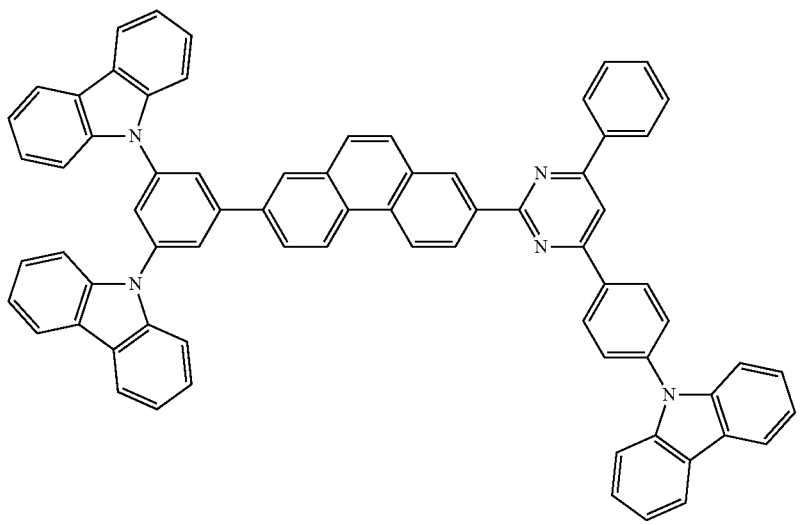
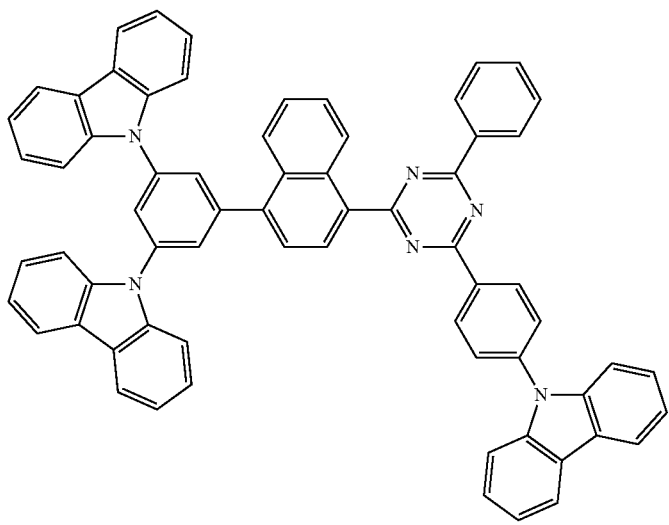

-continued
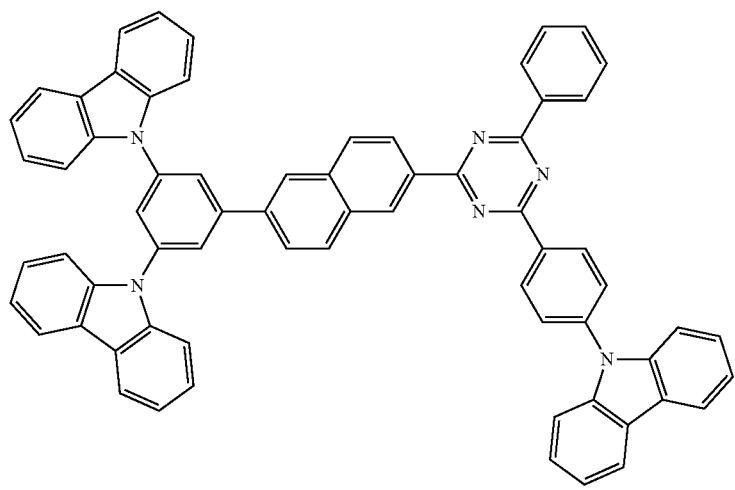
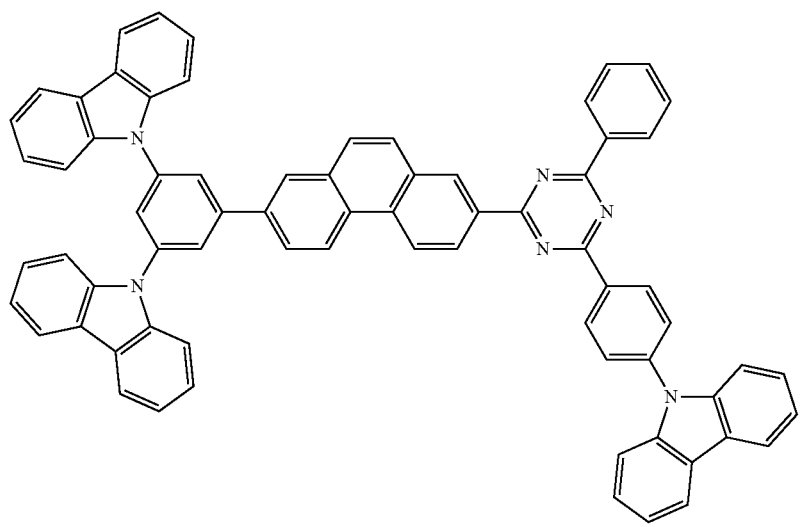
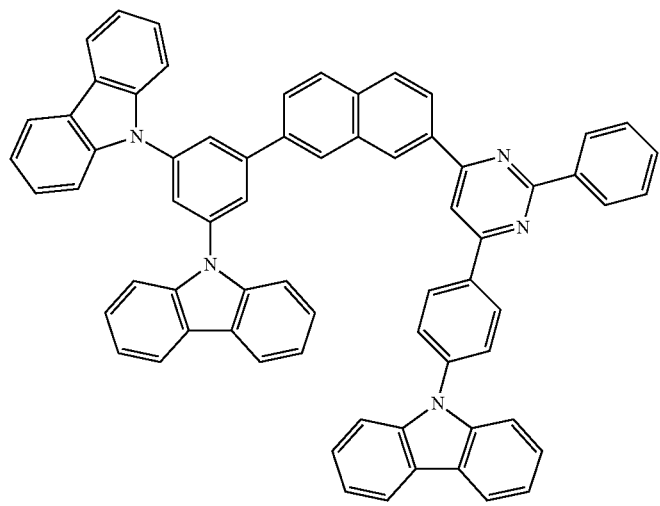

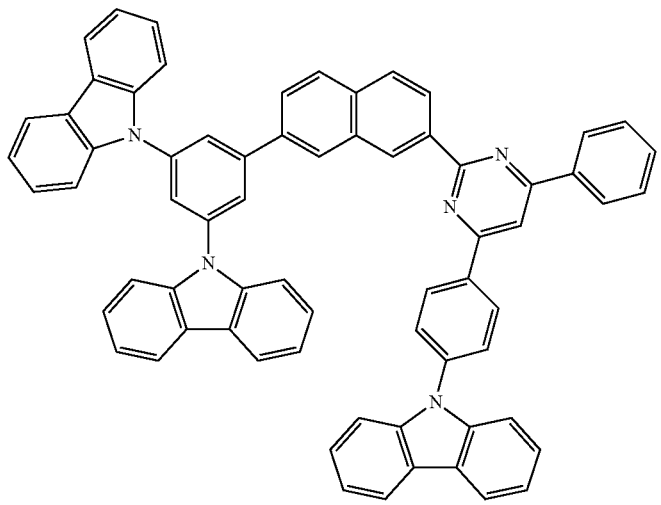
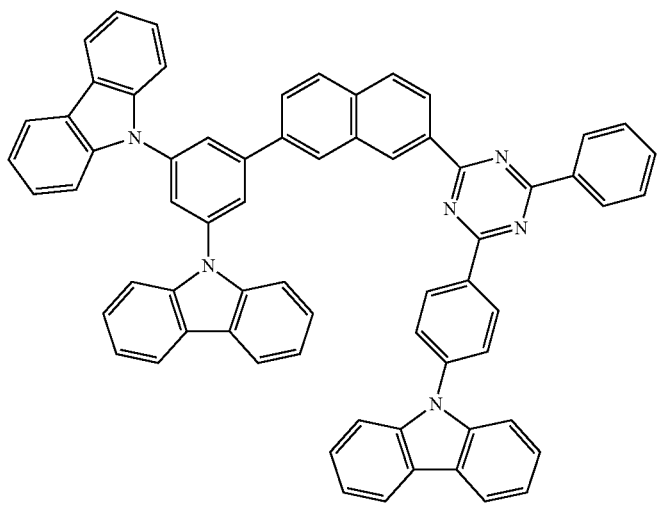
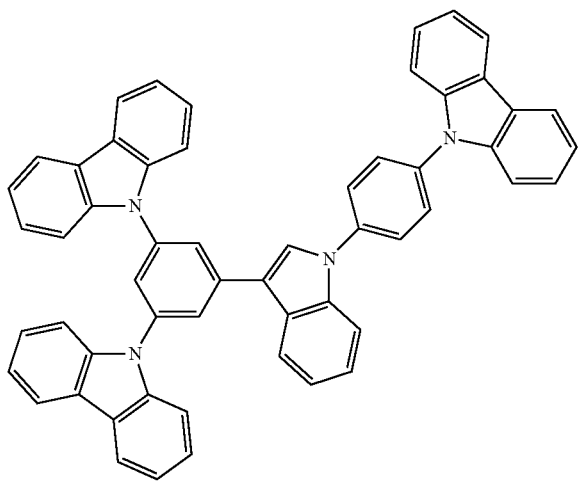

-continued
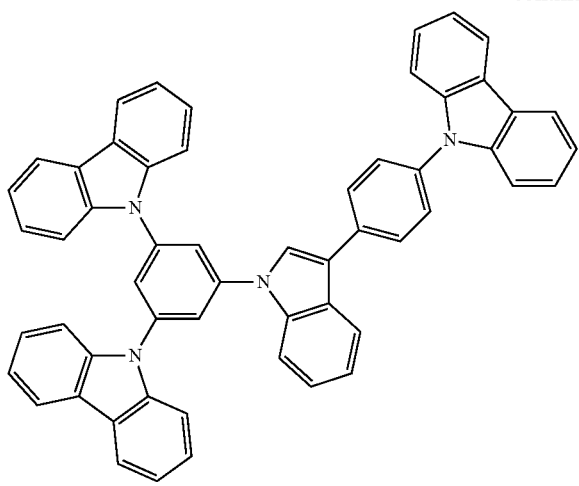
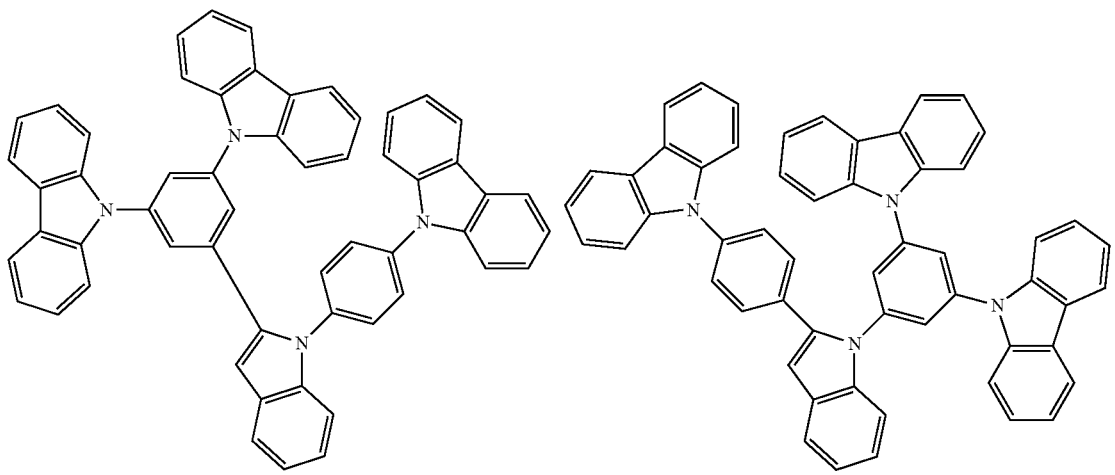
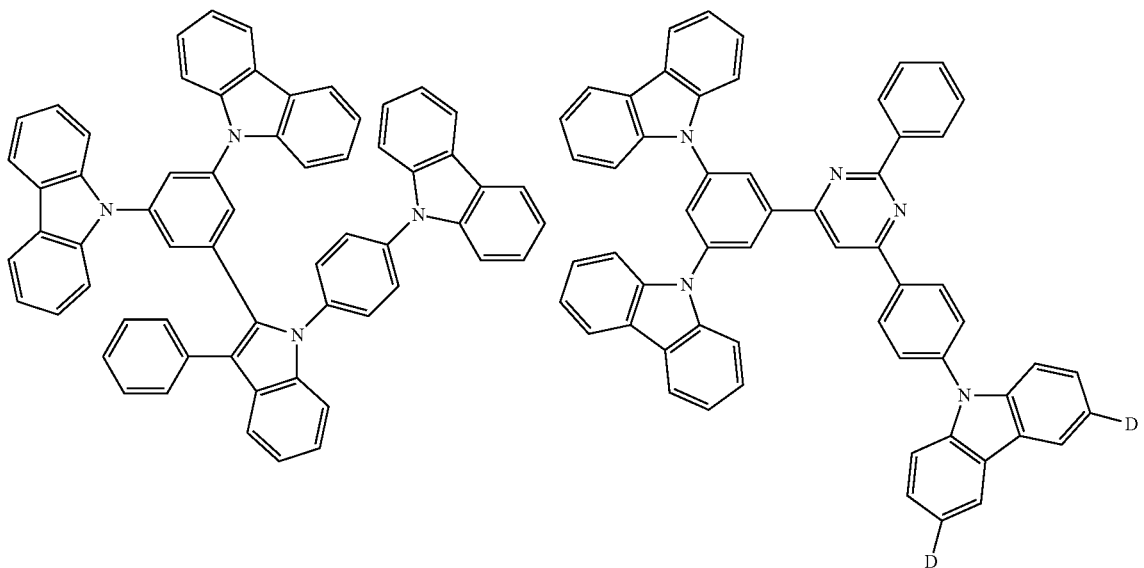

-continued
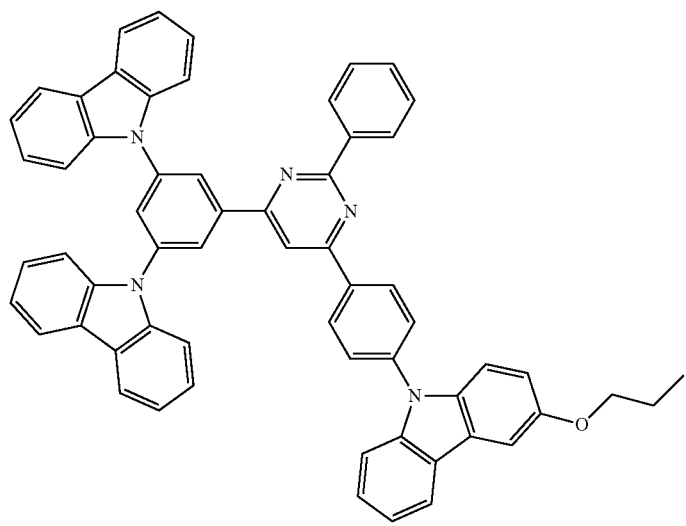
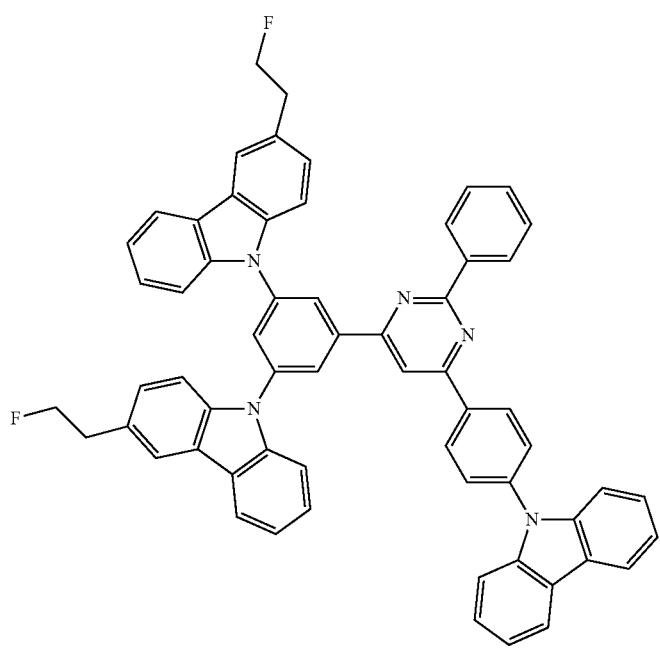

-continued
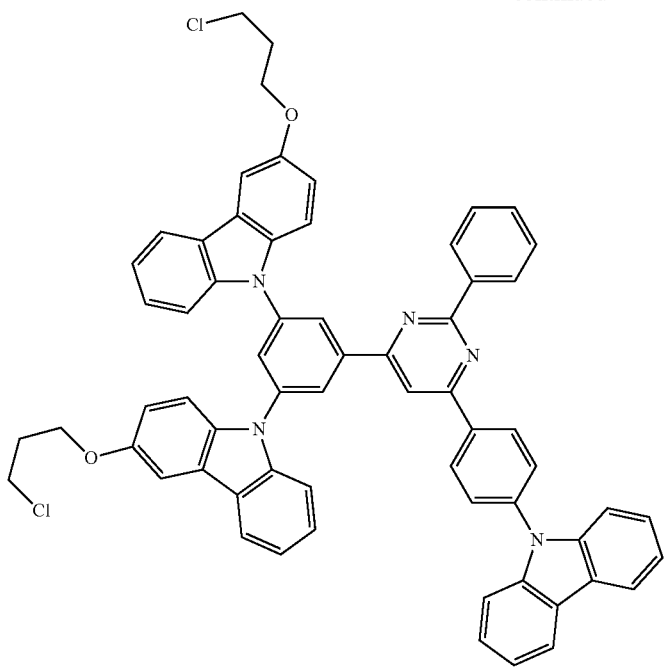
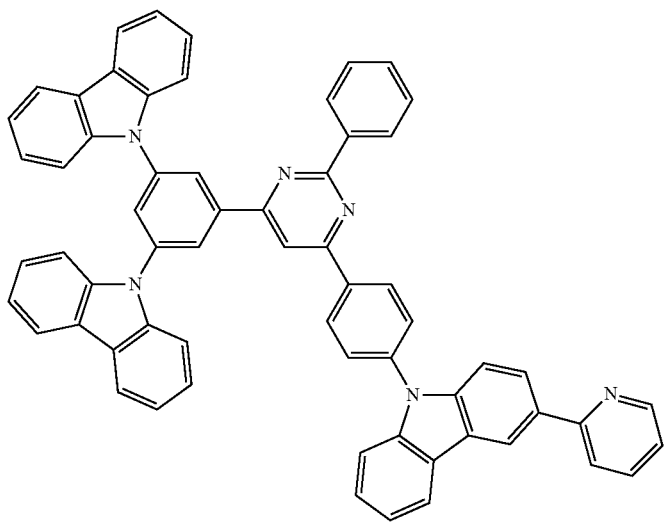
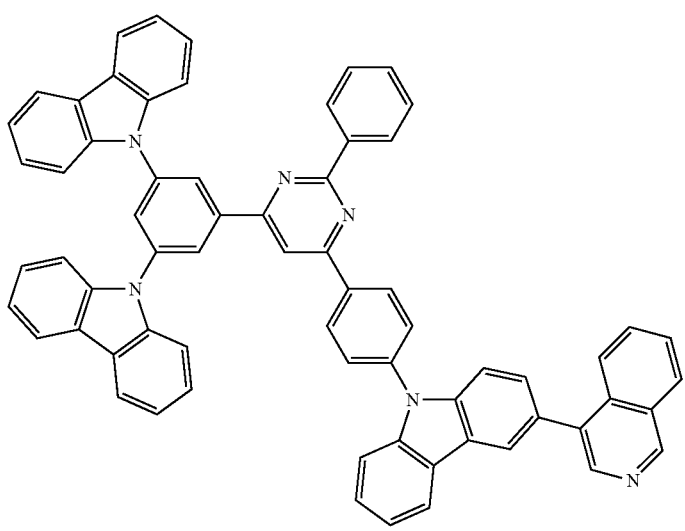

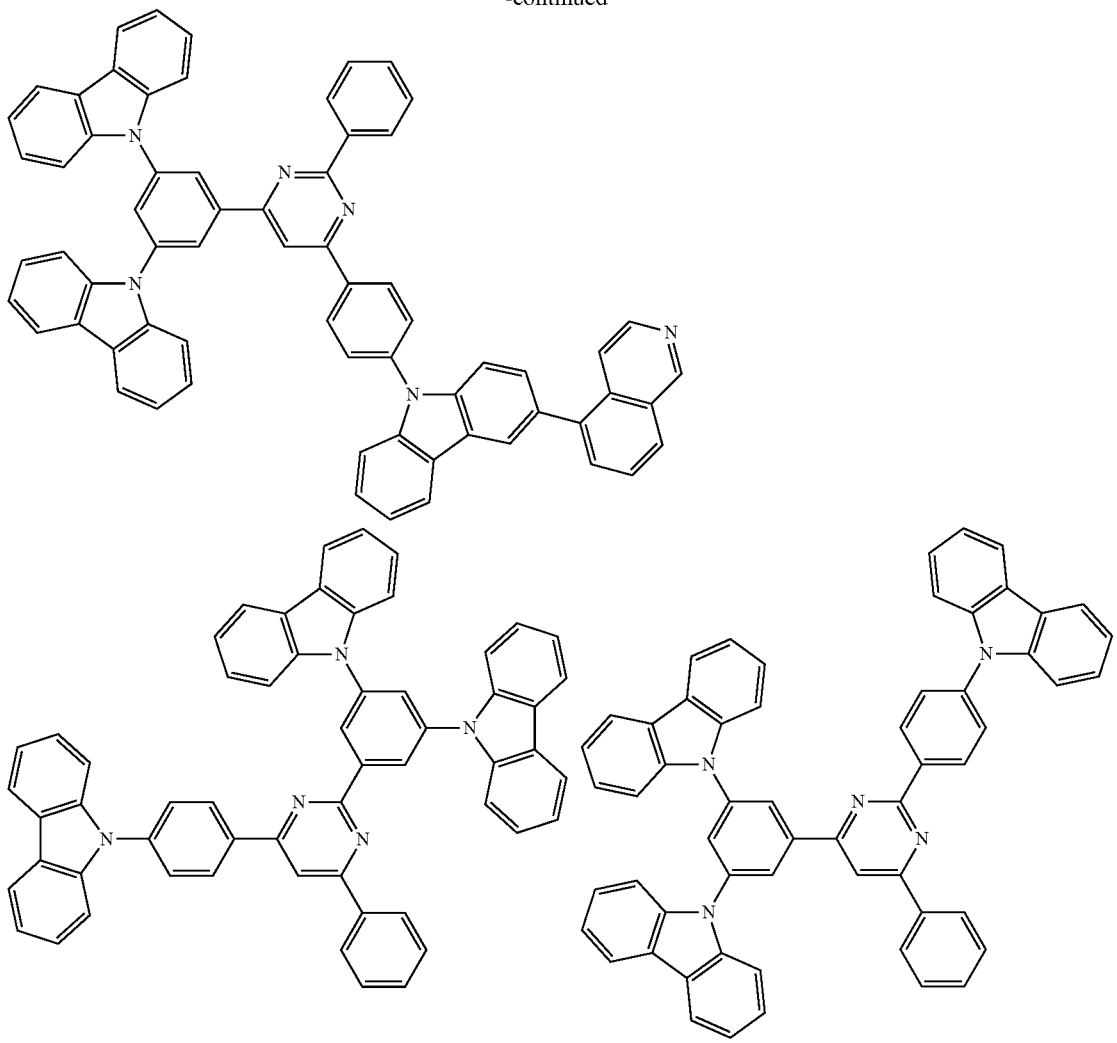

The organic EL device according to the exemplary embodiment of the invention preferably includes an electron transporting layer. The electron transporting layer may preferably contain the organic EL device material according to the exemplary embodiment of the invention.

The organic EL device according to the exemplary embodiment of the invention preferably includes at least one of an electron transporting layer and a hole blocking layer. The at least one of the electron transporting layer and the hole blocking layer may preferably contain the organic EL device material according to the exemplary embodiment of the invention.

The organic EL device according to the exemplary embodiment of the invention preferably includes a hole transporting layer (hole injecting layer). The hole transporting layer (hole injecting layer) may preferably contain the organic EL device material according to the exemplary embodiment of the invention.

Phosphorescent Material

In the exemplary embodiment of the invention, the phosphorescent material preferably contains a metal complex, and the metal complex preferably has a metal atom selected from Ir, Pt, Os, Au, Cu, Re and Ru, and a ligand. Particularly, the ligand preferably has an ortho-metal bond.

The phosphorescent material is preferably a compound containing a metal atom selected from Ir, Os, and Pt because such a compound, which exhibits high phosphorescence quantum yield, can further enhance external quantum efficiency of the emitting device. The phosphorescent material is more preferably a metal complex such as an iridium complex, an osmium complex or a platinum complex, among which an iridium complex and a platinum complex are more preferable and ortho metalation of an iridium complex is the most preferable.

Examples of such a preferable metal complex are shown below.

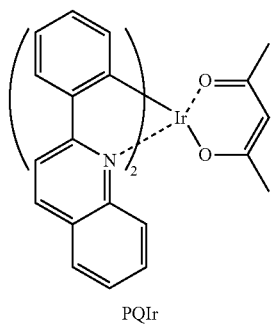

PQIr

-continued
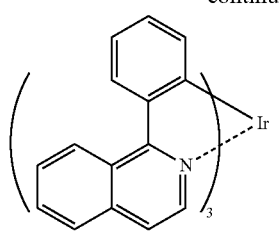
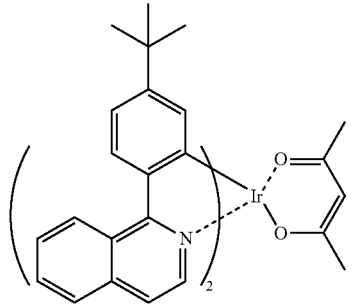
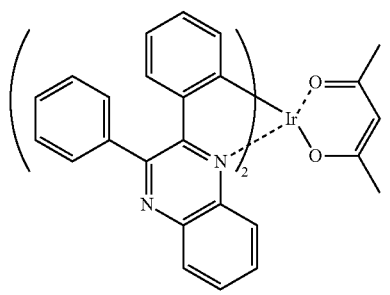
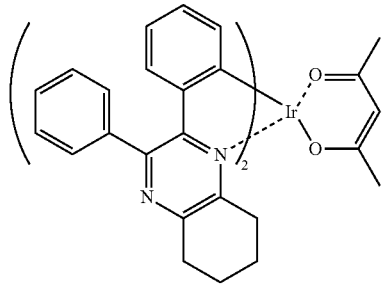
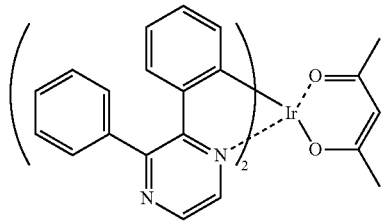
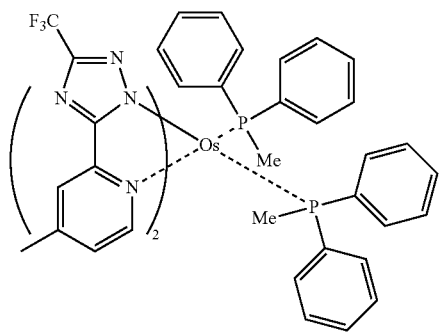
-continued
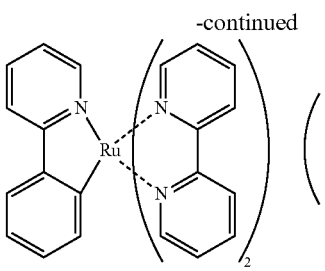
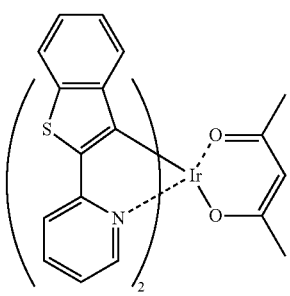
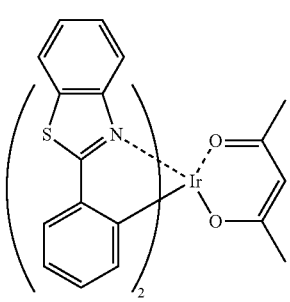
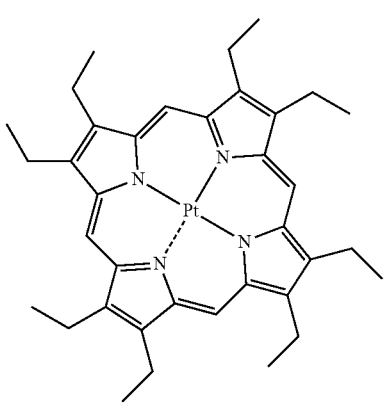
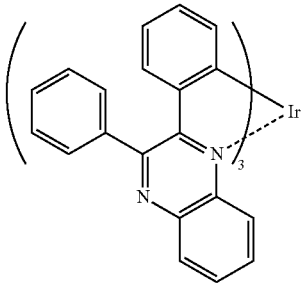

125
-continued
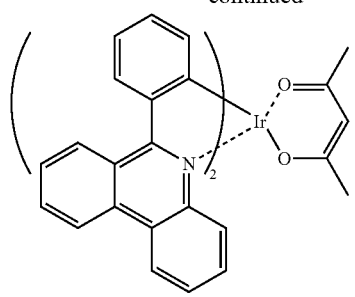
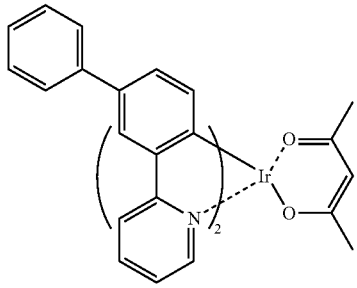
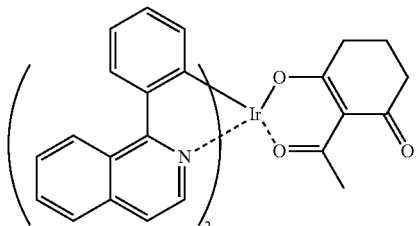
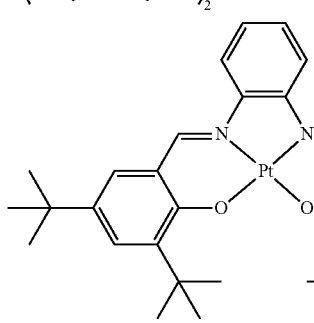
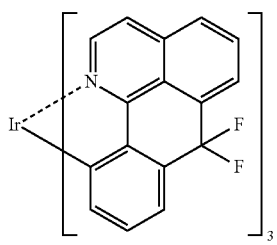
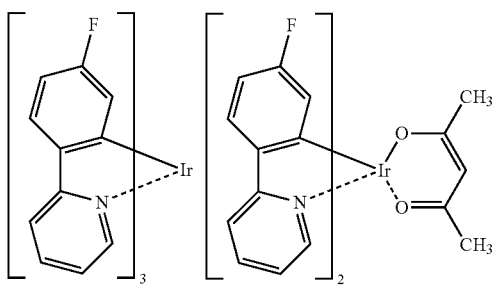
126
-continued
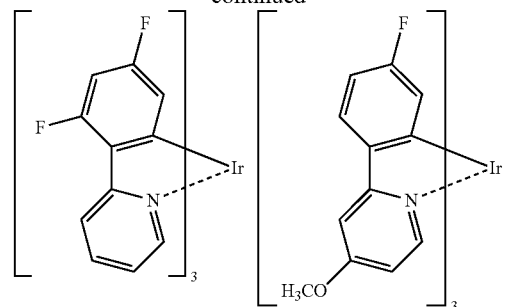
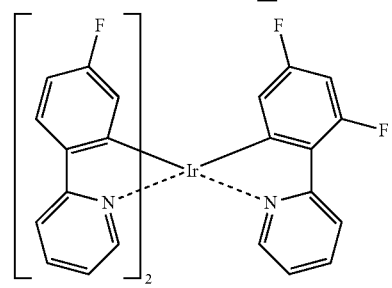
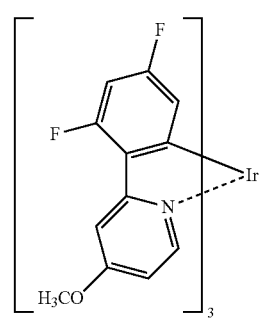
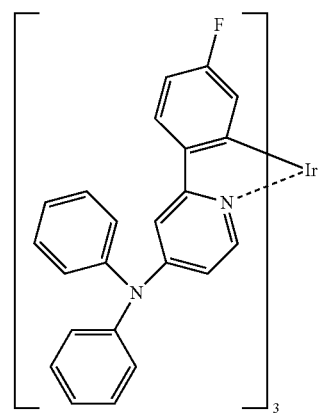
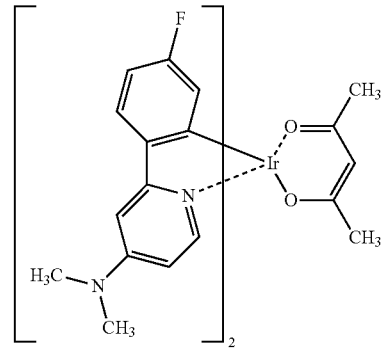

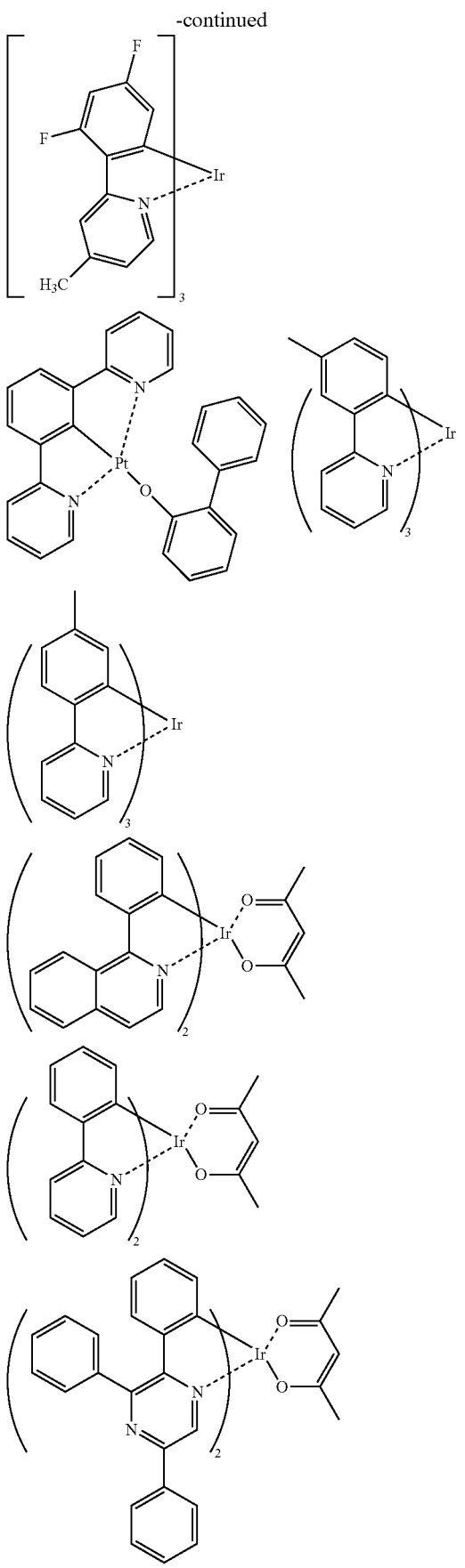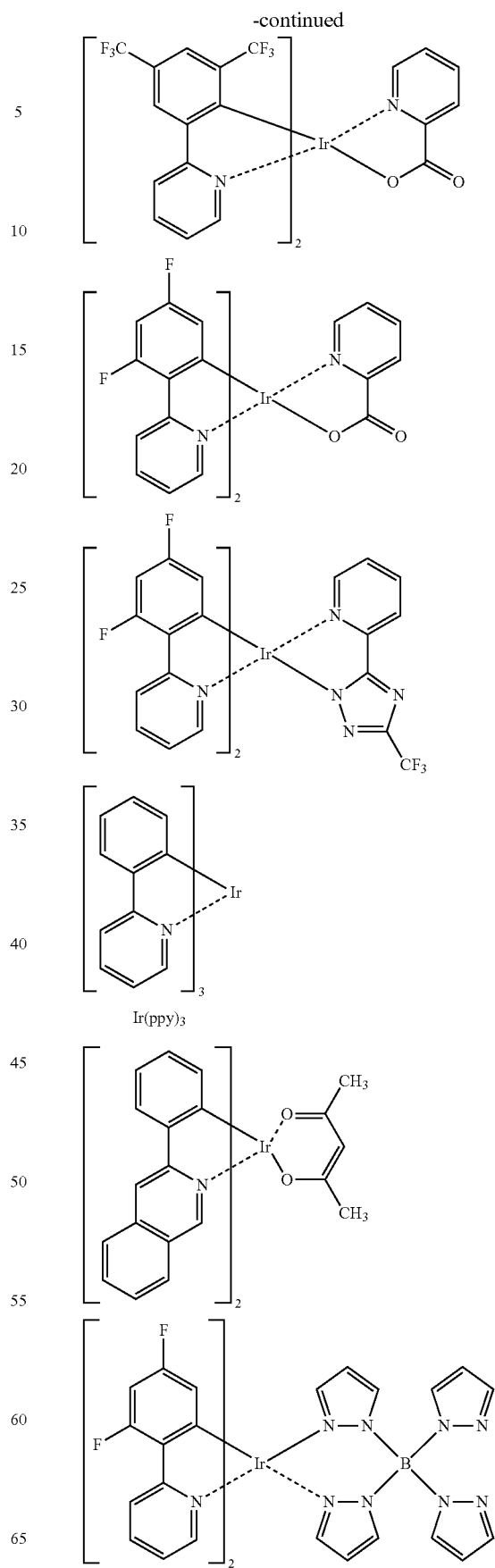

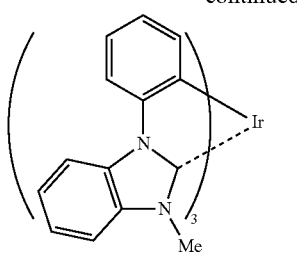
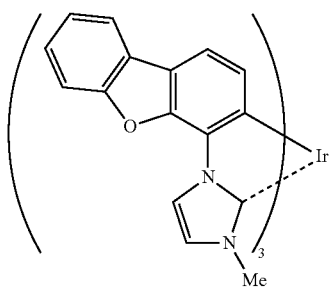
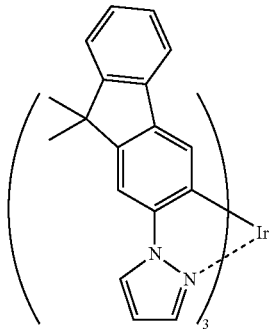
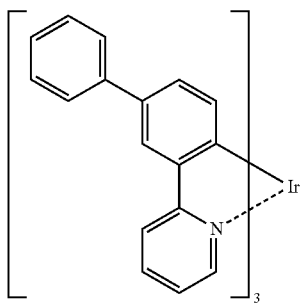
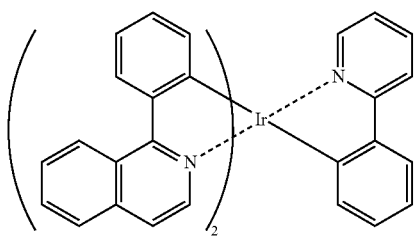
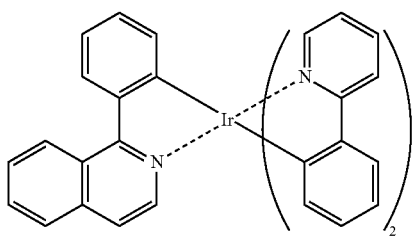
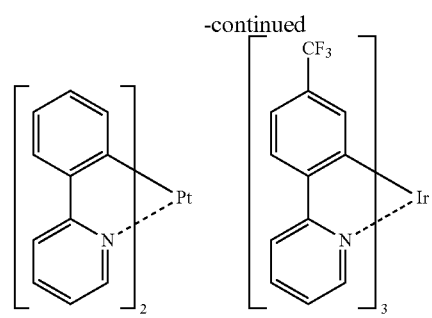
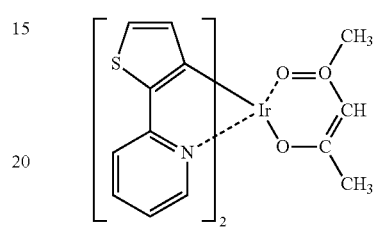
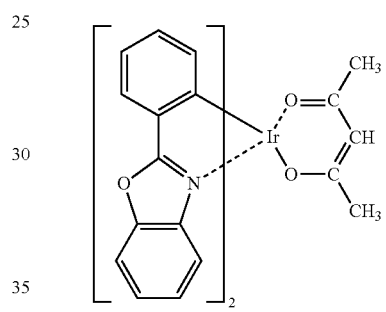
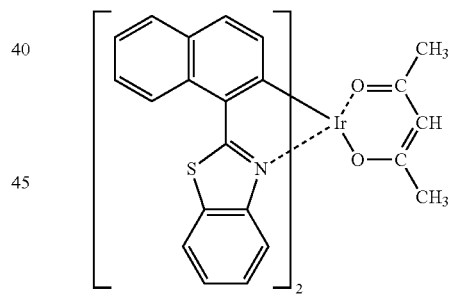
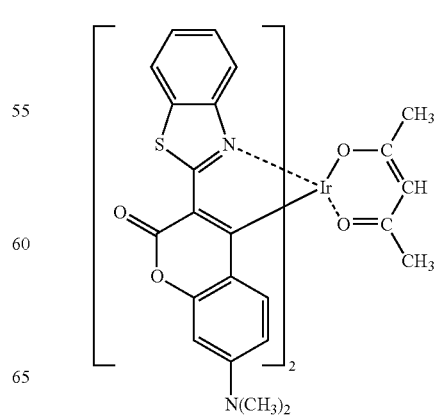

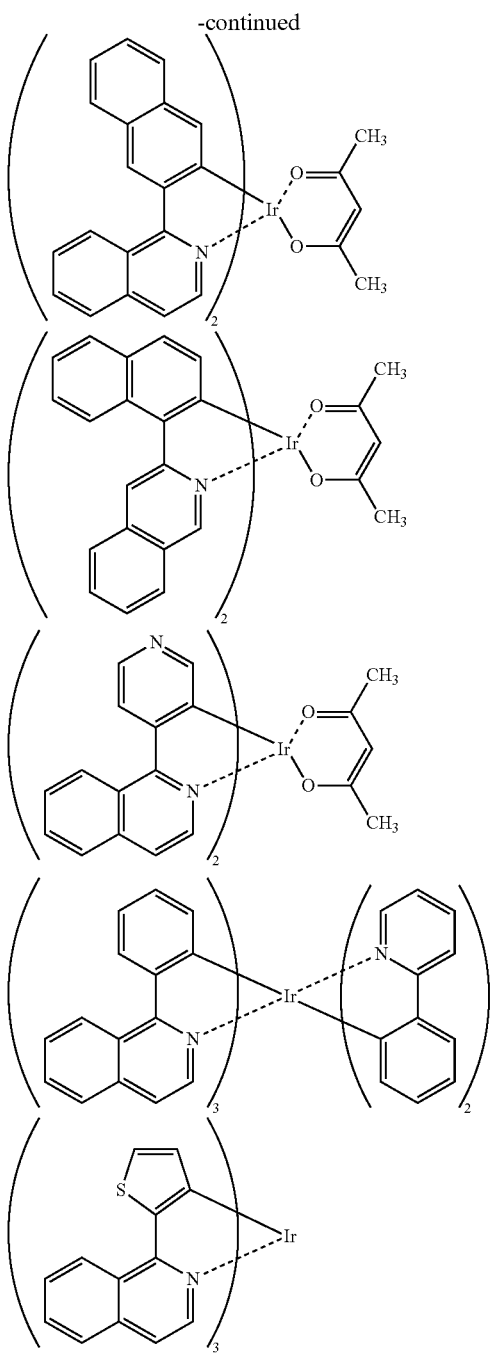

In the exemplary embodiment of the invention, the maximum wavelength of light emission of the at least one phosphorescent material contained in the emitting layer is preferably in a range of 450 nm to 720 nm.

By doping the phosphorescent material (phosphorescent dopant) having such an emission wavelength to the specific host material usable for the invention so as to form the emitting layer, the organic EL device can exhibit high efficiency.

Reduction-Causing Dopant

In the organic EL device according to the exemplary embodiment of the invention, a reduction-causing dopant may be preferably contained in an interfacial region between the cathode and the organic thin-film layer.

With this arrangement, the organic EL device can emit light with enhanced luminance intensity and have a longer lifetime.

The reduction-causing dopant may be at least one compound selected from an alkali metal, an alkali metal complex, an alkali metal compound, an alkali earth metal, an alkali earth metal complex, an alkali earth metal compound, a rare-earth metal, a rare-earth metal complex, a rare-earth metal compound and the like.

Examples of the alkali metal are Na (work function: 2.36 eV), K (work function: 2.28 eV), Rb (work function: 2.16 eV) and Cs (work function: 1.95 eV), among which a substance having a work function of 2.9 eV or less is particularly preferable. Among the above, the reduction-causing dopant is preferably K, Rb or Cs, more preferably Rb or Cs, the most preferably Cs.

Examples of the alkali earth metal are Ca (work function: 2.9 eV), Sr (work function: 2.0 eV to 2.5 eV) and Ba (work function: 2.52 eV), among which a substance having a work function of 2.9 eV or less is particularly preferable.

Examples of the rare-earth metal are Sc, Y, Ce, Tb and Yb, among which a substance having a work function of 2.9 eV or less is particularly preferable.

Since the above preferable metals have particularly high reducibility, addition of a relatively small amount of the metals to an electron injecting zone can enhance luminance intensity and lifetime of the organic EL device.

Examples of the alkali metal compound are an alkali oxide such as $Li_2O$, $Cs_2O$ or $K_2O$ and an alkali halogenide such as LiF, NaF, CsF or KF, among which LiF, $Li_2O$ and NaF are preferable.

Examples of the alkali earth metal compound are BaO, SrO, CaO, and a mixture thereof such as $Ba_xSr_{1-x}O$ (0<x<1) or $Ba_xCa_{1-x}O$ (0<x<1), among which BaO, SrO and CaO are preferable.

Examples of the rare-earth metal compound are $YbF_3$, $ScF_3$, $ScO_3$, $Y_2O_3$, $Ce_2O_3$, $GdF_3$ and $TbF_3$, among which $YbF_3$, $ScF_3$ and $TbF_3$ are preferable.

The alkali metal complex, the alkali earth metal complex and the rare-earth metal complex are not particularly limited, as long as at least one of alkali metal ion, alkali earth metal ion and rare-earth metal ion is contained therein as metal ion. A ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The reduction-causing dopant is added to preferably form a layer or an island pattern in the interfacial region. The layer of the reduction-causing dopant or the island pattern of the reduction-causing dopant is preferably formed by depositing the reduction-causing dopant by resistance heating deposition while an emitting material for forming the interfacial region or an organic substance as an electron injecting material is simultaneously deposited, so that the reduction-causing dopant is dispersed in the organic substance. Dispersion concentration at which the reduction-causing dopant is dispersed in the organic substance is a mole ratio (organic substance to reduction-causing dopant) of 100:1 to 1:100, preferably 5:1 to 1:5.

When the reduction-causing dopant forms the layer, the emitting material or the electron injecting material for forming the organic layer of the interfacial region is initially layered, and the reduction-causing dopant is subsequently deposited singularly thereon by resistance heating deposition to form a preferably 0.1 nm to 15 nm-thick layer.

When the reduction-causing dopant forms the island pattern, the emitting material or the electron injecting material for forming the organic layer of the interfacial region is initially formed in an island shape, and the reduction-causing dopant is subsequently deposited singularly thereon by resistance heating deposition to form a preferably 0.05 nm to 1 nm-thick island shape.

A ratio of the main component to the reduction-causing dopant in the organic EL device according to the exemplary embodiment of the invention is preferably a mole ratio (main component to reduction-causing dopant) of 5:1 to 1:5, more preferably 2:1 to 1:2.

Electron Injecting Layer and Electron Transporting Layer

The electron injecting layer or the electron transporting layer, which aids injection of the electrons into the emitting layer, has a high electron mobility. The electron injecting layer is provided for adjusting energy level, by which, for instance, sudden changes of the energy level can be reduced.

The organic EL device according to the exemplary embodiment of the invention preferably includes the electron injecting layer between the emitting layer and the cathode. The electron injecting layer preferably contains a nitrogen-containing cyclic derivative as the main component. The electron injecting layer may serve also as the electron transporting layer.

It should be noted that "as the main component" means that the nitrogen-containing cyclic derivative is contained in the electron injecting layer at a content of 50 mass % or more.

A preferable example of an electron transporting material for forming the electron injecting layer is an aromatic heterocyclic compound having in the molecule at least one heteroatom. Particularly, a nitrogen-containing cyclic derivative is preferable. The nitrogen-containing cyclic derivative is preferably an aromatic ring having a nitrogen-containing six-membered or five-membered ring skeleton, or a fused aromatic cyclic compound having a nitrogen-containing six-membered or five-membered ring skeleton.

A preferable example of the nitrogen-containing cyclic derivative is a nitrogen-containing cyclic metal chelate complex represented by the following formula (A).

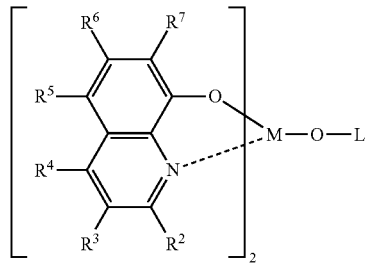

(A)

In the formula (A), $R^2$ to $R^7$ each independently represent a hydrogen atom, a halogen atom, an oxy group, an amino group, a hydrocarbon group having 1 to 40 carbon atoms, an alkoxy group, an aryloxy group, an alkoxycarbonyl group or an aromatic heterocyclic group. $R^2$ to $R^7$ may be substituted or unsubstituted.

Examples of the halogen atom are fluorine, chlorine, bromine and iodine. Examples of a substituted or unsubstituted amino group are an alkylamino group, an arylamino group and an aralkylamino group.

The alkoxycarbonyl group is represented by —COOY'. Examples of Y' are the same as the examples of the alkyl group. The alkylamino group and the aralkylamino group are represented by —NQ$^1$Q$^2$. Examples for each of Q$^1$ and Q$^2$ are the same as the examples described in relation to the alkyl group and the aralkyl group, and preferable examples for each of Q$^1$ and Q$^2$ are also the same as those described in relation to the alkyl group and the aralkyl group.

The arylamino group is represented by —NAr$^1$Ar$^2$. Examples for each of Ar$^1$ and Ar$^2$ are the same as the examples described in relation to the aromatic hydrocarbon group.

M represents aluminum (Al), gallium (Ga) or indium (In), among which In is preferable.

L in the formula (A) represents a group represented by the following formula (A') or the following formula (A").

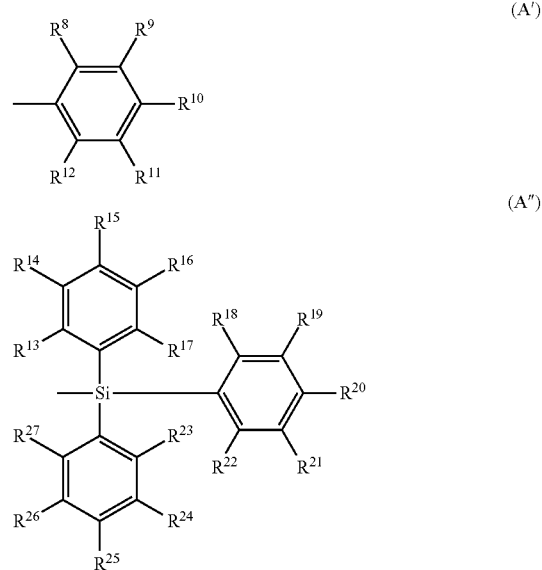

In the formula (A'), $R^8$ to $R^{12}$ each independently represent a hydrogen atom or a substituted or unsubstituted hydrocarbon group having 1 to 40 carbon atoms. Adjacent groups may form a cyclic structure. In the formula (A"), $R^{13}$ to $R^{27}$ each independently represent a hydrogen atom or a substituted or unsubstituted hydrocarbon group having 1 to 40 carbon atoms. Adjacent groups may form a cyclic structure.

Examples of the hydrocarbon group having 1 to 40 carbon atoms represented by each of $R^8$ to $R^{12}$ and $R^{13}$ to $R^{27}$ in the formulae (A') and (A") are the same as those of $R^2$ to $R^7$.

Examples of a divalent group formed when an adjacent set of $R^8$ to $R^{12}$ and $R^{13}$ to $R^{27}$ forms a cyclic structure are a tetramethylene group, a pentamethylene group, a hexamethylene group, a diphenylmethane-2,2'-diyl group, a diphenylethane-3,3'-diyl group and a diphenylpropane-4,4'-diyl group.

In the exemplary embodiment of the invention, the aromatic compound represented by the formulae (1) and (3) (or (4) and (6)) is preferably contained as the electron transporting layer.

As an electron transport compound for the electron injecting layer or the electron transporting layer, 8-hydroxyquinoline or a metal complex of its derivative, an oxadiazole derivative, or a nitrogen-containing heterocyclic derivative is preferable. An example of the 8-hydroxyquinoline or the metal complex of its derivative is a metal chelate oxinoid compound containing a chelate of oxine (typically 8-quinolinol or 8-hydroxyquinoline). For instance, tris(8-quinolinol) aluminum can be used. Examples of the oxadiazole derivative are as follows.

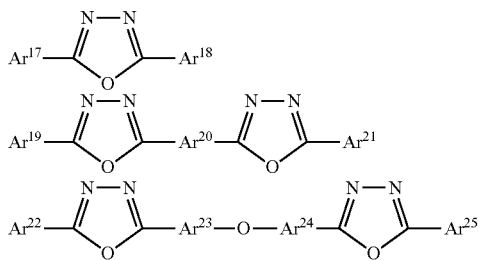

In the formula, $Ar^{17}$, $Ar^{18}$, $Ar^{19}$, $Ar^{21}$, $A^{22}$ and $A^{25}$ each represent a substituted or unsubstituted aromatic hydrocarbon group or fused aromatic hydrocarbon group. $Ar^{17}$, $Ar^{19}$ and $Ar^{22}$ may be the same as or different from $Ar^{18}$, $Ar^{21}$ and $Ar^{25}$, respectively. Examples of the aromatic hydrocarbon group or fused aromatic hydrocarbon group are a phenyl group, naphthyl group, biphenyl group, anthranil group, perylenyl group and pyrenyl group. Examples of the substituent therefor are an alkyl group having 1 to 10 carbon atoms, alkoxy group having 1 to 10 carbon atoms and cyano group.

$Ar^{20}$, $Ar^{23}$ and $Ar^{24}$ each represent a substituted or unsubstituted divalent aromatic hydrocarbon group or fused aromatic hydrocarbon group. $Ar^{23}$ and $Ar^{24}$ may be mutually the same or different.

Examples of the divalent aromatic hydrocarbon group or fused aromatic hydrocarbon group are a phenylene group, naphthylene group, biphenylene group, anthranylene group, perylenylene group and pyrenylene group. Examples of the substituent therefor are an alkyl group having 1 to 10 carbon atoms, alkoxy group having 1 to 10 carbon atoms and cyano group.

Such an electron transport compound is preferably an electron transport compound that can be favorably formed into a thin film(s). Examples of the electron transport compound are as follows.

An example of the nitrogen-containing heterocyclic derivative as the electron transport compound is a nitrogen-containing heterocyclic derivative that is not a metal complex, the derivative being formed of an organic compound represented by either one of the following formulae. Examples of the nitrogen-containing heterocyclic derivative are five-membered ring or six-membered ring derivative having a skeleton represented by the formula (A) and a derivative having a structure represented by the formula (B).

(A)

(B)

In the formula (B), X represents a carbon atom or a nitrogen atom. $Z_1$ and $Z_2$ each independently represent an atom group capable of forming a nitrogen-containing heterocycle.

More preferably, the nitrogen-containing heterocyclic derivative is an organic compound having a nitrogen-containing aromatic polycyclic group having a five-membered ring or six-membered ring. Further, when the nitrogen-containing heterocyclic derivative is such a nitrogen-containing aromatic polycyclic group that contains plural nitrogen atoms, the nitrogen-containing heterocyclic derivative is preferably a nitrogen-containing aromatic polycyclic organic compound having a skeleton formed by a combination of the skeletons respectively represented by the formulae (A) and (B), or by a combination of the skeletons respectively represented by the formulae (A) and (C).

(C)

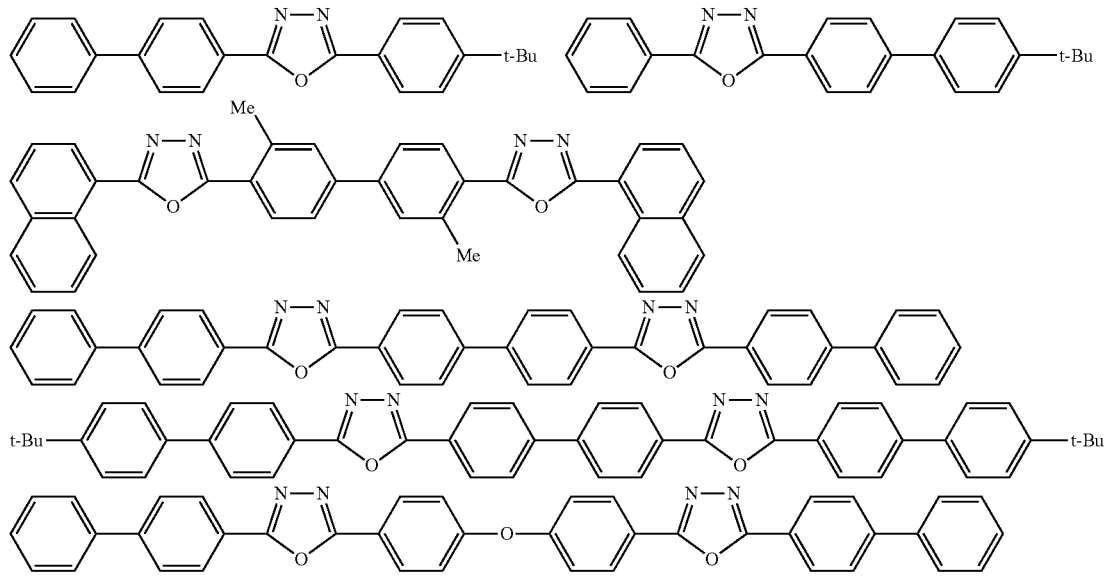

A nitrogen-containing group of the nitrogen-containing aromatic polycyclic organic compound is selected from nitrogen-containing heterocyclic groups respectively represented by, for instance, the following formulae.

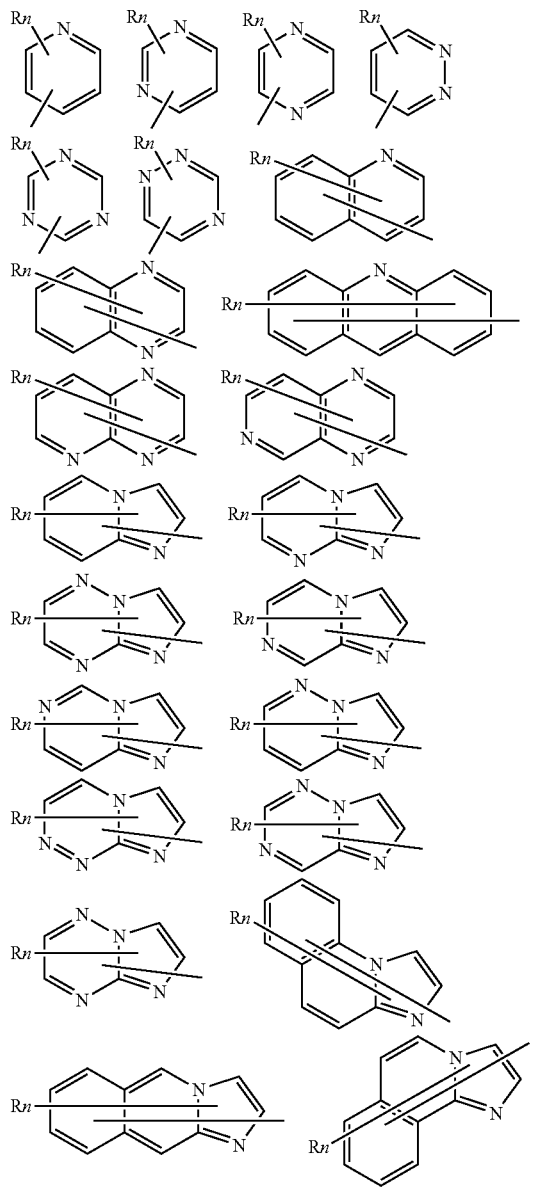

In the formulae: R represents an aromatic hydrocarbon group or fused aromatic hydrocarbon group having 6 to 40 carbon atoms, aromatic heterocyclic group or fused aromatic heterocyclic group having 3 to 40 carbon atoms, alkyl group having 1 to 20 carbon atoms or alkoxy group having 1 to 20 carbon atoms; and n represents an integer of 0 to 5. When n is an integer of 2 or more, plural R may be mutually the same or different.

A preferable specific compound is a nitrogen-containing heterocyclic derivative represented by the following formula.

In the formula:

HAr represents a substituted or unsubstituted nitrogen-containing heterocyclic group having 3 to 40 carbon atoms;

$L^1$ represents a single bond, substituted or unsubstituted aromatic hydrocarbon group or fused aromatic hydrocarbon group having 6 to 40 carbon atoms, or substituted or unsubstituted aromatic heterocyclic group or fused aromatic heterocyclic group having 3 to 40 carbon atoms;

$Ar^1$ represents a substituted or unsubstituted divalent aromatic hydrocarbon group having 6 to 40 carbon atoms; and $Ar^2$ represents a substituted or unsubstituted aromatic hydrocarbon group or fused aromatic hydrocarbon group having 6 to 40 carbon atoms, or substituted or unsubstituted aromatic heterocyclic group or fused aromatic heterocyclic group having 3 to 40 carbon atoms.

HAr is exemplarily selected from the following group.

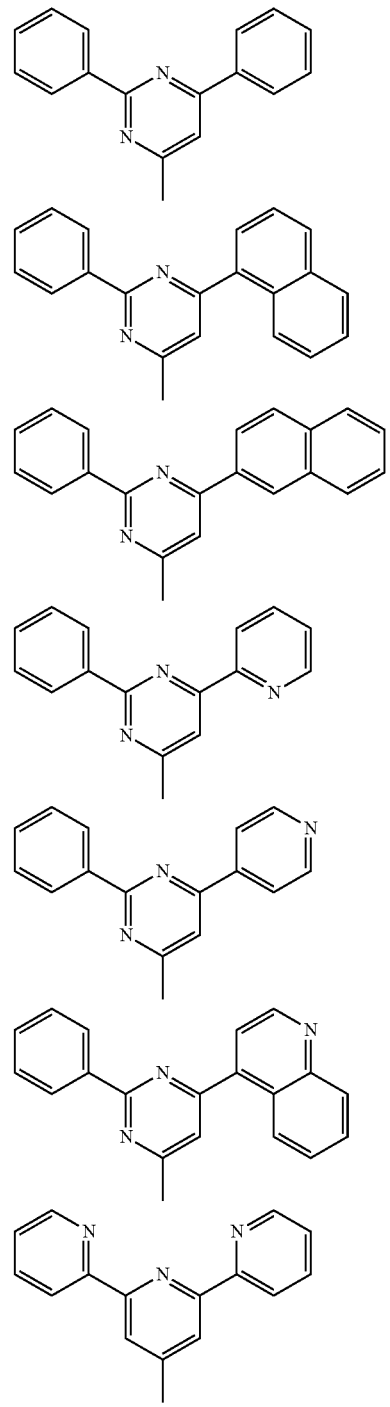

-continued

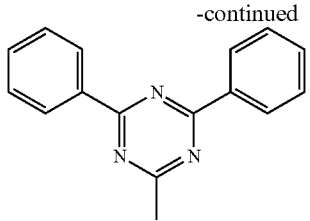

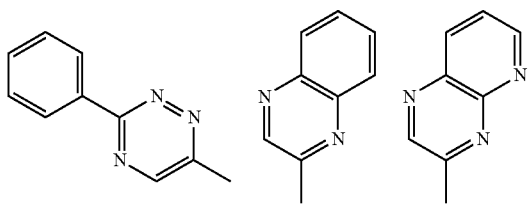

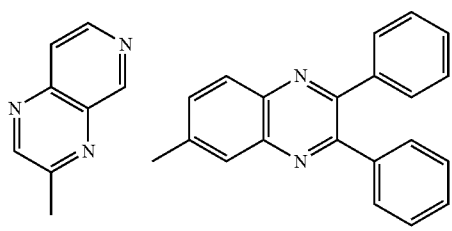

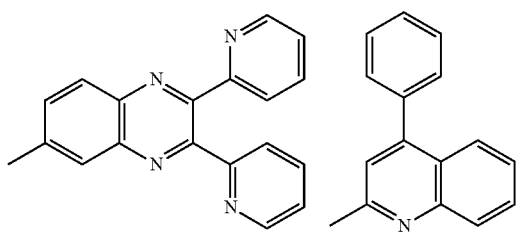

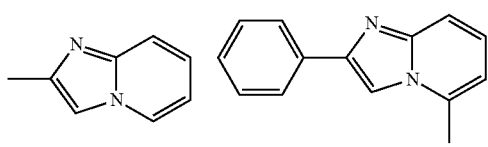

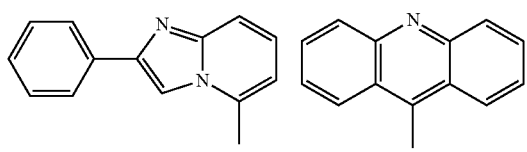

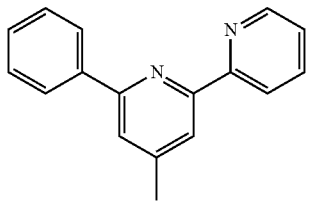

$L^1$ is exemplarily selected from the following group.

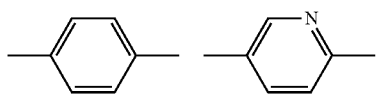

$Ar^1$ is exemplarily selected from the following arylanthranil groups.

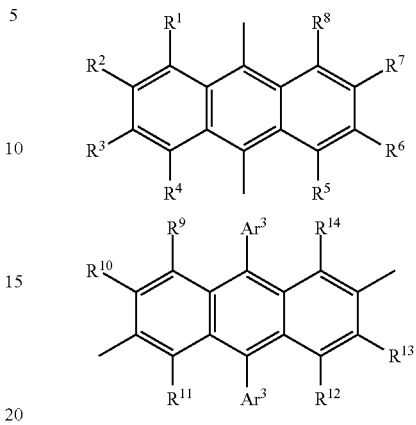

In the formulae:

$R^1$ to $R^{14}$ each independently represent a hydrogen atom, halogen atom, alkyl group having 1 to 20 carbon atoms, alkoxy group having 1 to 20 carbon atoms, aryloxy group having 6 to 40 carbon atoms, substituted or unsubstituted aromatic hydrocarbon group or fused aromatic hydrocarbon group having 6 to 40 carbon atoms or aromatic heterocyclic group or fused aromatic heterocyclic group having 3 to 40 carbon atoms; and $Ar^3$ represents a substituted or unsubstituted aromatic hydrocarbon group or fused aromatic hydrocarbon group having 6 to 40 carbon atoms or aromatic heterocyclic group or fused aromatic heterocyclic group having 3 to 40 carbon atoms.

The nitrogen-containing heterocyclic derivative may be a nitrogen-containing heterocyclic derivative in which $R^1$ to $R^8$ each represent a hydrogen atom.

$Ar^2$ is exemplarily selected from the following group.

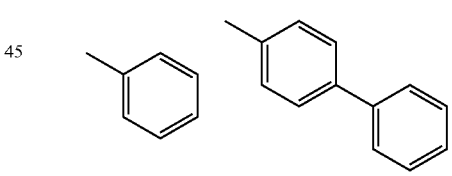

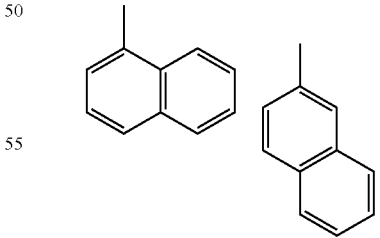

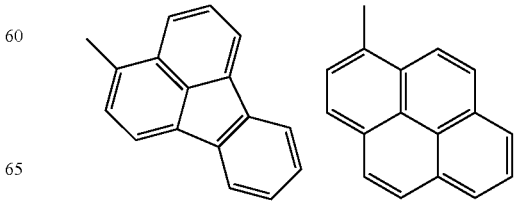

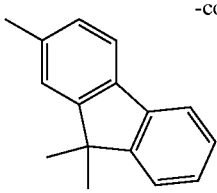

Other than the above, the following compound can be favorably used as the nitrogen-containing aromatic polycyclic organic compound (i.e., the electron transport compound).

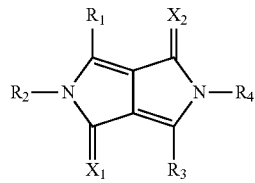

In the formula, $R_1$ to $R_4$ each independently represent a hydrogen atom, substituted or unsubstituted aliphatic group, substituted or unsubstituted alicyclic group, substituted or unsubstituted carbocyclic aromatic cyclic group, or substituted or unsubstituted heterocyclic group. $X_1$ and $X_2$ each independently represent an oxygen atom, sulfur atom or dicyanomethylene group.

The following compound can also be favorably used as the electron transport compound.

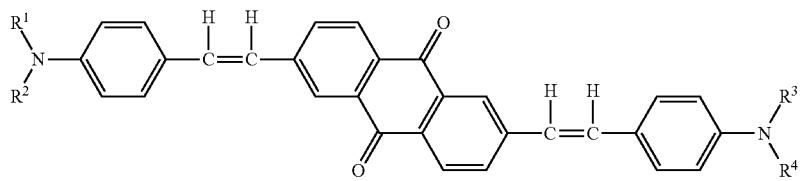

In the formula, $R^1$, $R^2$, $R^3$ and $R^4$, which may be mutually the same or different, each represent an aromatic hydrocarbon group or fused aromatic hydrocarbon group represented by the following formula.

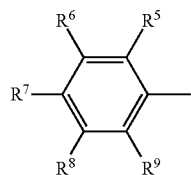

In the formula, $R^5$, $R^6$, $R^7$, $R^8$ and $R^9$, which may be mutually the same or different, each represent a hydrogen atom, saturated or unsaturated alkoxy group, alkyl group, amino group or alkylamino group. At least one of $R^5$, $R^6$, $R^7$, $R^8$ and $R^9$ represents a saturated or unsaturated alkoxy group, alkyl group, amino group or alkylamino group.

The electron transport compound may be a polymer compound containing the nitrogen-containing heterocyclic group or nitrogen-containing heterocyclic derivative.

The electron transporting layer preferably contains at least one of nitrogen-containing heterocycle derivatives respectively represented by the following formulae (201) to (203).

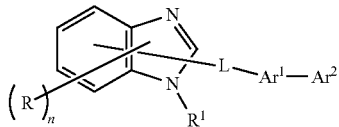

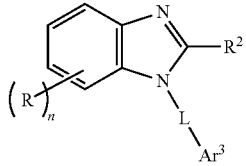

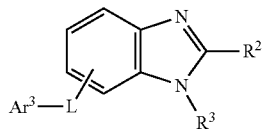

In the formulae (201) to (203), R represents a hydrogen atom, substituted or unsubstituted aromatic hydrocarbon group or fused aromatic hydrocarbon group having 6 to 60 carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms.

n represents an integer of 0 to 4.

$R^1$ represents a substituted or unsubstituted aromatic hydrocarbon group or fused aromatic hydrocarbon group having 6 to 60 carbon atoms, substituted or unsubstituted pyridyl group, substituted or unsubstituted quinolyl group, substituted or unsubstituted alkyl group having 1 to 20 carbon atoms, or alkoxy group having 1 to 20 carbon atoms.

$R^2$ and $R^3$ each independently represent a hydrogen atom, substituted or unsubstituted aromatic hydrocarbon group or fused aromatic hydrocarbon group having 6 to 60 carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms.

L represents a substituted or unsubstituted aromatic hydrocarbon group or fused aromatic hydrocarbon group having 6 to 60 carbon atoms, substituted or unsubstituted pyridinylene group, substituted or unsubstituted quinolinylene group, or substituted or unsubstituted fluorenylene group.

$Ar^1$ represents a substituted or unsubstituted aromatic hydrocarbon group or fused aromatic hydrocarbon group having 6 to 60 carbon atoms, substituted or unsubstituted pyridinylene group, or substituted or unsubstituted quinolinylene group. $Ar^2$ represents substituted or unsubstituted aromatic hydrocarbon group or fused aromatic hydrocarbon group having 6 to 60 carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atom.

Ar³ represents a substituted or unsubstituted aromatic hydrocarbon group or fused aromatic hydrocarbon group having 6 to 60 carbon atoms, substituted or unsubstituted pyridyl group, substituted or unsubstituted quinolyl group, substituted or unsubstituted alkyl group having 1 to 20 carbon atoms, substituted or unsubstituted alkoxy group having 1 to 20 carbon atoms, or a group represented by —Ar¹—Ar² (Ar¹ and Ar² may be the same as the above).

In the formulae (201) to (203), R represents a hydrogen atom, substituted or unsubstituted aromatic hydrocarbon group or fused aromatic hydrocarbon group having 6 to 60 carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms.

Although the thickness of the electron injecting layer or the electron transporting layer is not particularly limited, the thickness is preferably 1 nm to 100 nm.

The electron injecting layer preferably contains an inorganic compound such as an insulator or a semiconductor in addition to the nitrogen-containing cyclic derivative. Such an insulator or a semiconductor, when contained in the electron injecting layer, can effectively prevent a current leak, thereby enhancing electron injectability of the electron injecting layer.

As the insulator, it is preferable to use at least one metal compound selected from a group consisting of an alkali metal chalcogenide, an alkali earth metal chalcogenide, a halogenide of alkali metal and a halogenide of alkali earth metal. Forming the electron injecting layer from the alkali metal chalcogenide or the like is preferable for further enhancement of the electron injectability. Specifically, preferable examples of the alkali metal chalcogenide are $Li_2O$, $K_2O$, $Na_2S$, $Na_2Se$ and $Na_2O$, while preferable example of the alkali earth metal chalcogenide are CaO, BaO, SrO, BeO, BaS and CaSe. Preferable examples of the halogenide of the alkali metal are LiF, NaF, KF, LiCl, KCl and NaCl. Preferable examples of the halogenide of the alkali earth metal are fluorides such as $CaF_2$, $BaF_2$, $SrF_2$, $MgF_2$ and $BeF_2$, and halogenides other than the fluoride.

Examples of the semiconductor are one of or a combination of two or more of an oxide, a nitride or an oxidized nitride containing at least one element selected from Ba, Ca, Sr, Yb, Al, Ga, In, Li, Na, Cd, Mg, Si, Ta, Sb and Zn. An inorganic compound for forming the electron injecting layer is preferably a microcrystalline or amorphous semiconductor film. When the electron injecting layer is formed of such a semiconductor film, more uniform thin film can be formed, thereby reducing pixel defects such as a dark spot. Examples of such an inorganic compound are the alkali metal chalcogenide, alkali earth metal chalcogenide, halogenide of the alkali metal and halogenide of the alkali earth metal.

When the electron injecting layer contains such an insulator or such a semiconductor, the thickness thereof is preferably in a range of approximately 0.1 to 15 nm. The electron injecting layer according to the exemplary embodiment of the invention may preferably contain the above-described reduction-causing dopant.

Hole Injecting Layer and Hole Transporting Layer

The hole injecting layer or the hole transporting layer (including the hole injecting/transporting layer) preferably contains an aromatic amine compound such as an aromatic amine derivative represented by the following formula (I). Such a substance may be combined with the organic EL device material according to the exemplary embodiment of the invention for use in the emitting layer.

In the formula (I), Ar¹ to Ar⁴ each represent a substituted or unsubstituted aromatic hydrocarbon group having 6 to 50 ring carbon atoms, a substituted or unsubstituted aromatic heterocyclic group having 5 to 50 atoms for forming a ring, or a group formed by bonding the aromatic hydrocarbon group to the aromatic heterocyclic group.

Examples of the compound represented by the formula (I) are shown below. However, the compound is not limited thereto.

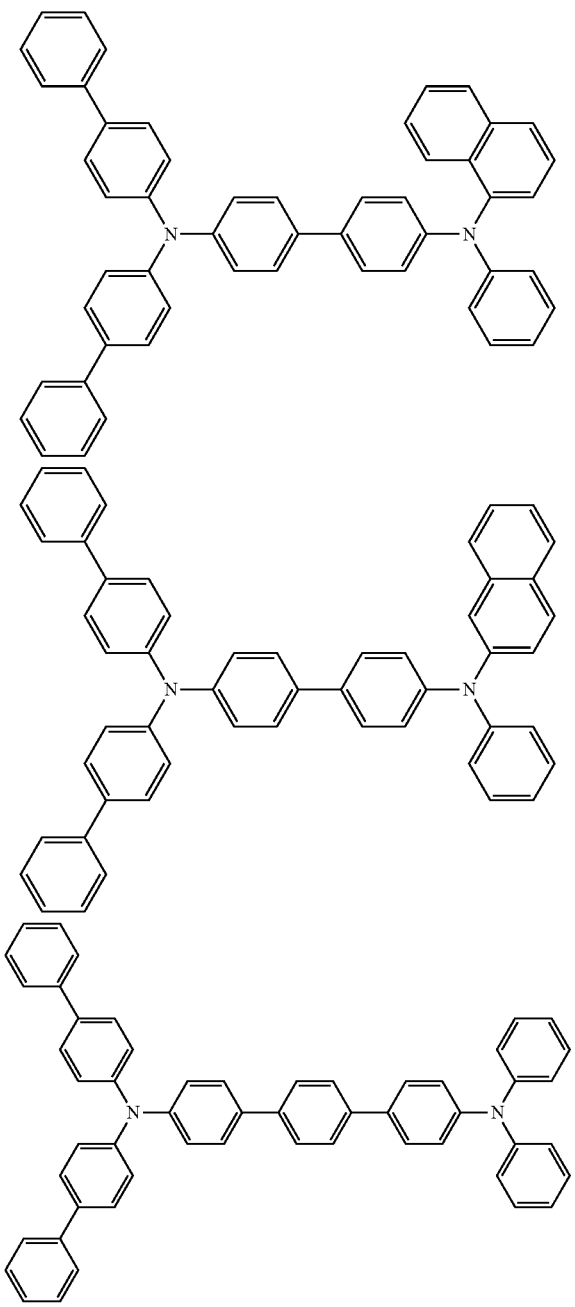

145
-continued
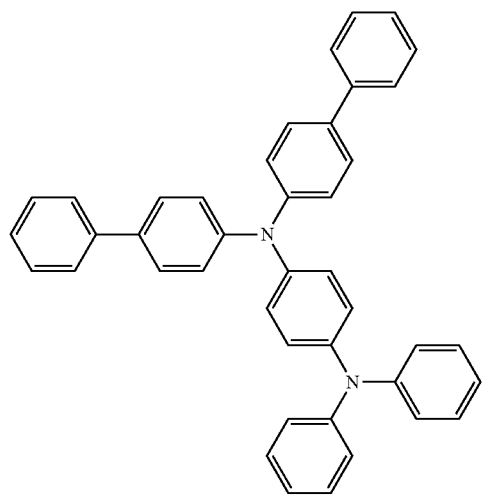
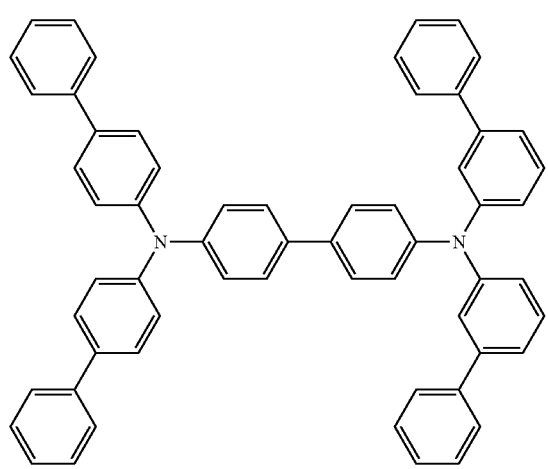
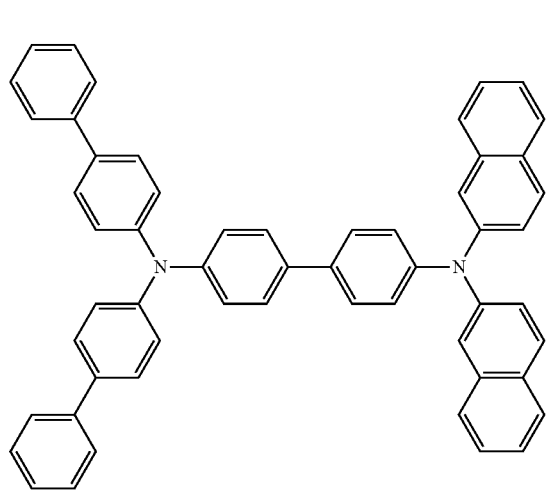
146
-continued
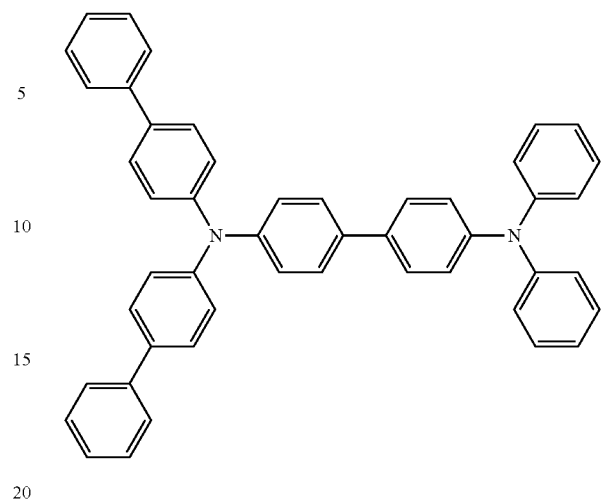
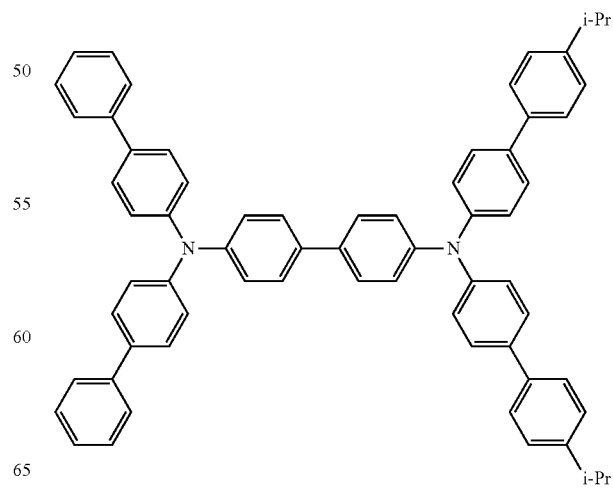

147
-continued
148
-continued
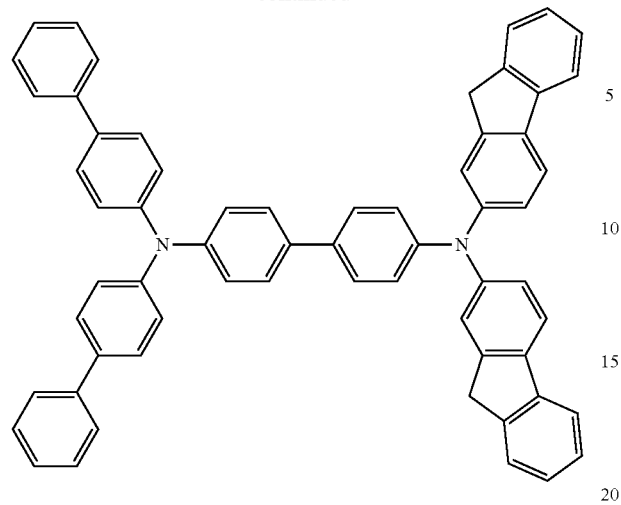
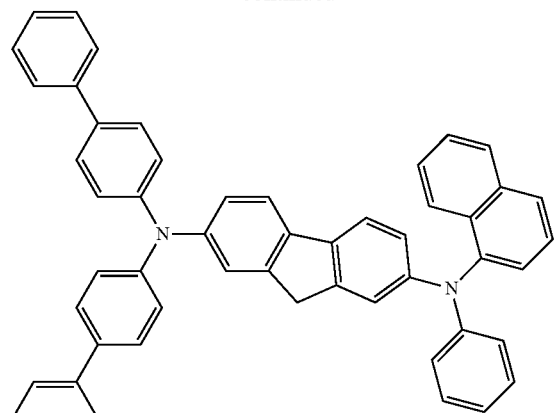
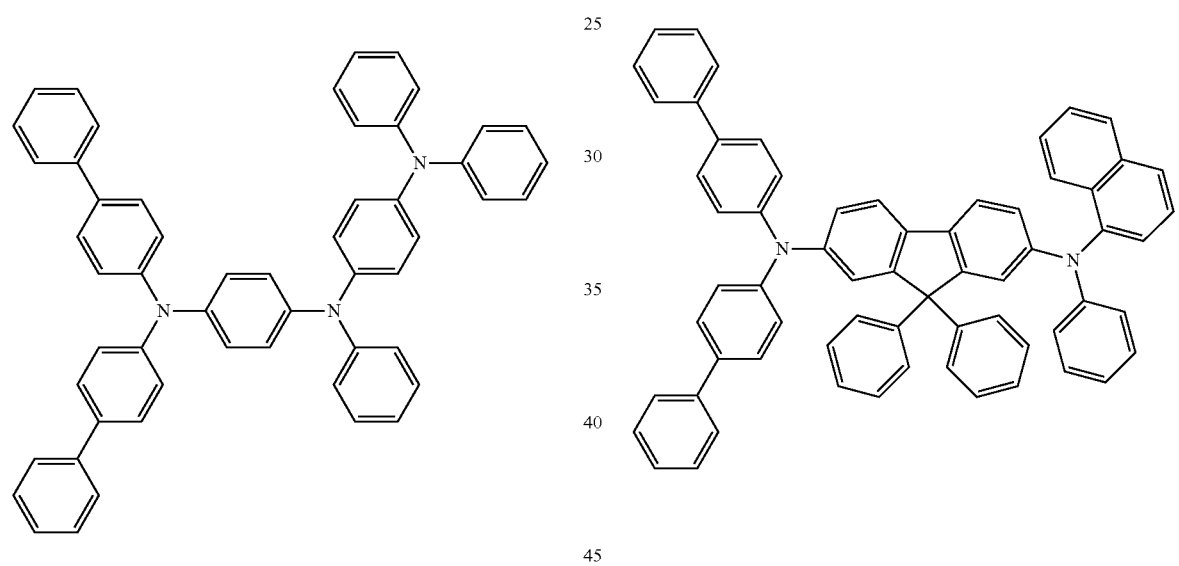
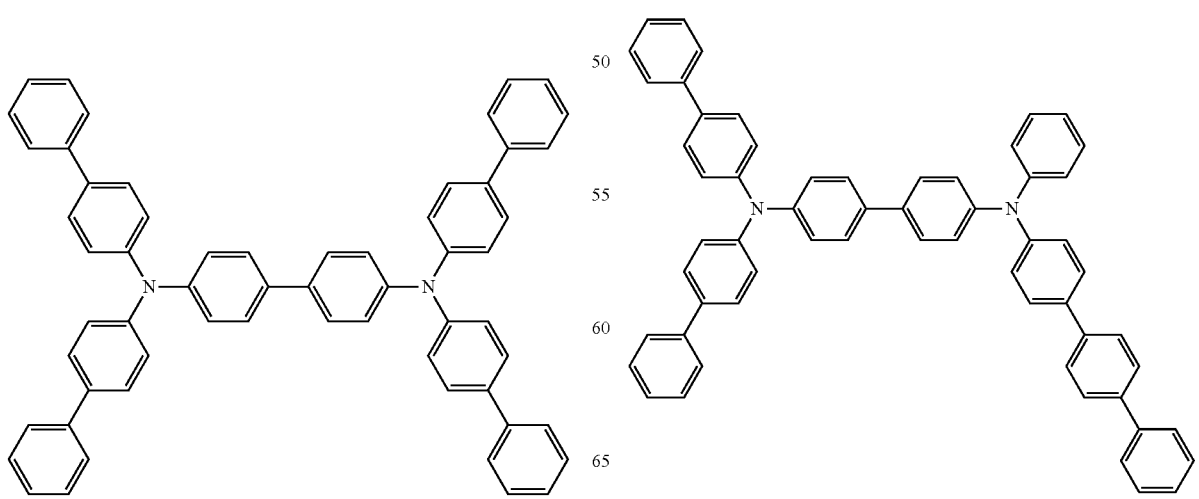

149
-continued
150
-continued
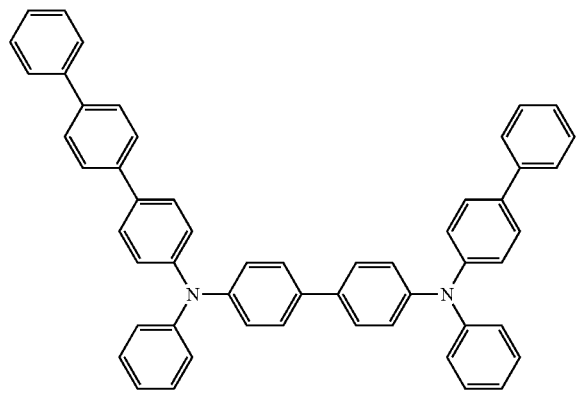
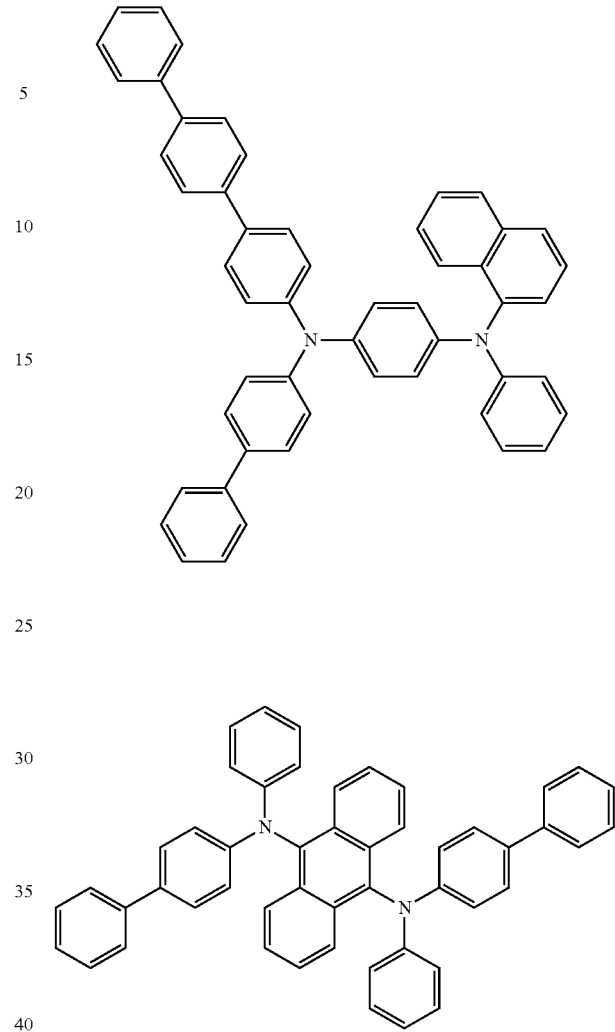
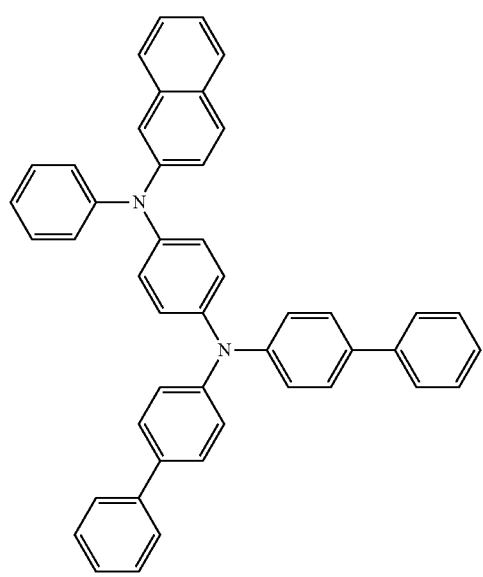
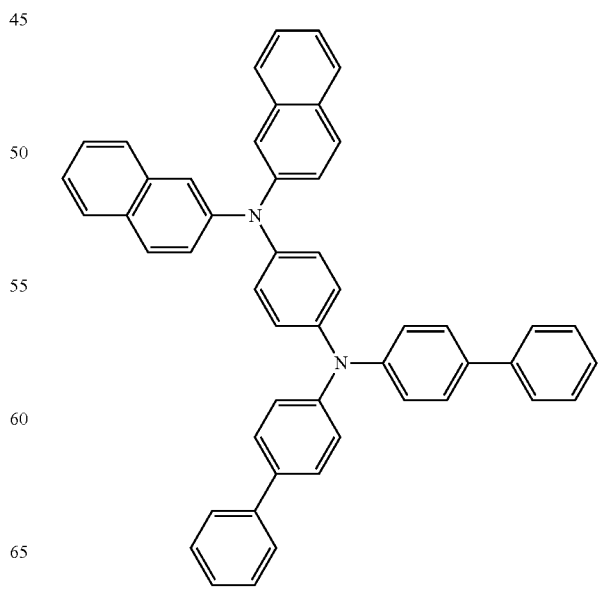

151
-continued
152
-continued
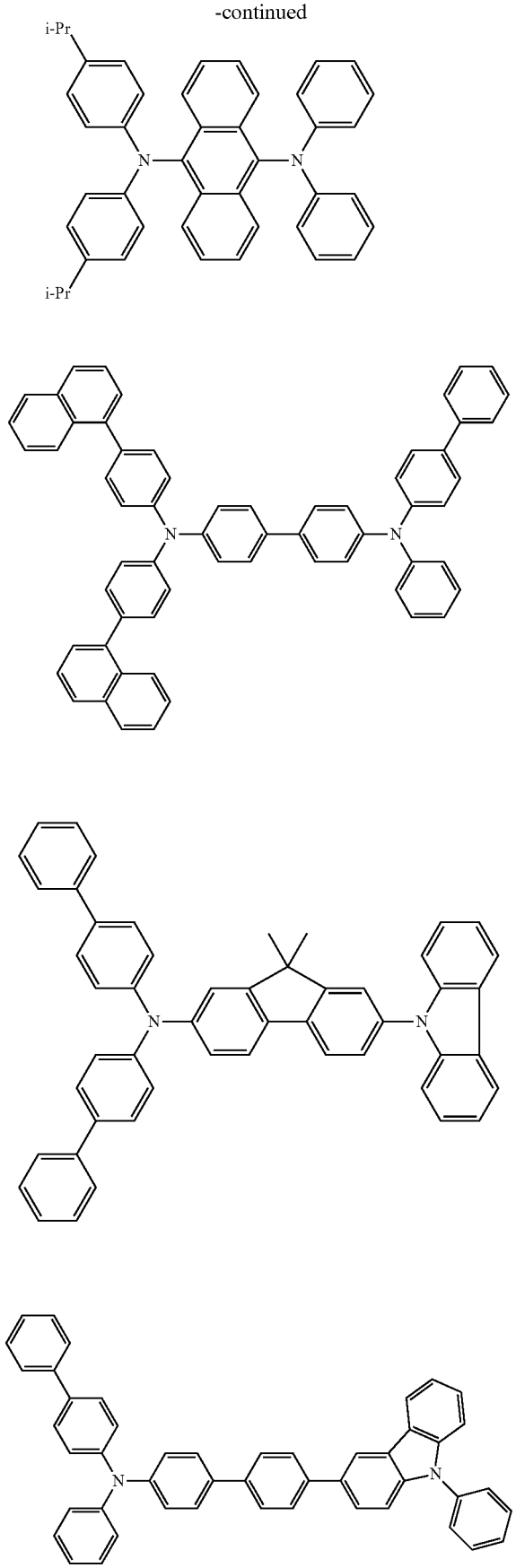
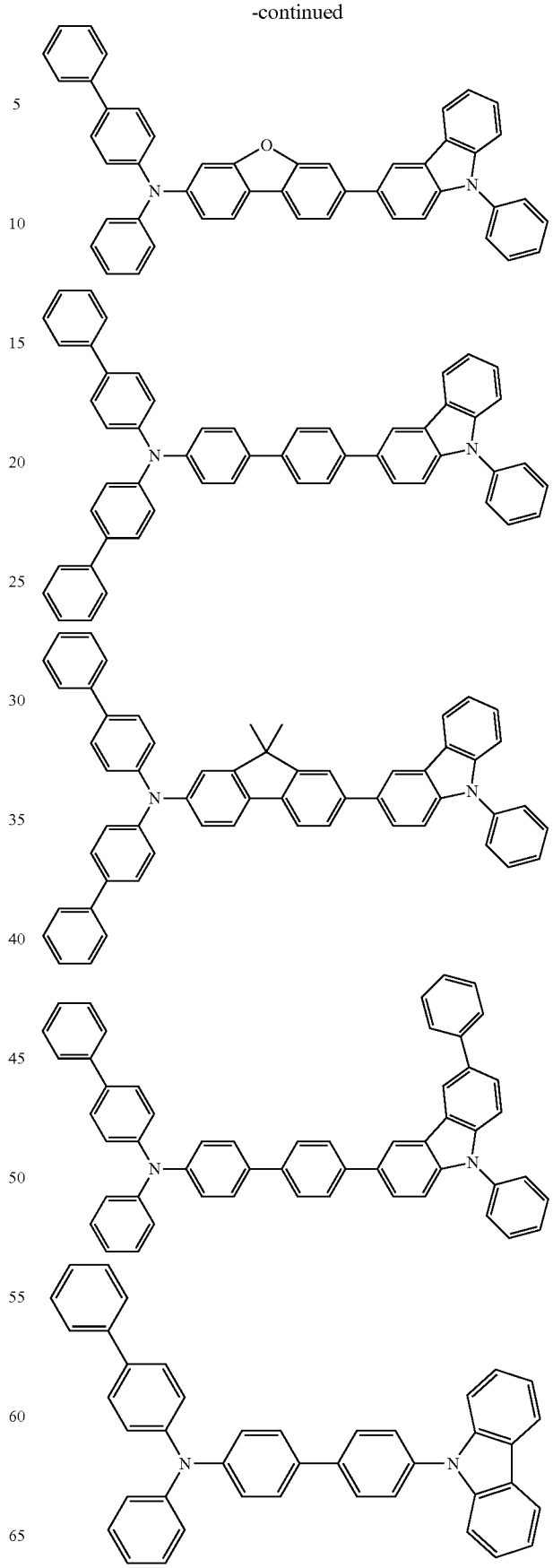

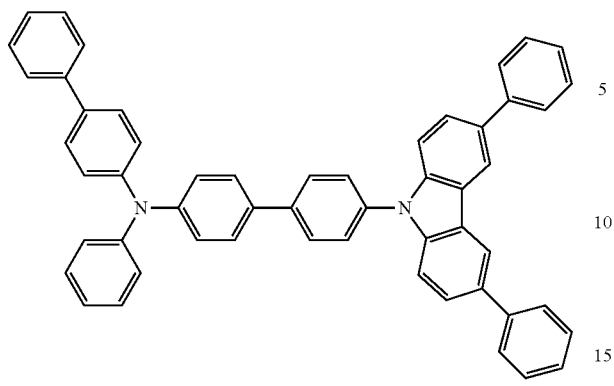

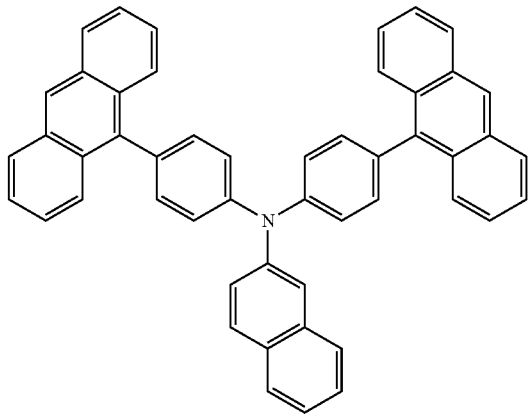

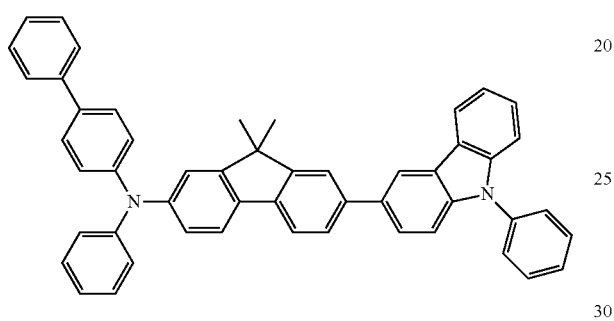

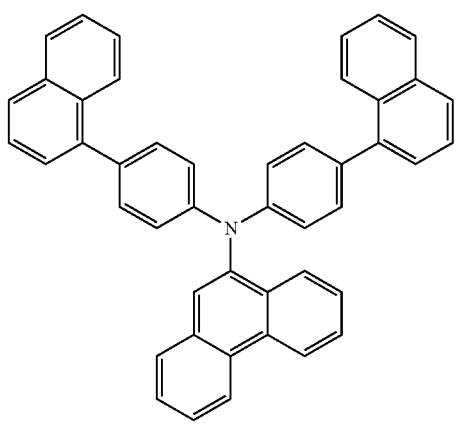

Aromatic amine represented by the following formula (II) can also be preferably used for forming the hole injecting layer or the hole transporting layer. Such a substance may be combined with the organic EL device material according to the exemplary embodiment of the invention for use in the emitting layer.

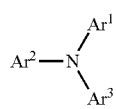  (II)

In the formula (II), $Ar^1$ to $Ar^3$ each represent the same as those represented by $Ar^1$ to $Ar^4$ of the formula (I). Examples of the compound represented by the formula (II) are shown below. However, the compound represented by the formula (II) is not limited thereto.

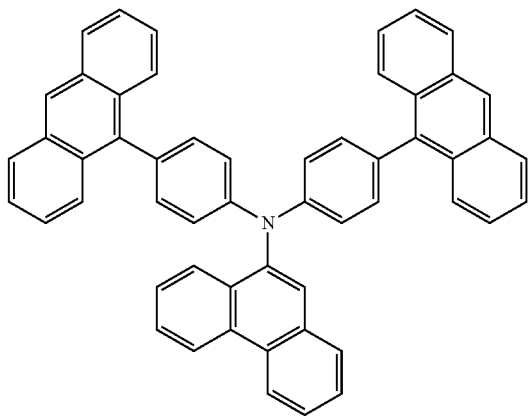

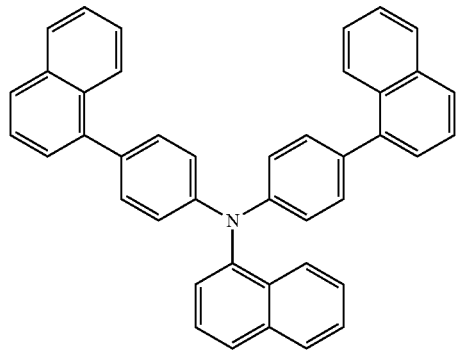

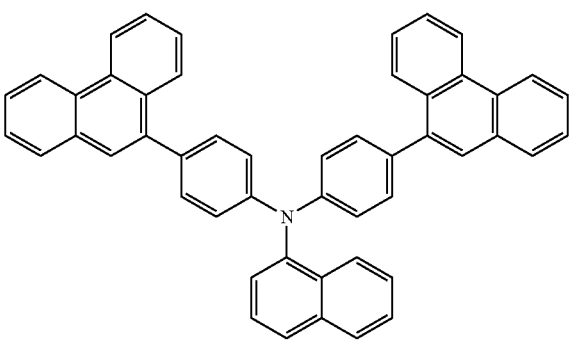

155
-continued
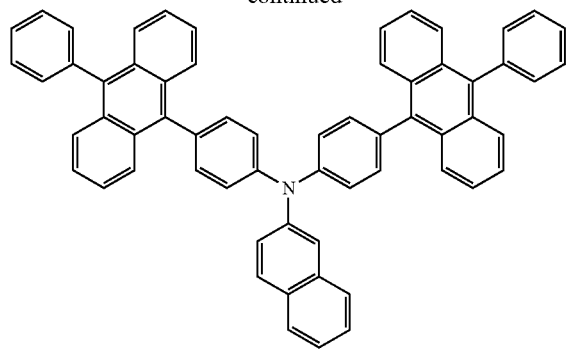
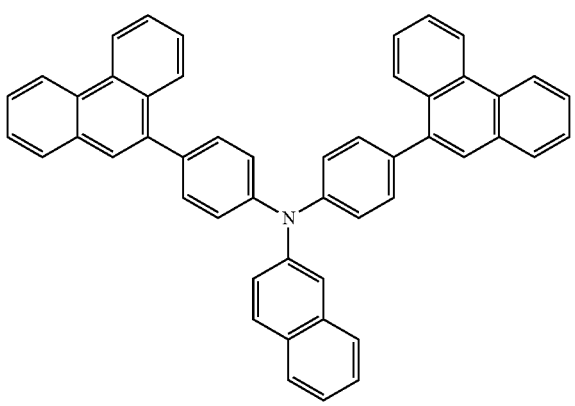
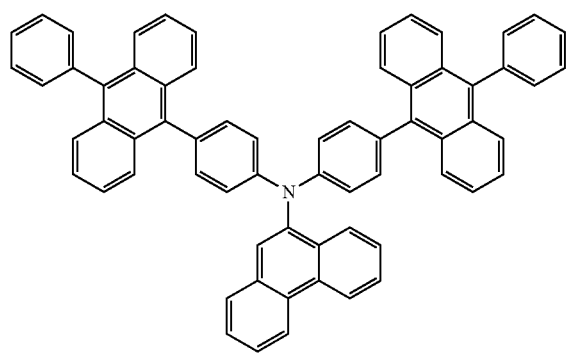
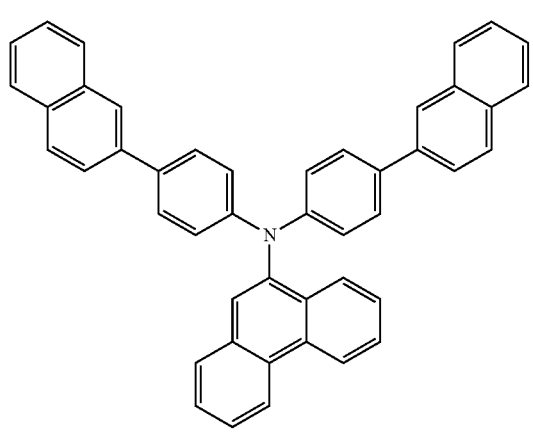
156
-continued
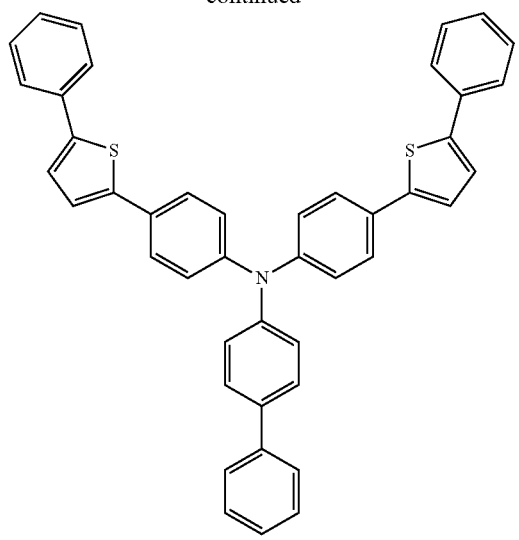
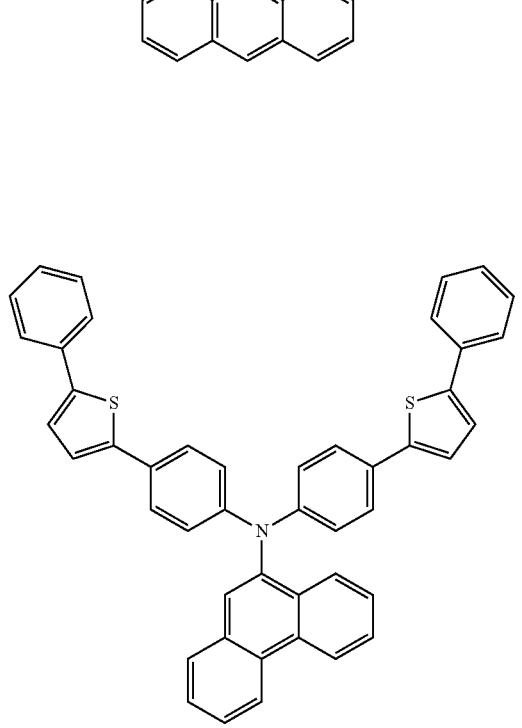

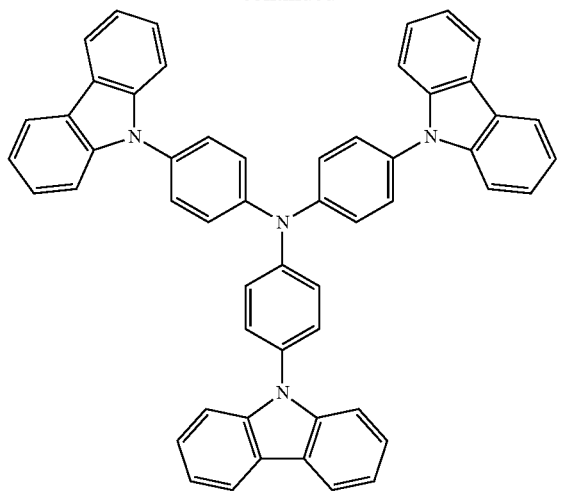

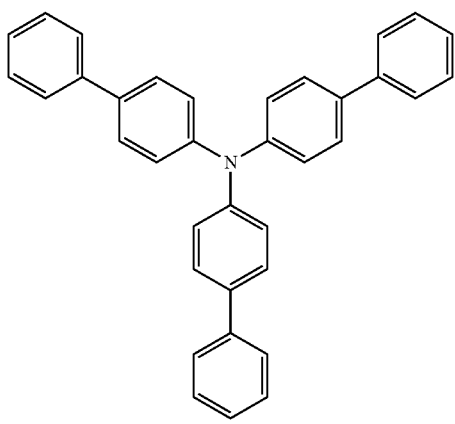

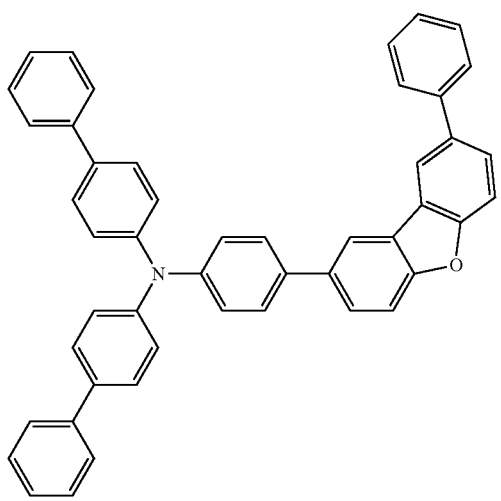

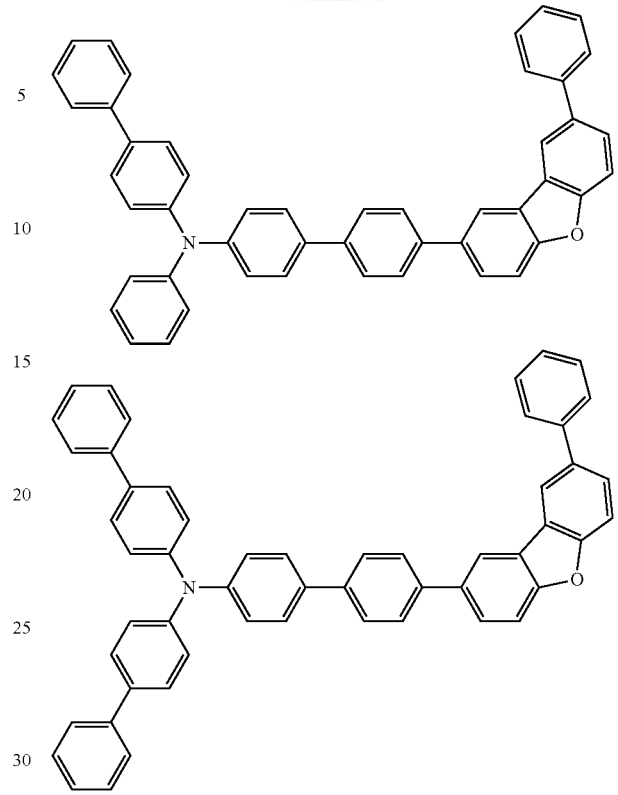

It should be noted that the invention is not limited to the above description, but may include any modification as long as such modification stays within a scope and a spirit of the invention.

For instance, the following is a preferable example of such modification made to the invention.

According to the exemplary embodiment of the invention, the emitting layer may also preferably contain an assistance material for assisting injection of charges.

When the emitting layer is formed of a host material that exhibits a wide energy gap, a difference in ionization potential (Ip) between the host material and the hole injecting/transporting layer etc. becomes so large that injection of the holes into the emitting layer becomes difficult, which may result in a rise in a driving voltage required for providing a sufficient luminance.

In the above instance, introducing a hole-injectable or hole-transportable assistance substance for assisting injection of charges in the emitting layer can contribute to facilitation of the injection of the holes into the emitting layer and to reduction of the driving voltage.

As the assistance substance for assisting the injection of charges, for instance, a general hole injecting material, a general hole transporting material or the like can be used.

Examples of the assistance material for assisting the injection of charges are triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, polysilane-base copolymers, aniline-base copolymers and conductive polymer oligomers (in particular, thiophene oligomer).

While the above are hole-injectable materials, porphyrin compounds, aromatic tertiary amine compounds and styrylamine compounds are preferable, among which aromatic tertiary amine compounds are particularly preferable.

In addition, 4,4'-bis(N-(1-naphthyl)-N-phenylamino)biphenyl (hereinafter, abbreviated as NPD) having in the molecule two fused aromatic rings, 4,4',4"-tris(N-(3-methylphenyl)-N-phenylamino)triphenylamine (hereinafter, abbreviated as MTDATA) in which three triphenylamine units are bonded in a starbust form, and the like may also be used.

Further, a hexaazatriphenylene derivative and the like can also favorably be used as the hole-injectable material.

Alternatively, inorganic compounds such as p-type Si and p-type SiC can also be used as the hole-injecting material.

A method of forming each of the layers in the organic EL device according to the exemplary embodiment of the invention is not particularly limited. A conventionally-known methods such as vacuum deposition or spin coating may be employed for forming the layers. The organic thin-film layer containing the compound represented by the formula (1), which is used in the organic EL device according to the exemplary embodiment of the invention, may be formed by a conventional coating method such as vacuum deposition, molecular beam epitaxy (MBE method) and coating methods using a solution such as a dipping, spin coating, casting, bar coating, and roll coating.

Although the thickness of each organic layer of the organic EL device is not particularly limited, the thickness is generally preferably in a range of several nanometers to 1 μm because an excessively-thinned film is likely to entail defects such as a pin hole while an excessively-thickened film requires high voltage to be applied and deteriorates efficiency.

EXAMPLES

Next, the invention will be described in further detail by using Example(s) and Comparative(s). However, the invention is not limited by the description of Example(s).

Synthesis of Compound No. 1

Ethanol (30 mL) was added with 3,5-dibromobenzaldehyde (8 g, 30 mmol) and 4-bromoacetophenone (6 g, 30 mmol) and further with 3M potassium hydroxide solution (30 mL), and was stirred at room temperature for seven hours. After a precipitated solid was separated by filtration, the obtained solid was cleansed with methanol. As a result, 11.7 g of a white solid, i.e., an intermediate body 1-1, was obtained at an yield of 87%.

Ethanol (300 mL) was added with the intermediate body 1-1 (11.7 g, 26 mmol) and benzamidine hydrochloride (4.1 g, 26 mmol) and further with sodium hydroxide (2.1 g, 53 mmol), and was heated to reflux for six hours. After a precipitated solid was separated by filtration, the obtained solid was cleansed with hexane. As a result, 4.3 g of a white solid, i.e., an intermediate body 1-2, was obtained at an yield of 30%.

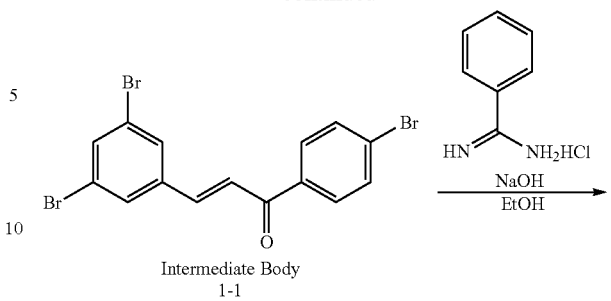

Intermediate Body 1-1

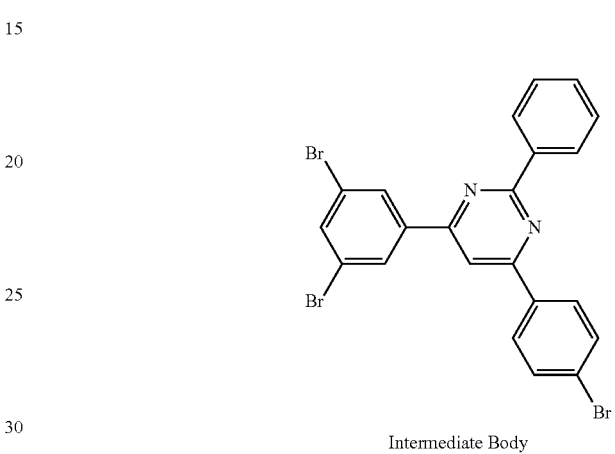

Intermediate Body 1-2

Under an argon gas atmosphere, the intermediate body 1-2 (4.0g, 7.3 mmol), carbazole (4.1 g, 24 mmol), CuI (1.4 g, 7.34 mmol), potassium carbonate (6.1 g, 44 mmol), anhydrous dioxane (30 mL) and cyclohexanediamine (0.84 g, 7.3 mmol) were mixed in a three-neck flask in this sequence, and were stirred at 100 degrees C. for eight hours.

The reaction solution was added with water to precipitate a solid. The obtained solid was cleansed with hexane and subsequently with methanol. The obtained solid was refined by silica-gel column chromatography, thereby obtaining 3.8 g of a white solid, i.e., a compound 1, at an yield of 64%.

FD-MS analysis consequently showed that m/e was equal to 804 while a calculated molecular weight was 804.

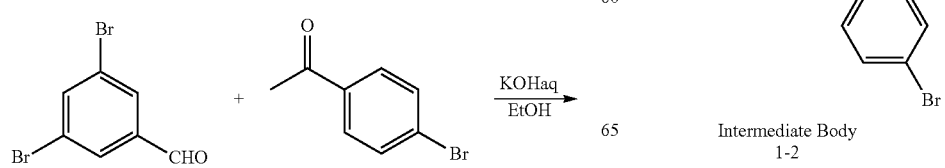

Intermediate Body 1-2

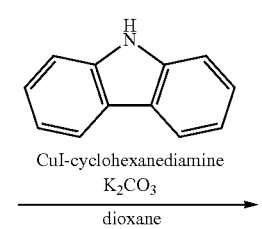

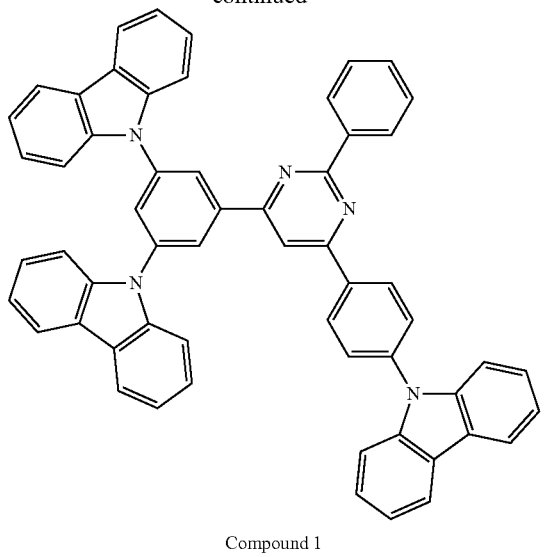

Compound 1

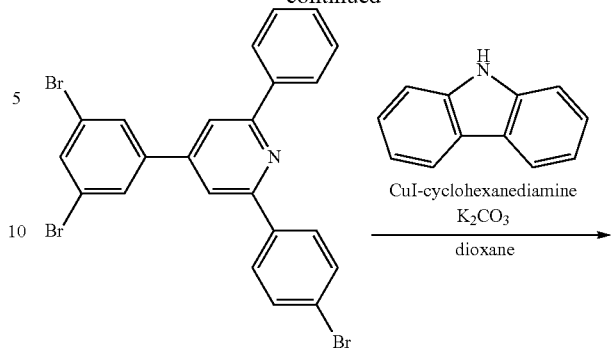

Intermediate Body 2-2

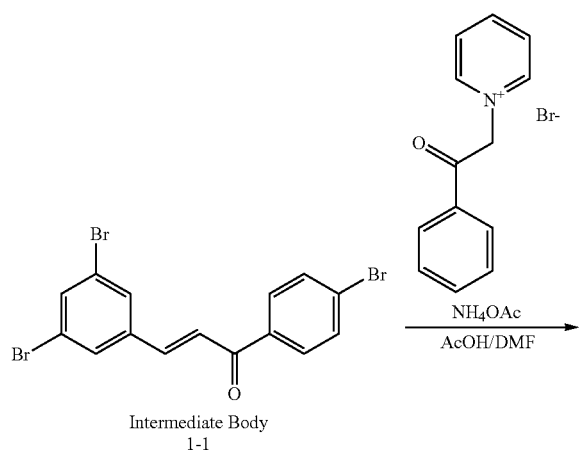

Compound 2

Synthesis of Compound No. 2

The intermediate body 1-1 (10 g, 22.6 mmol), phenacylpyridinium bromide (12.7 g, 45.6 mmol), ammonium acetate (45 g), acetic acid (200 mL) and N,N-dimethyl formamide (200 mL) were stirred for eight hours while being heated to reflux.

After the reaction solution was poured into ice water, a precipitated substance was separated by filtration and cleansed with methanol. The obtained solid was refined by silica-gel column chromatography (elution solvent: hexane/methylene chloride), thereby obtaining 5.8 g of an intermediate body 2-2 at an yield of 47%.

Under an argon gas atmosphere, the intermediate body 2-2 (3.9 g, 7.3 mmol), carbazole (4.1 g, 24 mmol), CuI (1.4 g, 7.34 mmol), potassium carbonate (6.1 g, 44 mmol), anhydrous dioxane (30 mL) and cyclohexanediamine (0.84 g, 7.3 mmol) were mixed in a three-neck flask in this sequence, and were stirred at 100 degrees C. for eight hours.

The reaction solution was added with water to precipitate a solid. The obtained solid was cleansed with hexane and subsequently with methanol. The obtained solid was then refined by silica-gel column chromatography, thereby obtaining 3.5 g of a compound 2 at an yield of 60%.

FD-MS analysis consequently showed that m/e was equal to 802 while a calculated molecular weight was 802.

Synthesis of Compound No. 3

Under a nitrogen gas atmosphere, trichlorotriazine (10 g, 54.7 mmol), 4-(N-carbazolyl)phenylboronic acid (14.1 g, 49.2 mmol), tetrakis(triphenylphosphine)palladium (1.1 g, 1 mmol), toluene (160 mL) and 2M sodium carbonate solution (80 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 8.7 g of an intermediate body 3-1 was obtained at an yield of 22.3%.

Under a nitrogen gas atmosphere, the intermediate body 3-1 (8 g, 20.5 mmol), 3,5-di(N-carbazolyl)phenylboronic acid (9.3 g, 20.5 mmol), tetrakis(triphenylphosphine)palladium (0.43 g, 0.4 mmol), toluene (60 mL) and 2M sodium carbonate solution (30 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 7.9 g of an intermediate body 3-2 was obtained at an yield of 50.6%.

Under a nitrogen gas atmosphere, the intermediate body 3-2 (7 g, 9.8 mmol), phenylboronic acid (1.3 g, 10.8 mmol), tetrakis(triphenylphosphine)palladium (0.21 g, 0.2 mmol), toluene (30 mL) and 2M sodium carbonate solution (15 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 5.2 g of a compound 3 was obtained at an yield of 66%. FD-MS analysis consequently showed that m/e was equal to 804 while a calculated molecular weight was 804.

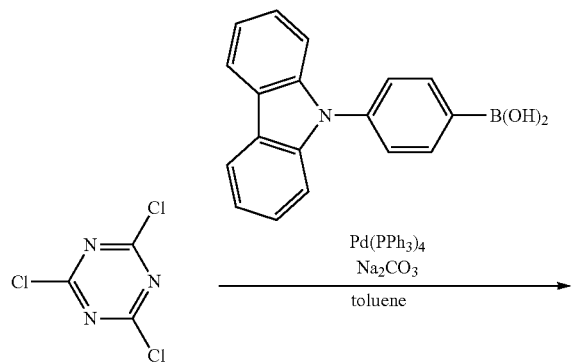

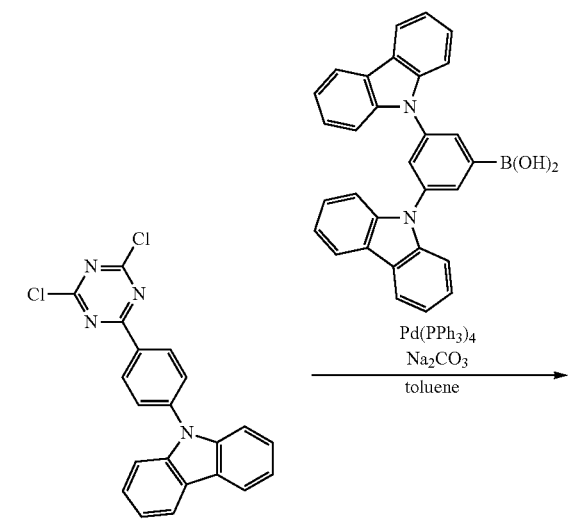

Intermediate Body 3-1

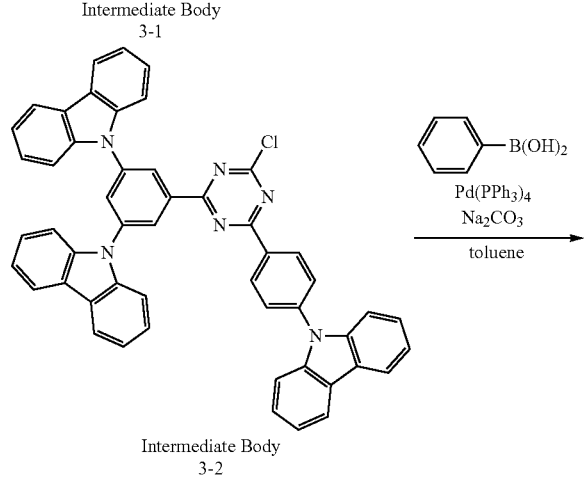

Intermediate Body 3-2

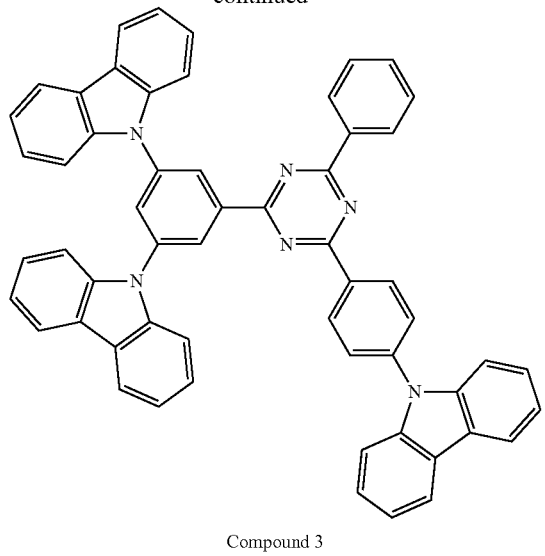

Compound 3

Synthesis of Compound 4

Under a nitrogen gas atmosphere, 4-bromoacetophenone (19.8 g, 100 mmol), N-phyenylcarbazolyl-3-boronic acid (28.7 g, 100 mmol), tetrakis(triphenylphosphine)palladium (2.1 g, 2 mmol), toluene (300 mL) and 2M sodium carbonate solution (150 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 18.3 g of an intermediate body 4-1 was obtained at an yield of 50.7%.

Ethanol (80 mL) was added with 3,5-dibromobenzaldehyde (13.1 g, 50 mmol) and the intermediate body 4-1 (18.1 g, 50 mmol) and further with 3M potassium hydroxide solution (40 mL), and was stirred at room temperature for seven hours. After a precipitated solid was separated by filtration, the obtained solid was cleansed with methanol. As a result, 20.3 g of a white solid, i.e., an intermediate body 4-2, was obtained at an yield of 67%. Ethanol (300 mL) was added with the intermediate body 4-2 (15.7 g, 26 mmol) and benzamidine hydrochloride (4.1 g, 26 mmol) and further with sodium hydroxide (2.1 g, 53 mmol), and was heated to reflux for eight hours. After a precipitated solid was separated by filtration, the obtained solid was cleansed with hexane. As a result, 6.2 g of a white solid, i.e., an intermediate body 4-3, was obtained at an yield of 34%.

Under an argon gas atmosphere, the intermediate body 4-3 (5.1 g, 7.3 mmol), carbazole (3.1 g, 18.3 mmol), CuI (1.4 g, 7.34 mmol), potassium carbonate (6.1 g, 44 mmol), anhydrous dioxane (30 mL) and cyclohexanediamine (0.84 g, 7.3 mmol) were mixed in a three-neck flask in this sequence, and were stirred at 100 degrees C. for eight hours. The reaction solution was added with water to precipitate a solid. The obtained solid was cleansed with hexane and subsequently with methanol. The obtained solid was then refined by silica-gel column chromatography, thereby obtaining 2.7 g of a compound 4 at an yield of 42%.

FD-MS analysis consequently showed that m/e was equal to 880 while a calculated molecular weight was 880.

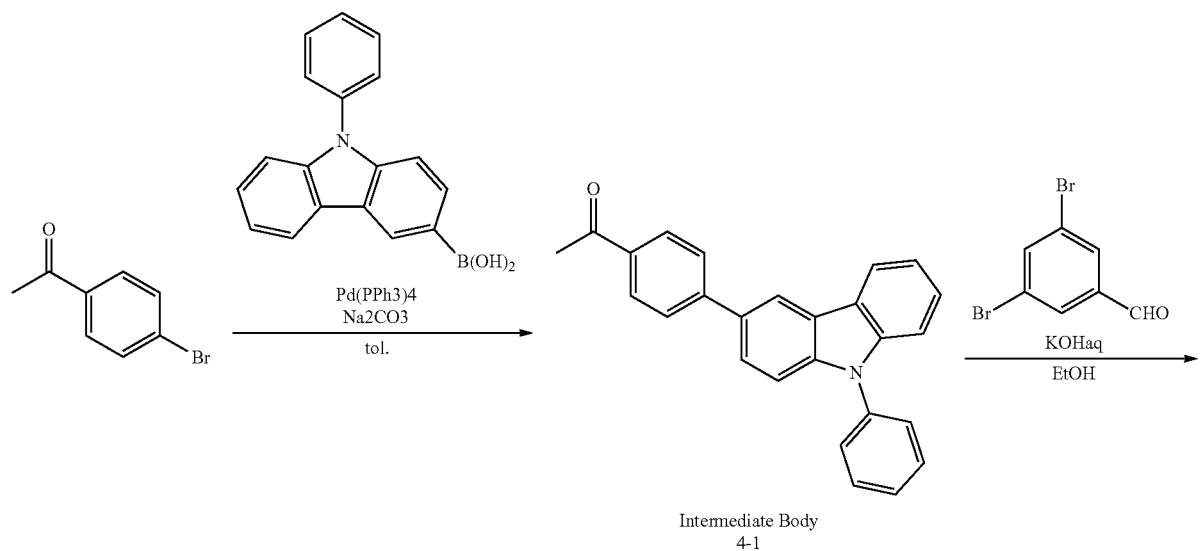
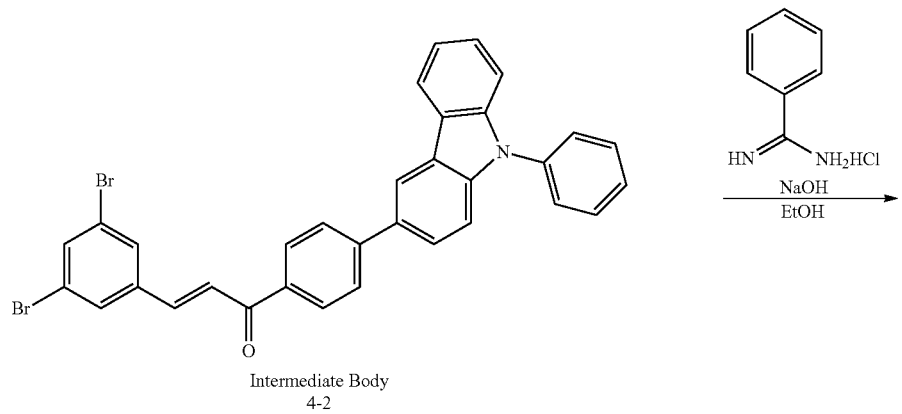
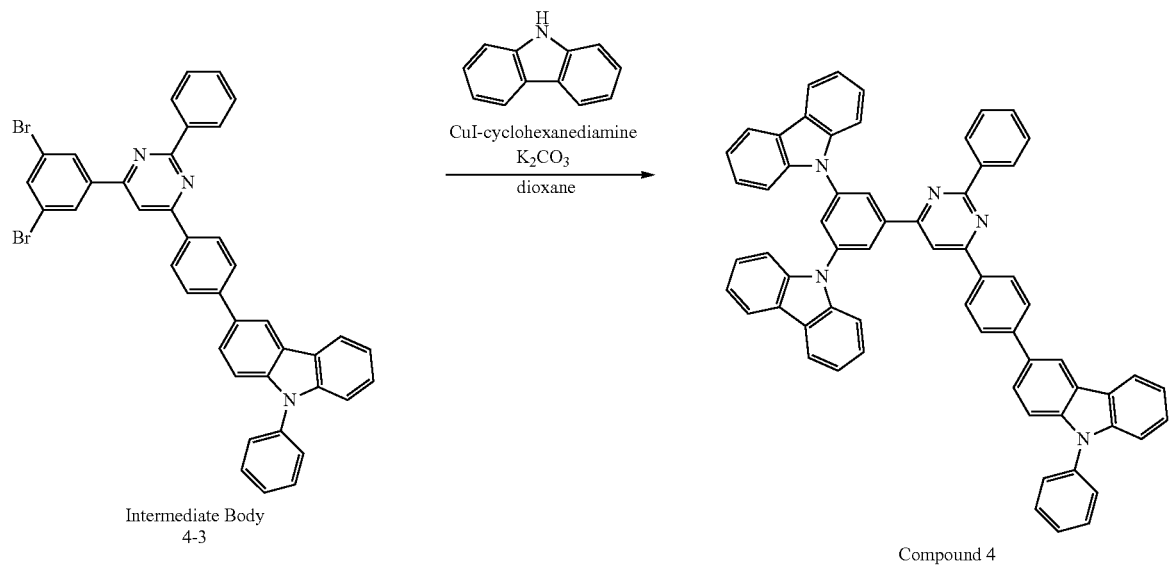

Synthesis of Compound 5

Under a nitrogen gas atmosphere, 3-acetylphenylboronic acid (16.4 g, 100 mmol), 4-bromoiodobenzene (28.2 g, 100 mmol), tetrakis(triphenylphosphine)palladium (2.1 g, 2 mmol), toluene (300 mL) and 2M sodium carbonate solution (150 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 18.7 g of an intermediate body 5-1 was obtained at an yield of 68%.

Ethanol (80 mL) was added with 3,5-dibromobenzaldehyde (13.1 g, 50 mmol) and the intermediate body 5-1 (13.8 g, 50 mmol) and further with 3M potassium hydroxide solution (40 mL), and was stirred at room temperature for seven hours. After a precipitated solid was separated by filtration, the obtained solid was cleansed with methanol. As a result, 20.3 g of an intermediate body 5-2 was obtained at an yield of 78%.

Ethanol (300 mL) was added with the intermediate body 5-2 (13.5 g, 26 mmol) and benzamidine hydrochloride (4.1 g, 26 mmol) and further with sodium hydroxide (2.1 g, 53 mmol), and was heated to reflux for eight hours. After a precipitated solid was separated by filtration, the obtained solid was cleansed with hexane. As a result, 4.5 g of an intermediate body 5-3 was obtained at an yield of 28%.

Under an argon gas atmosphere, the intermediate body 5-3 (4.5 g, 7 3 mmol), carbazole (3.1 g, 18 3 mmol), CuI (1.4 g, 7.34 mmol), potassium carbonate (6.1 g, 44 mmol), anhydrous dioxane (30 mL) and cyclohexanediamine (0.84 g, 7.3 mmol) were mixed in a three-neck flask in this sequence, and were stirred at 100 degrees C. for eight hours. The reaction solution was added with water to precipitate a solid. The obtained solid was cleansed with hexane and subsequently with methanol. The obtained solid was then refined by silica-gel column chromatography, thereby obtaining 3.5 g of a compound 5 at an yield of 55%.

FD-MS analysis consequently showed that m/e was equal to 878 while a calculated molecular weight was 878.

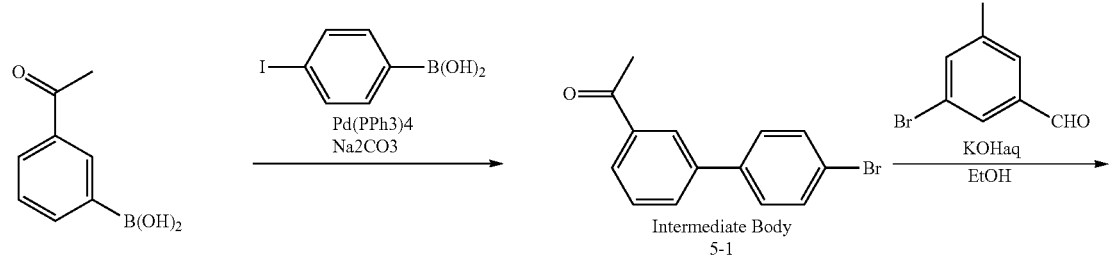

Intermediate Body 5-1

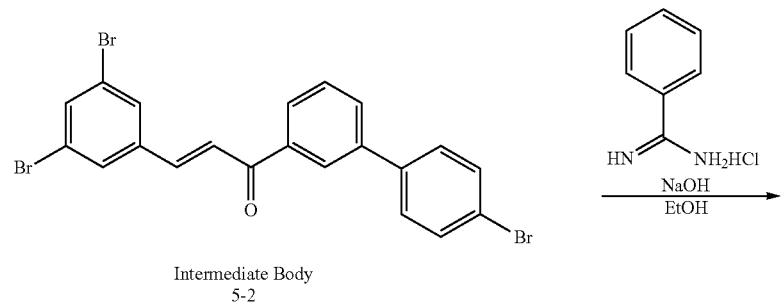

Intermediate Body 5-2

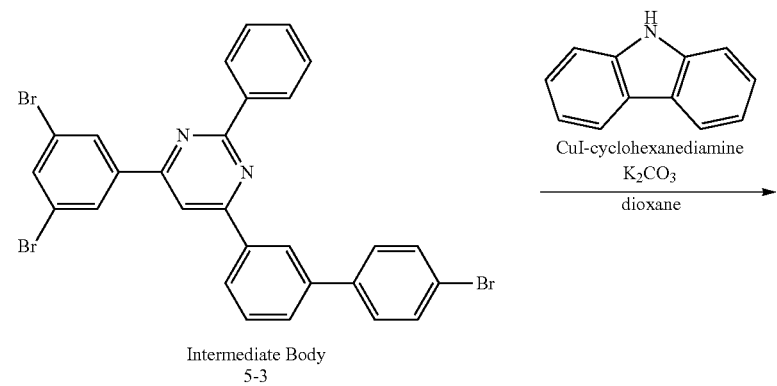

Intermediate Body 5-3

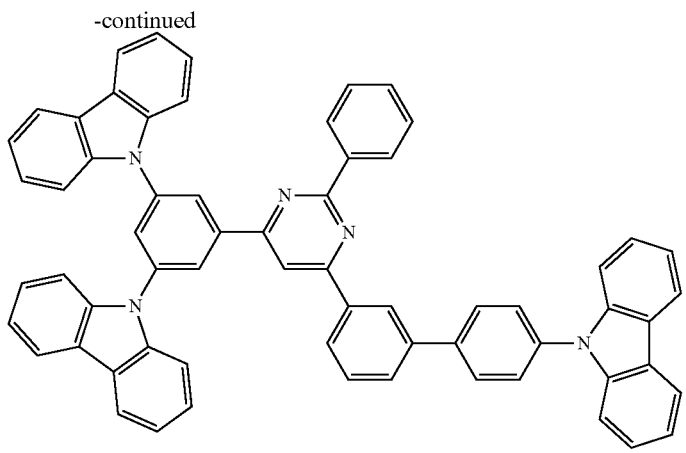

Compound 5

Synthesis of Compound 6

Under a nitrogen gas atmosphere, trichloropyrimidine (18.2 g, 100 mmol), phenylboronic acid (12.2 g, 100 mmol), palladium acetate (0.45 g, 2 mmol), toluene (300 mL) and 2M sodium carbonate solution (150 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 16.2 g of an intermediate body 6-1 was obtained at an yield of 72%.

Under a nitrogen gas atmosphere, the intermediate body 6-1 (15.7 g, 70 mmol), 4-(N-carbazolyl)phenylboronic acid (20.1 g, 70 mmol), tetrakis(triphenylphosphine)palladium (1.62 g, 1.4 mmol), toluene (200 mL) and 2M sodium carbonate solution (105 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 20.6 g of an intermediate body 6-2 was obtained at an yield of 68%.

Under a nitrogen gas atmosphere, the intermediate body 6-2 (4.3 g, 10 mmol), 3,5-di(N-carbazolyl)phenylboronic acid (4.5 g, 10 mmol), tetrakis(triphenylphosphine)palladium (0.23 g, 0.2 mmol), toluene (30 mL) and 2M sodium carbonate solution (15 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 4.8 g of a compound 6 was obtained at an yield of 60%.

FD-MS analysis consequently showed that m/e was equal to 804 while a calculated molecular weight was 804.

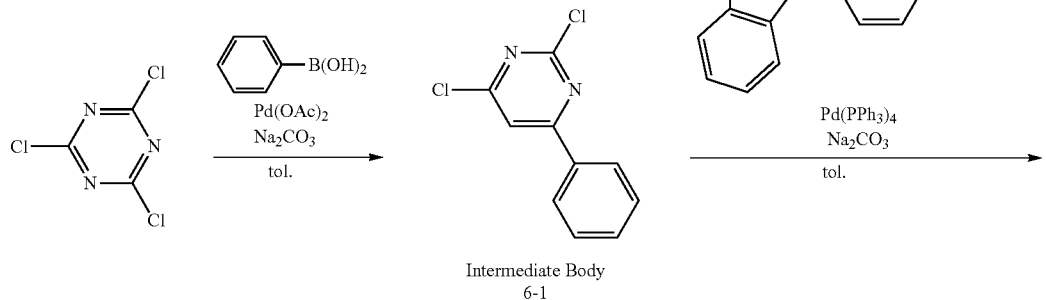

Intermediate Body 6-1

-continued

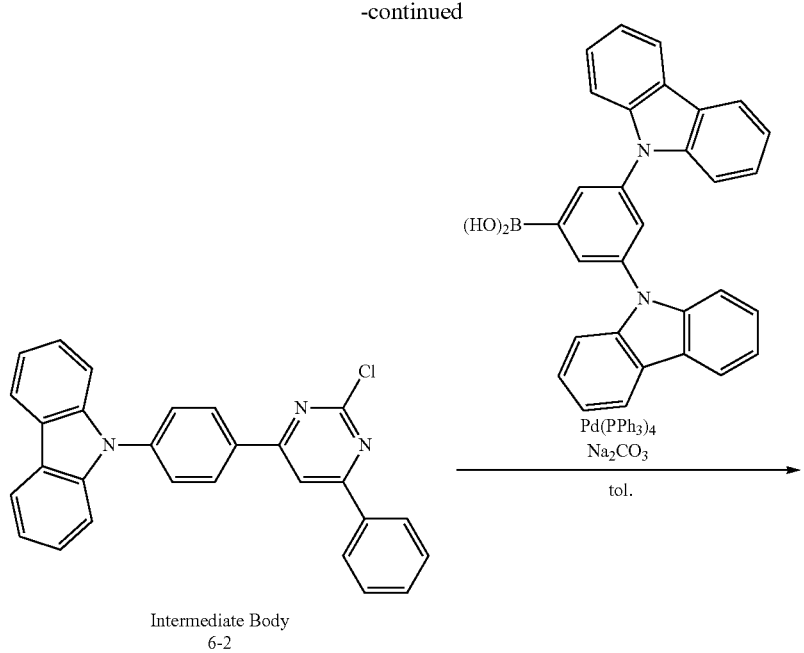

Intermediate Body 6-2

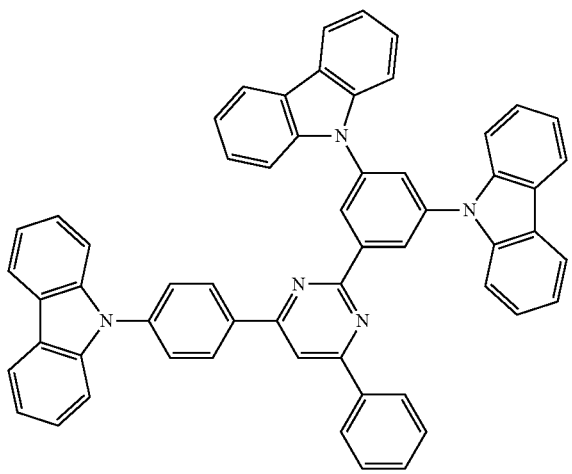

Compound 6

Synthesis of Compound 7

Under a nitrogen gas atmosphere, the intermediate body 6-1 (9 g, 40 mmol), 3,5-di(N-carbazolyl)phenylboronic acid (18.1 g, 40 mmol), tetrakis(triphenylphosphine)palladium (0.92 g, 0.8 mmol), toluene (120 mL) and 2M sodium carbonate solution (60 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 13.1 g of an intermediate body 7-1 was obtained at an yield of 55%.

Under a nitrogen gas atmosphere, the intermediate body 7-1 (6.0 g, 10 mmol), 4-(N-carbazolyl)phenylboronic acid (2.9 g, 10 mmol), tetrakis(triphenylphosphine)palladium (0.23 g, 0.2 mmol), toluene (30 mL) and 2M sodium carbonate solution (15 mL) were mixed in sequence, and were heated to reflux for eight hours.

After the reaction solution was cooled down to the room temperature, an organic layer was separated and an organic solvent was distilled away under reduced pressure. Residue thereof was refined by silica-gel column chromatography, so that 5.9 g of a compound 7 was obtained at an yield of 74%.

FD-MS analysis consequently showed that m/e was equal to 804 while a calculated molecular weight was 804.

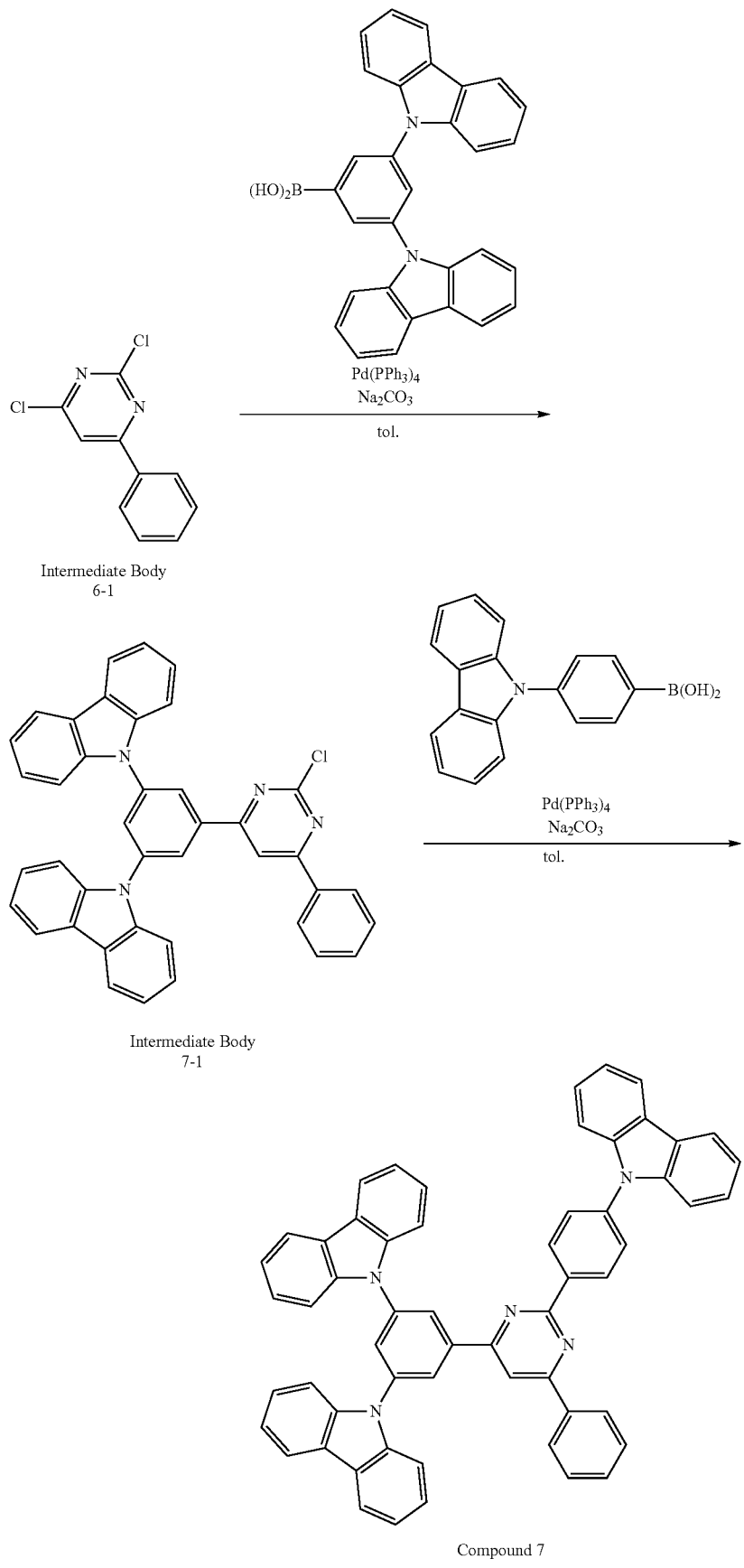

Example 1

Manufacture of Organic EL Device 1

A glass substrate (size: 25 mm×75 mm×1.1 mm) having an ITO transparent electrode (manufactured by Geomatec Co., Ltd.) was ultrasonic-cleaned in isopropyl alcohol for five minutes, and then UV (Ultraviolet)/ozone-cleaned for 30 minutes.

After the glass substrate having the transparent electrode line was cleaned, the glass substrate was mounted on a substrate holder of a vacuum deposition apparatus, and a 40-nm thick film of a compound A was initially vapor-deposited on a surface of the glass substrate where the transparent electrode line was provided so as to cover the transparent electrode, thereby obtaining a hole injecting layer. On this film, a 20-nm thick film of a compound B was vapor-deposited, thereby obtaining a hole transporting layer.

On the hole transporting layer, the compound 1 as a phosphorescent host and an Ir(Ph-ppy)$_3$ as a phosphorescent dopant were co-evaporated (thickness: 40 nm), thereby obtaining a phosphorescent-emitting layer. The concentration of the Ir(Ph-ppy)$_3$ was 20 mass %.

On the phosphorescent-emitting layer, a 30-nm thick film of a compound C, a 1-nm thick film of LiF, an 80-nm thick film of a metal Al were laminated in sequence, thereby obtaining a cathode. Incidentally, the film of LiF as an electron-injecting electrode was formed at a speed of 1 Å/min.

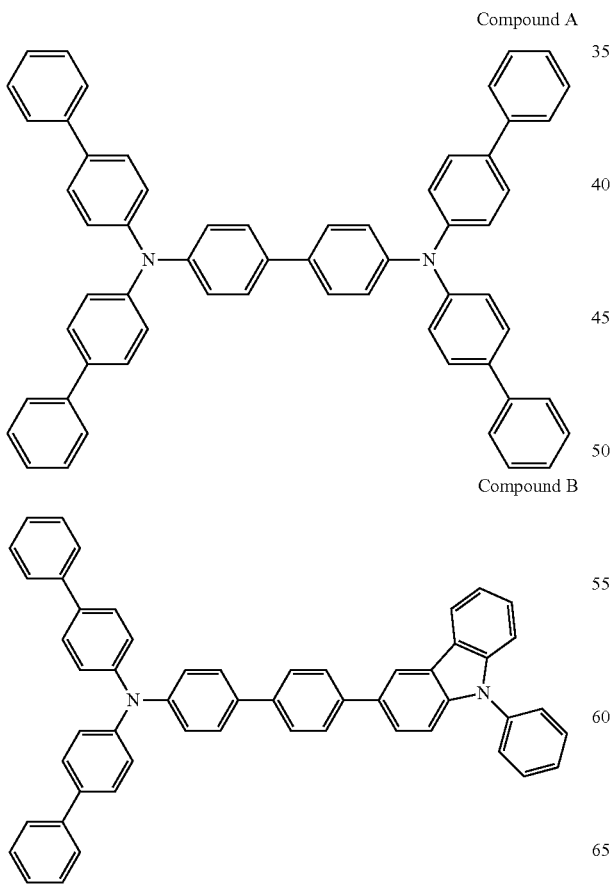

Compound A

Compound B

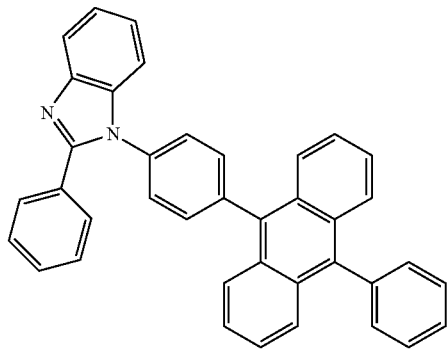

Compound C

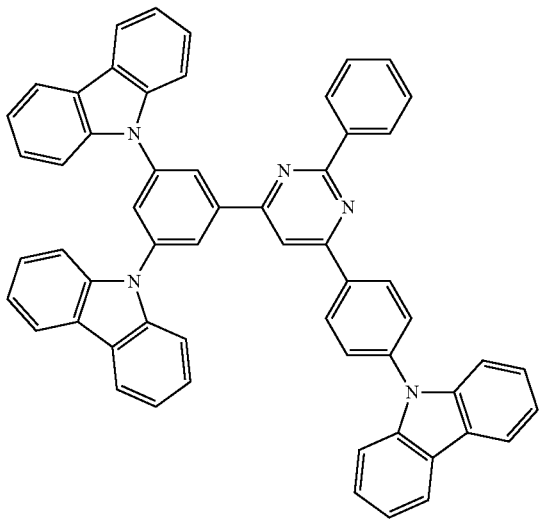

Compound No. 1

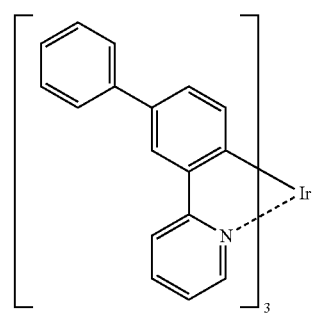

Ir(Ph-ppy)$_3$ (facial body)

Examples 2 to 7

Manufacture of Organic EL Devices 2 to 7

Organic EL devices 2 to 7 were manufactured in the manner according to Example 1 except for using the following compounds No. 2 to 7 in place of the compound No. 1.

Compound No. 2

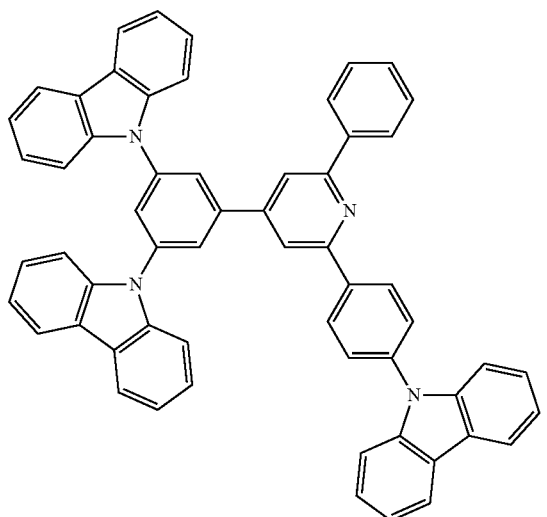

Compound No. 3

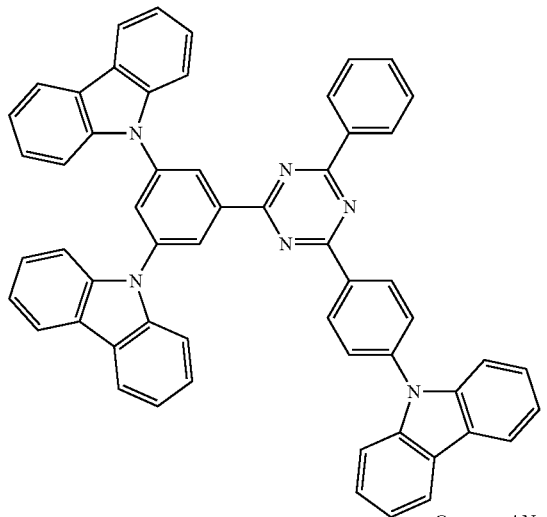

Compound No. 4

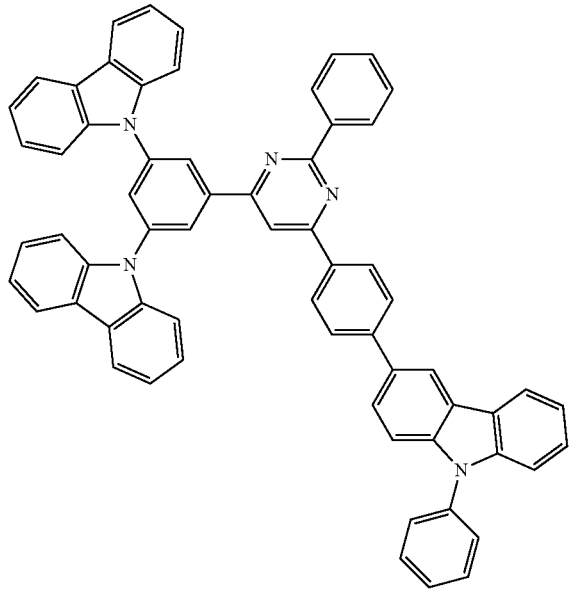

Compound No. 5

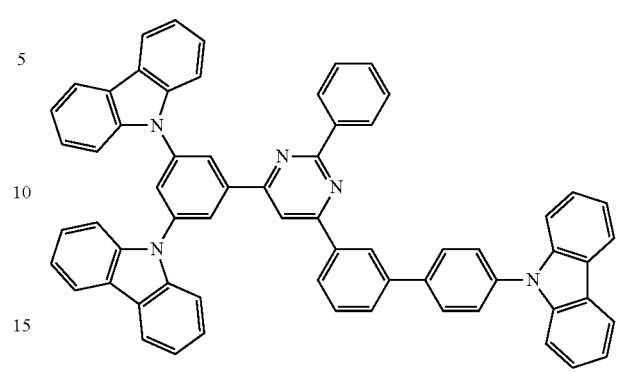

Compound No. 6

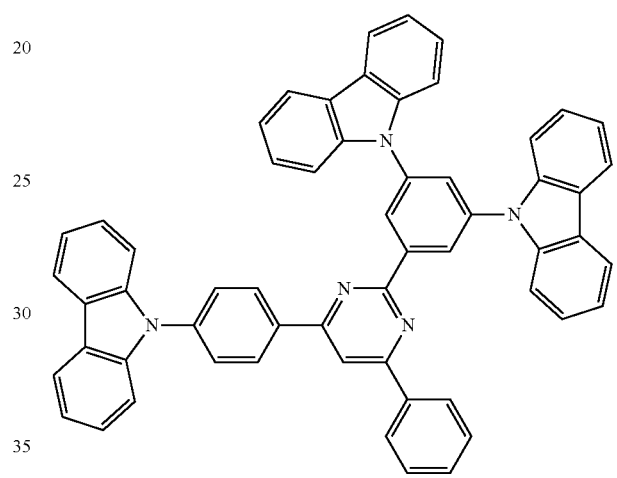

Compound No. 7

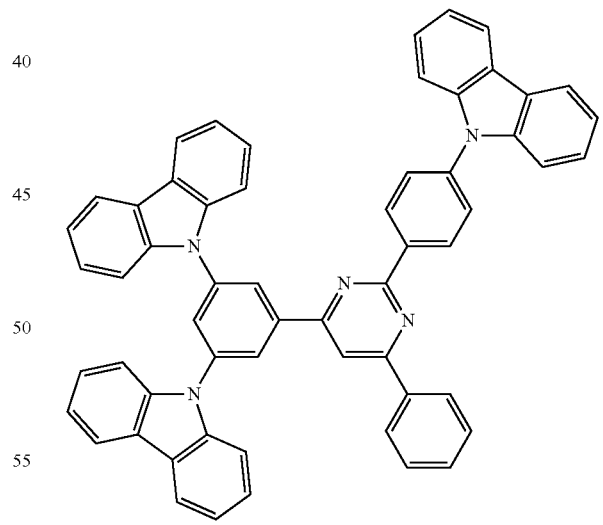

Evaluation on Emitting Performance of Organic EL Device

Each of the organic EL devices 1 to 5 manufactured as described above was driven by direct-current electricity to emit light, and emitting performance was evaluated while time elapsed until the initial luminance intensity of 20,000 cd/m$^2$ was reduced to the half was measured for each organic EL device. The results of the evaluation are shown in Table 1.

Comparatives 1 to 3

Organic EL devices were manufactured in the manner according to Example 1 except for using comparative compounds 1 to 3 as a host material in place of the compound 1 of Example 1. For each of these organic EL devices, emitting performance was evaluated and time elapsed until the initial luminance intensity of 20,000 cd/m² was reduced was measured. The results of the evaluation are shown in Table 1.

Comparative Compound 1

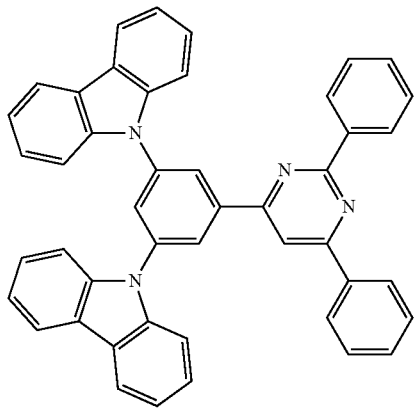

Comparative Compound 2

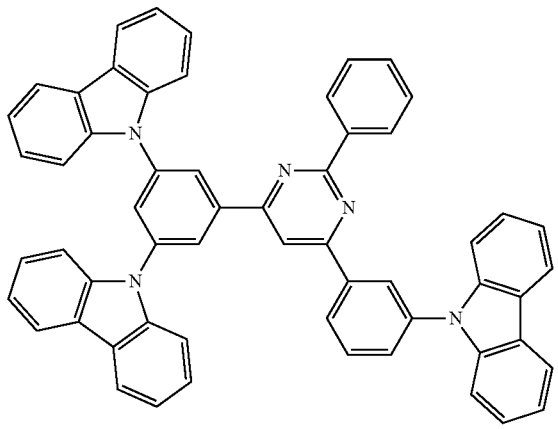

Comparative Compound 3

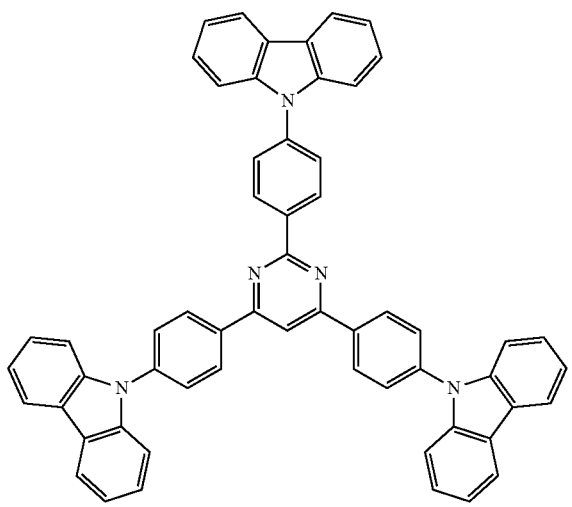

TABLE 1

| | Host Compound | Voltage (V) @1 mA/cm² | Luminous Efficiency (cd/A) @1 mA/cm² | Time until Half-Life (hrs) |
|---|---|---|---|---|
| Example 1 | Compound No. 1 | 4.2 | 65 | 820 |
| Example 2 | Compound No. 2 | 4.2 | 63 | 750 |
| Example 3 | Compound No. 3 | 4.1 | 60 | 700 |
| Example 4 | Compound No. 4 | 4.3 | 61 | 680 |
| Example 5 | Compound No. 5 | 4.2 | 58 | 710 |
| Example 6 | Compound No. 6 | 4.2 | 57 | 710 |
| Example 7 | Compound No. 7 | 4.2 | 55 | 730 |
| Comparative 1 | Comparative Compound 1 | 4.5 | 54 | 450 |
| Comparative 2 | Comparative Compound 2 | 5.0 | 50 | 410 |
| Comparative 3 | Comparative Compound 3 | 4.6 | 48 | 350 |

It has been found from Table 1 that in comparison to Comparatives 1 to 3, each of Examples 1 to 7 using the compounds according to the invention: provides a significantly long time elapsed until the initial luminance intensity is reduced; is adapted for low-voltage driving; and exhibits a high luminous efficiency.

What is claimed is:
1. An organic EL device material comprising:
   a unit comprising a 3,5-biscarbazolylphenyl group
   a unit comprising a 4-carbazolylphenyl group; and
   a compound comprising a unit comprising a nitrogen-containing aromatic heterocyclic ring bonding the unit comprising the 3,5-biscarbazolylphenyl group and the unit comprising the 4-carbazolylphenyl group, wherein the organic EL material is represented by a formula (4)

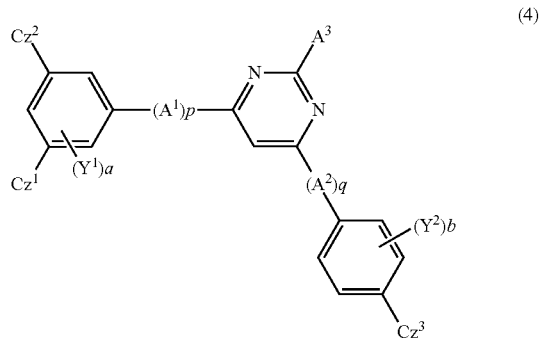

(4)

where: $A^1$, $A^2$ and $A^3$ each represent a substituted or unsubstituted aromatic hydrocarbon group having 6 to 60 ring carbon atoms;
$Cz^1$ to $Cz^3$ each independently represent a substituted or unsubstituted carbazolyl group and is allowed to be mutually the same or different;
$Y^1$ and $Y^2$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms;

a represents an integer of 0 to 3 and b represents an integer of 0 to 4;

p and q each independently represent an integer of 0 to 3;

when p is 2 or more, $A^1$ is allowed to be the same or different; and when q is 2 or more, $A^2$ is allowed to be the same or different

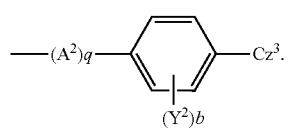

(3)

2. An organic EL device comprising:

a cathode;

an anode; and an organic thin-film layer provided between the cathode and the anode, the organic thin-film layer formed out of one or more layers comprising an emitting layer, wherein at least one layer of the organic thin-film layer comprises the organic EL device material according to claim 1.

3. The organic EL device according to claim 2, wherein the emitting layer comprises the organic EL device material as a host material.

4. The organic EL device according to claim 2, wherein the emitting layer further comprises a phosphorescent material.

5. The organic EL device according to claim 4, wherein the emitting layer comprises a host material and a phosphorescent material, the phosphorescent material being an ortho metalation of a complex of a metal atom selected from the group consisting of iridium (Ir), osmium (Os) and platinum (Pt).

6. The organic EL device according to claim 2, wherein the organic thin-film layer comprises an electron injecting layer provided between the cathode and the emitting layer, the electron injecting layer comprising a nitrogen-containing cyclic derivative.

7. The organic EL device according to claim 2, wherein the organic thin-film layer comprises an electron transporting layer provided between the cathode and the emitting layer, the electron transporting layer comprising the organic EL device material.

8. The organic EL device according to claim 2, wherein a reduction-causing dopant is present at an interfacial region between the cathode and the organic thin-film layer.

9. The organic EL device material according to claim 2, wherein each of $Cz^1$ to $Cz^3$ in the formula (4) is independently represented by a formula (5) or a formula (6) shown below

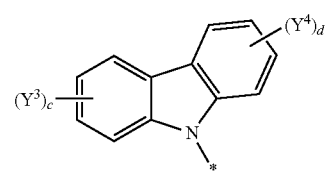

(5)

where: $Y^3$ and $Y^4$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms;

c and d each independently represent an integer of 1 to 4; and

"*" represents a bond position to a benzene ring

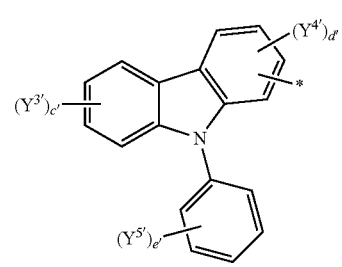

(6)

where: $Y^{3'}$, $Y^{4'}$ and $Y^{5'}$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms;

c' represents an integer of 1 to 4, d' represents an integer of 1 to 3, and e' represents an integer of 1 to 5; and "*" represents a bond position to a benzene ring.

10. The organic EL device material according to claim 1, wherein q=0 in the formula (4).

11. An organic EL device material comprising:
a unit comprising a 3,5-biscarbazolylphenyl group;
a unit comprising a 4-carbazolylphenyl group; and
a compound comprising a unit comprising a nitrogen-containing aromatic heterocyclic ring bonding the unit comprising the 3,5-biscarbazolylphenyl group and the unit comprising the 4-carbazolylphenyl group, wherein the organic EL material is represented by a formula (1)

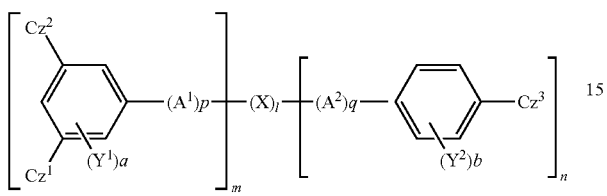

where: $A^1$ and $A^2$ each represent a substituted or unsubstituted aromatic hydrocarbon group having 6 to 60 ring carbon atoms;
$Cz^1$ to $Cz^3$ each independently represent a substituted or unsubstituted carbazolyl group and is allowed to be mutually the same or different;
X represents a substituted or unsubstituted nitrogen-containing aromatic heterocyclic ring selected from the group consisting of a substituted triazine ring, an unsubstituted triazine ring, a substituted indole ring and an unsubstituted indole ring;
$Y^1$ and $Y^2$ each independently represent a hydrogen atom, a fluorine atom, a cyano group, a substituted or unsubstituted and linear, branched or cyclic alkyl group having 1 to 20 carbon atoms, a substituted or unsubstituted and linear, branched or cyclic alkoxy group having 1 to 20 carbon atoms, a substituted or unsubstituted and linear, branched or cyclic haloalkyl group having 1 to 20 carbon atoms, a substituted or unsubstituted and linear, branched or cyclic haloalkoxy group having 1 to 20 carbon atoms, a substituted or unsubstituted and linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 10 ring carbon atoms;
a represents an integer of 0 to 3 and b represents an integer of 0 to 4;
l, m and n each independently represent an integer of 1 to 3;
when l is 2 or more, X is allowed to be the same or different;
m represents an integer of 1 to 3 as the number of substituent(s) being directly bonded to X and being represented by a formula (2) shown below;
when m is 2 or more, structures represented by the formula (2) is allowed to be the same or different;
n represents an integer of 1 to 3 as the number of substituent(s) being directly bonded to X and being represented by a formula (3) shown below;
when n is 2 or more, structures represented by the formula (3) is allowed to be the same or different;
p and q each independently represent an integer of 0 to 3;
when p is 2 or more, $A^1$ is allowed to be the same or different; and
when q is 2 or more, $A^2$ is allowed to be the same or different

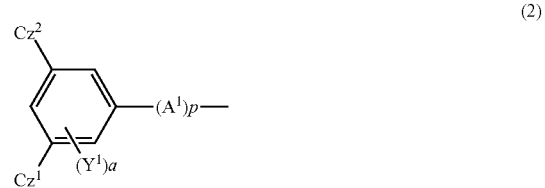

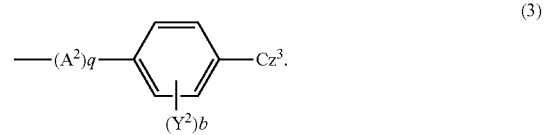

* * * * *

UNITED STATES PATENT AND TRADEMARK OFFICE
CERTIFICATE OF CORRECTION

PATENT NO. : 8,785,003 B2
APPLICATION NO. : 13/041071
DATED : July 22, 2014
INVENTOR(S) : Tetsuya Inoue et al.

It is certified that error appears in the above-identified patent and that said Letters Patent is hereby corrected as shown below:

On the title page, Item (73), the Assignee information is incorrect. Item (73) should read:

-- (73) Assignee: Idemitsu Kosan Co., Ltd., Tokyo (JP) --

Signed and Sealed this
Sixth Day of January, 2015

Michelle K. Lee
*Deputy Director of the United States Patent and Trademark Office*